(12) United States Patent
Dalziel et al.

(10) Patent No.: US 10,493,035 B2
(45) Date of Patent: Dec. 3, 2019

(54) TABLETS COMPRISING 2-HYDROXY-6-((2-(1-ISOPROPYL-1H-PYRAZOL-5-YL) PYRIDIN-3-YL)METHOXY)BENZALDEHYDE

(71) Applicant: Global Blood Therapeutics, Inc., South San Francisco, CA (US)

(72) Inventors: Sean Mark Dalziel, Burlingame, CA (US); Naveen Bejugam, Santa Clara, CA (US); Nazila Habibizad, San Mateo, CA (US); Ali Komeyli, Pacifica, CA (US); DeMei Leung, Los Altos, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 15/782,381

(22) Filed: Oct. 12, 2017

(65) Prior Publication Data

US 2018/0125789 A1 May 10, 2018

Related U.S. Application Data

(60) Provisional application No. 62/553,716, filed on Sep. 1, 2017, provisional application No. 62/407,406, filed on Oct. 12, 2016.

(51) Int. Cl.
| | | |
|---|---|---|
| *A61K 9/20* | (2006.01) | |
| *A61K 31/4439* | (2006.01) | |
| *A61K 9/00* | (2006.01) | |
| *A61P 7/00* | (2006.01) | |
| *A61P 35/00* | (2006.01) | |
| *A61P 11/00* | (2006.01) | |
| *A61P 25/28* | (2006.01) | |
| *A61P 7/06* | (2006.01) | |

(52) U.S. Cl.
CPC .......... *A61K 9/2077* (2013.01); *A61K 9/0056* (2013.01); *A61K 9/2009* (2013.01); *A61K 9/2013* (2013.01); *A61K 9/2054* (2013.01); *A61K 31/4439* (2013.01); *A61P 7/00* (2018.01); *A61P 7/06* (2018.01); *A61P 11/00* (2018.01); *A61P 25/28* (2018.01); *A61P 35/00* (2018.01)

(58) Field of Classification Search
None
See application file for complete search history.

(56) References Cited

U.S. PATENT DOCUMENTS

| | | |
|---|---|---|
| 3,236,893 A | 2/1966 | Blout et al. |
| 4,062,858 A | 12/1977 | Hoehn et al. |
| 4,410,537 A | 10/1983 | Kneen |
| 4,478,834 A | 10/1984 | Shroff et al. |
| 4,535,183 A | 8/1985 | Kneen |
| 5,185,251 A | 2/1993 | Chen et al. |
| 5,202,243 A | 4/1993 | Balani |
| 5,266,582 A | 11/1993 | De Nanteuil et al. |
| 5,290,941 A | 3/1994 | Volante et al. |
| 5,403,816 A | 4/1995 | Takabe et al. |
| 5,521,202 A | 5/1996 | Yano et al. |
| 5,679,678 A | 10/1997 | Binder et al. |
| 5,681,567 A | 10/1997 | Martinez et al. |
| 5,760,232 A | 6/1998 | Chen et al. |
| 5,840,900 A | 11/1998 | Greenwald et al. |
| 5,880,131 A | 3/1999 | Greenwald et al. |
| 5,965,566 A | 10/1999 | Greenwald et al. |
| 5,994,353 A | 11/1999 | Breault |
| 6,011,042 A | 1/2000 | Greenwald et al. |
| 6,111,107 A | 8/2000 | Greenwald et al. |
| 6,127,355 A | 10/2000 | Greenwald et al. |
| 6,153,655 A | 10/2000 | Martinez et al. |
| 6,194,580 B1 | 2/2001 | Greenwald et al. |
| 6,214,817 B1 | 4/2001 | Riley et al. |
| 6,232,320 B1 | 5/2001 | Stewart et al. |
| 6,239,176 B1 | 5/2001 | Nudelman et al. |
| 6,242,644 B1 | 6/2001 | Ackermann et al. |
| 6,355,661 B1 | 3/2002 | Lai et al. |
| 6,395,266 B1 | 5/2002 | Martinez et al. |
| 6,472,349 B1 | 10/2002 | Hamprecht et al. |
| 6,593,472 B2 | 7/2003 | Hoffman et al. |
| 6,608,076 B1 | 8/2003 | Greenwald et al. |
| 6,627,646 B2 | 9/2003 | Bakale |
| 6,630,496 B1 | 10/2003 | Seehra et al. |
| 7,160,910 B2 | 1/2007 | Safo et al. |
| 7,411,083 B2 | 8/2008 | Gopalsamy et al. |
| 8,846,694 B2 | 9/2014 | Heinrich et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,150,569 B2 | 10/2015 | Fukuda et al. |
| 9,248,199 B2 | 2/2016 | Metcalf et al. |
| 9,422,279 B2 | 8/2016 | Metcalf et al. |
| 9,447,071 B2 * | 9/2016 | Li ..................... A61K 31/4439 |
| 9,458,139 B2 | 10/2016 | Xu et al. |
| 9,604,999 B2 | 3/2017 | Harris et al. |
| 9,776,960 B2 | 10/2017 | Xu et al. |
| 9,802,900 B2 | 10/2017 | Li et al. |
| 10,017,491 B2 | 7/2018 | Metcalf et al. |
| 10,034,879 B2 | 7/2018 | Metcalf et al. |
| 10,137,118 B2 | 11/2018 | Li et al. |

(Continued)

FOREIGN PATENT DOCUMENTS

| | | |
|---|---|---|
| CA | 2720096 | 10/2009 |
| CN | 101113148 | 1/2008 |

(Continued)

OTHER PUBLICATIONS

U.S. Appl. No. 61/581,053, filed Dec. 28, 2011, Metcalf et al.

(Continued)

*Primary Examiner* — Yong L Chu
(74) *Attorney, Agent, or Firm* — Sheppard Mullin Richter & Hampton LLP

(57) ABSTRACT

Provided herein are high strength/high drug load tablets comprising 2-hydroxy-6-((2-(1-isopropyl-1H-pyrazol-5-yl) pyridin-3-yl)methoxy)benzaldehyde ("Compound 1"), dispersible tablets comprising Compound 1, processes of manufacturing such tablets, and methods for treating patients with the tablets. Compound 1 is useful for treating hematological disorders such as sickle cell disease, pulmonary disease such as idiopathic pulmonary fibrosis, and hypoxia and hypoxemia conditions.

9 Claims, 2 Drawing Sheets

(56) References Cited

U.S. PATENT DOCUMENTS

| | | |
|---|---|---|
| 2001/0046997 A1 | 11/2001 | Abraham et al. |
| 2002/0095035 A1 | 7/2002 | Warshawsky et al. |
| 2002/0142995 A1 | 10/2002 | Nicolau et al. |
| 2002/0147138 A1 | 10/2002 | Firestone et al. |
| 2003/0022923 A1 | 1/2003 | Lai et al. |
| 2003/0060425 A1 | 3/2003 | Ahlem et al. |
| 2003/0073712 A1 | 4/2003 | Wang et al. |
| 2003/0165714 A1 | 9/2003 | Lee et al. |
| 2003/0187026 A1 | 10/2003 | Li et al. |
| 2003/0190333 A1 | 10/2003 | Mossman et al. |
| 2003/0199511 A1 | 10/2003 | Li et al. |
| 2004/0072796 A1 | 4/2004 | Embury et al. |
| 2004/0186077 A1 | 9/2004 | Diakur et al. |
| 2004/0209921 A1 | 10/2004 | Bridger et al. |
| 2005/0085484 A1 | 4/2005 | Mitchell et al. |
| 2005/0096337 A1 | 5/2005 | Ackermann et al. |
| 2005/0143420 A1 | 6/2005 | Moutouh-De Parseval et al. |
| 2005/0159605 A1 | 7/2005 | Tarur et al. |
| 2006/0094761 A1 | 5/2006 | Haque et al. |
| 2007/0213323 A1 | 9/2007 | Imogai et al. |
| 2007/0293698 A1 | 12/2007 | Quick et al. |
| 2008/0114167 A1 | 5/2008 | Castro et al. |
| 2009/0023709 A1 | 1/2009 | Gillespie et al. |
| 2009/0143371 A1 | 6/2009 | Buettelmann et al. |
| 2009/0163512 A1 | 6/2009 | Chen et al. |
| 2009/0312315 A1 | 12/2009 | Yamaguchi et al. |
| 2010/0048901 A1 | 2/2010 | Takahashi et al. |
| 2010/0204235 A1 | 8/2010 | Lizos et al. |
| 2010/0210651 A1 | 8/2010 | Hernandez et al. |
| 2010/0311748 A1 | 12/2010 | Dakin et al. |
| 2012/0220569 A1 | 8/2012 | Ohashi et al. |
| 2012/0245344 A1 | 9/2012 | Endo et al. |
| 2013/0045251 A1 | 2/2013 | Cen et al. |
| 2013/0072472 A1 | 3/2013 | Gless et al. |
| 2013/0190315 A1 | 7/2013 | Metcalf et al. |
| 2013/0190316 A1 | 7/2013 | Metcalf et al. |
| 2013/0190375 A1 | 7/2013 | Dunkel et al. |
| 2013/0273157 A1* | 10/2013 | Ishii .............. A61K 9/0056 424/465 |
| 2014/0004184 A1 | 1/2014 | Ashraf et al. |
| 2014/0142149 A1* | 5/2014 | Zhang ............ A61K 9/2013 514/380 |
| 2014/0271591 A1 | 9/2014 | Sinha et al. |
| 2014/0274961 A1 | 9/2014 | Metcalf et al. |
| 2014/0275152 A1 | 9/2014 | Metcalf et al. |
| 2014/0275176 A1 | 9/2014 | Xu et al. |
| 2014/0275181 A1 | 9/2014 | Harris et al. |
| 2015/0057251 A1 | 2/2015 | Harris |
| 2015/0133430 A1 | 5/2015 | Xu et al. |
| 2015/0141465 A1 | 5/2015 | Yee et al. |
| 2015/0225366 A1* | 8/2015 | Li .............. A61K 31/4439 514/341 |
| 2015/0259296 A1 | 9/2015 | Li et al. |
| 2015/0336908 A1 | 11/2015 | Shioda et al. |
| 2015/0344472 A1 | 12/2015 | Metcalf et al. |
| 2015/0344483 A1 | 12/2015 | Metcalf et al. |
| 2016/0024127 A1 | 1/2016 | Harris et al. |
| 2016/0031865 A1 | 2/2016 | Li et al. |
| 2016/0031904 A1 | 2/2016 | Li et al. |
| 2016/0038474 A1 | 2/2016 | Sinha et al. |
| 2016/0039801 A1 | 2/2016 | Metcalf et al. |
| 2016/0046613 A1 | 2/2016 | Metcalf et al. |
| 2016/0083343 A1 | 3/2016 | Xu et al. |
| 2016/0303099 A1 | 3/2016 | Dufu et al. |
| 2016/0152602 A1 | 6/2016 | Xu et al. |
| 2016/0206604 A1 | 7/2016 | Metcalf et al. |
| 2016/0206614 A1 | 7/2016 | Metcalf et al. |
| 2016/0207904 A1 | 7/2016 | Li et al. |
| 2016/0332984 A1 | 11/2016 | Metcalf et al. |
| 2016/0346263 A1 | 12/2016 | Li et al. |
| 2017/0107199 A1 | 4/2017 | Metcalf et al. |
| 2017/0157101 A1 | 6/2017 | Ramos et al. |
| 2017/0174654 A1 | 6/2017 | Metcalf et al. |
| 2017/0327484 A1 | 11/2017 | Li et al. |
| 2017/0355713 A1 | 12/2017 | Harris et al. |
| 2018/0186807 A1 | 7/2018 | Yee et al. |
| 2018/0201577 A1 | 7/2018 | Xu et al. |
| 2018/0354929 A1 | 12/2018 | Metcalf et al. |
| 2019/0010121 A1 | 1/2019 | Xu et al. |
| 2019/0010176 A1 | 1/2019 | Harris |
| 2019/0106404 A1 | 4/2019 | Li et al. |
| 2019/0111037 A1 | 4/2019 | Li et al. |
| 2019/0112287 A1 | 4/2019 | Metcalf et al. |
| 2019/0160060 A1 | 5/2019 | Metcalf et al. |

FOREIGN PATENT DOCUMENTS

| | | |
|---|---|---|
| CN | 102116772 | 7/2011 |
| DE | 2238734 | 2/1973 |
| DE | 2238628 | 3/1973 |
| DE | 2853765 | 6/1980 |
| DE | 2904829 | 8/1980 |
| DE | 226590 | 8/1985 |
| DE | 3503435 | 8/1985 |
| DE | 3431004 | 3/1986 |
| DE | 3704223 | 8/1987 |
| DE | 258226 | 7/1988 |
| DE | 276479 | 2/1990 |
| DE | 276480 | 2/1990 |
| DE | 3931954 | 3/1990 |
| DE | 4318550 | 12/1994 |
| DE | 4442050 | 5/1996 |
| EP | 010063 | 4/1980 |
| EP | 0054924 | 6/1982 |
| EP | 236140 | 9/1987 |
| EP | 0268989 | 6/1988 |
| EP | 0278686 | 8/1988 |
| EP | 0291916 | 11/1988 |
| EP | 0303465 | 2/1989 |
| EP | 0336369 | 10/1989 |
| EP | 0348155 | 12/1989 |
| EP | 0365328 | 4/1990 |
| EP | 0401517 | 12/1990 |
| EP | 0453210 | 10/1991 |
| EP | 0462800 | 12/1991 |
| EP | 0481802 | 4/1992 |
| EP | 0498380 | 8/1992 |
| EP | 0528337 | 2/1993 |
| EP | 0542372 | 5/1993 |
| EP | 0567133 | 10/1993 |
| EP | 0632036 | 1/1995 |
| EP | 0637586 | 2/1995 |
| EP | 0640609 | 3/1995 |
| EP | 0747393 | 12/1996 |
| EP | 2123637 | 11/2009 |
| EP | 2149545 | 3/2010 |
| EP | 2305625 | 6/2011 |
| FR | 2217016 | 1/1900 |
| FR | 2909379 | 6/2008 |
| GB | 1409865 | 10/1975 |
| GB | 1593417 | 7/1981 |
| IL | 64573 | 4/1985 |
| JP | 57-145844 | 6/1905 |
| JP | 59029667 | 2/1984 |
| JP | 61-040236 | 2/1986 |
| JP | 63230687 | 9/1988 |
| JP | S-63258463 | 10/1988 |
| JP | 01190688 | 7/1989 |
| JP | 06-041118 | 2/1994 |
| JP | 07-025882 | 1/1995 |
| JP | 2002-523469 | 7/2002 |
| JP | 2002-528537 | 9/2002 |
| JP | 2003-075970 | 3/2003 |
| JP | 2003-513060 | 4/2003 |
| JP | 2006-342115 | 12/2006 |
| JP | 2009-203230 | 9/2009 |
| WO | WO-91/19697 | 12/1991 |
| WO | WO-92/02503 | 2/1992 |
| WO | WO-93/17013 | 9/1993 |
| WO | WO-94/01406 | 1/1994 |
| WO | WO-95/14015 | 5/1995 |
| WO | WO-95/21854 | 8/1995 |
| WO | WO-96/11902 | 4/1996 |
| WO | WO-97/41120 | 11/1997 |

(56) References Cited

FOREIGN PATENT DOCUMENTS

| WO | WO-97/44306 | 11/1997 |
|---|---|---|
| WO | WO-98/08818 | 3/1998 |
| WO | WO-98/21199 | 5/1998 |
| WO | WO-99/29694 | 6/1999 |
| WO | WO-99/43672 | 9/1999 |
| WO | WO-99/47529 | 9/1999 |
| WO | WO-99/48490 | 9/1999 |
| WO | WO-99/59978 | 11/1999 |
| WO | WO-99/62908 | 12/1999 |
| WO | WO-00/12121 | 3/2000 |
| WO | WO-00/26202 | 5/2000 |
| WO | WO-00/35858 | 6/2000 |
| WO | WO-00/40564 | 7/2000 |
| WO | WO-00/71123 A1 | 11/2000 |
| WO | WO-00/75145 | 12/2000 |
| WO | WO-00/78746 | 12/2000 |
| WO | WO-01/00612 | 1/2001 |
| WO | WO-01/19823 | 3/2001 |
| WO | WO-01/23383 | 4/2001 |
| WO | WO-01/32596 | 5/2001 |
| WO | WO-01/36375 | 5/2001 |
| WO | WO-01/57006 | 8/2001 |
| WO | WO-01/57044 | 8/2001 |
| WO | WO-01/62705 | 8/2001 |
| WO | WO-01/70663 | 9/2001 |
| WO | WO-02/00622 | 1/2002 |
| WO | WO-02/12235 | 2/2002 |
| WO | WO-02/24635 | 3/2002 |
| WO | WO-02/24679 | 3/2002 |
| WO | WO-02/051849 | 7/2002 |
| WO | WO-02/053547 | 7/2002 |
| WO | WO-03/051366 | 6/2003 |
| WO | WO-03/053368 | 7/2003 |
| WO | WO-03/101959 | 12/2003 |
| WO | WO-2004/014899 | 2/2004 |
| WO | WO-2004/018430 | 3/2004 |
| WO | WO-2004/024705 | 3/2004 |
| WO | WO-2004/050030 | 6/2004 |
| WO | WO-2004/056727 | 7/2004 |
| WO | WO-2004/058790 | 7/2004 |
| WO | WO 2004/073675 | 9/2004 |
| WO | WO-2004/087075 | 10/2004 |
| WO | WO-2004/111031 | 12/2004 |
| WO | WO-2005/047249 | 5/2005 |
| WO | WO-2005/074513 | 8/2005 |
| WO | WO-2005/077932 | 8/2005 |
| WO | WO-2005/086951 | 9/2005 |
| WO | WO-2005/087766 | 9/2005 |
| WO | WO-2005/096337 | 10/2005 |
| WO | WO-2006/011469 | 2/2006 |
| WO | WO-2006/065204 | 6/2006 |
| WO | WO-2006/088173 | 8/2006 |
| WO | WO-2006/103463 | 10/2006 |
| WO | WO-2006/106711 | 10/2006 |
| WO | WO-2006/116764 | 11/2006 |
| WO | WO-2006/003923 | 12/2006 |
| WO | WO-2007/003962 | 1/2007 |
| WO | WO-2007/009389 | 1/2007 |
| WO | WO-2007/017267 | 2/2007 |
| WO | WO-2007/047204 | 4/2007 |
| WO | WO-2007/049675 | 5/2007 |
| WO | WO-2007/061923 | 5/2007 |
| WO | WO-2007/084914 | 7/2007 |
| WO | WO-2007/117180 | 10/2007 |
| WO | WO 2008/012495 | 1/2008 |
| WO | WO-2008/013414 | 1/2008 |
| WO | WO-2008/016132 | 2/2008 |
| WO | WO-2008/029200 | 3/2008 |
| WO | WO-2008/041118 | 4/2008 |
| WO | WO-2008/051532 | 5/2008 |
| WO | WO-2008/060391 | 5/2008 |
| WO | WO-2008/066145 | 6/2008 |
| WO | WO-2008/081096 | 7/2008 |
| WO | WO-2008/101682 | 8/2008 |
| WO | WO-2008/116620 | 10/2008 |
| WO | WO-2009/001214 | 12/2008 |
| WO | WO-2009/011850 | 1/2009 |
| WO | WO-2009/050183 | 4/2009 |
| WO | WO-2009/125606 | 10/2009 |
| WO | WO-2009/128537 | 10/2009 |
| WO | WO-2009/130560 | 10/2009 |
| WO | WO-2009/136889 | 11/2009 |
| WO | WO-2009/146555 | 12/2009 |
| WO | WO-2010/031589 | 3/2010 |
| WO | WO-2010/056631 | 5/2010 |
| WO | WO-2010/129055 | 11/2010 |
| WO | WO-2011/033045 | 3/2011 |
| WO | WO-2011/088201 | 7/2011 |
| WO | WO-2011/136459 | 11/2011 |
| WO | WO-2012/020060 | 2/2012 |
| WO | WO-2012/138981 | 10/2012 |
| WO | WO-2012/141228 | 10/2012 |
| WO | WO-2013/052803 | 4/2013 |
| WO | WO-2013/102142 | 7/2013 |
| WO | WO-2013/102145 | 7/2013 |
| WO | WO-2014/104384 | 7/2014 |
| WO | WO-2014/150256 | 9/2014 |
| WO | WO-2014/150258 | 9/2014 |
| WO | WO-2014/150261 | 9/2014 |
| WO | WO-2014/150268 | 9/2014 |
| WO | WO-2014/150276 | 9/2014 |
| WO | WO-2014/150289 | 9/2014 |
| WO | WO-2015/031284 | 3/2015 |
| WO | WO-2015/031285 | 3/2015 |
| WO | WO 2015/120133 | 8/2015 |
| WO | WO 2016/160755 | 10/2016 |
| WO | WO 2017/096230 | 6/2017 |

OTHER PUBLICATIONS

U.S. Appl. No. 61/661,320, filed Jun. 18, 2012, Metcalf et al.
"Master of Engineering Education Chemical Engineering Development Report" National Engineering Education Master in Chemical Engineering Cooperation Group, Zhejiang University Press. Mar. 31, 2011; 241-245. (in Chinese with English abstract).
Abdulmalik et al., "Crystallographic analysis of human hemoglobin elucidates the structural basis of the potent and dual antisickling activity of pyridyl derivatives of vanillin", Acta Cryst. 2011, D67, 920-928.
Abdulmalik et al., Sickle cell disease: current therapeutic approaches, Expert Opinion Ther. Patents, 2005, vol. 15(11), pp. 1497-1506.
Abraham et al., Vanillin, a Potential Agent for the Treatment of Sickle Cell Anemia, Blood, Mar. 1991, vol. 77 (6), pp. 1334-1341.
Adhikary, P.K., et al., "A new antisickling agent: In vitro studies of its effect on S/S erythrocytes and on hemoglobin S", Experientia. 1978, vol. 34, No. 6, pp. 804-806.
Appendix A provided with Israel office action dated Aug. 11, 2016 for IL 233329.
Arya R, et al. "Tucaresol increases oxygen affinity and reduces haemolysis in subjects with sickle cell anaemia," Br. J. Haematol., 93(4):817-21 (1996).
Australian Examination Report dated Nov. 7, 2016 for AU 2016203755.
Babu, et al. Regioselective synthesis and structural elucidation of 1,4-disubstituted 1,2,3-triazole derivatives using 1D and 2D NMR spectral techniques. Magn. Reson. Chem., 2011; 49: 824-829. doi:10.1002/mrc.2820.
Bacsa et al., "Novel products from Baylis-Hillman reactions of salicylaldehydes", South African Journal of Chemistry (1998), 51(1), 47-54 CODEN: SAJCDG; ISSN: 0379-4350.
Ballerini et al., High pressure Diels-Alder approach to hydroxy-substituted 6a-cyano-tetrahydro-6H-benzo[c]chromen-6-ones: A route to Δ6-Cis-Cannabidiol. J.Org.Chem., 74(11):4311-4317, 2009.
Ballet et al., Novel selective human melanocortin-3 receptor ligands: Use of the 4-amino-1,2,4,5-tetrahydro-2-benzazepin-3-one (Aba) scaffold, Bioorganic & Medicinal Chemistry Letters (2007), 17(9), 2492-2498 CODEN: BMCLES; ISSN: 0960-894X.
Barnes, et al., "Prospects for new drugs for chronic obstructive pulmonary disease." The Lancet, 2004, 364, 985-996.
Barnes. "COPD: is there light at the end of the tunnel?" Current Opinion in Pharmacology, 2004, 4:263-272.

(56) References Cited

OTHER PUBLICATIONS

Baxter et al., "Reductive aminations of carbonyl compounds with borohydride and borane reducing agents", Organic Reactions (Hoboken, NJ, United States) (2002), 59, No pp. given bin/mrwhome/107610747/HOME.
Beaumont et al., Design of ester prodrugs to enhance oral absorption of poorly permeable compounds: challenges to the discovery scientist. Curr. Drug Metab. 2003, 4:461-85.
Beddell, Substituted benzaldehydes designed to increase the oxygen affinity of human haemoglobin and inhibit the sickling of sickle erythrocycles, Br. J. Pharmac., 82:397-407, 1984.
Beena et al., "Synthesis and antibacterial activity evaluation of metronidazole-triazole conjugates", Bioorganic & Medicinal Chemistry Letters, 2009, 19(5):1396-1398.
Behanna. Equity Research—Global Blood Therapeutics. Sep. 8, 2015. Retrieved from the Internet: URL:http://www.fintechsecurities.com/Websites/fintechsecurities/images/Research_Blog/Zacks/Sep2015/GBT150908.pdf.
Berge et al., "Pharmaceutical Salts", Journal of Pharmaceutical Science, 1977, 66:1-19.
Bernstein. Crystals in Supramolecular Chemistry. ACA Transactions. 2004; 39:1-14.
Bernstein. Polymorphism in Molecular Crystals. Clarendon Press, Oxford. 2002. 115-118, 272.
Bode et al., "Novel synthesis and x-ray crystal structure of a coumarin derivative", South African Journal of Chemistry (1992), 45(1), 25-7 CODEN: SAJCDG; ISSN:0379-4350.
Bonaventura, et al., "Molecular Controls of the Oxygenation and Redox Reactions of Hemoglobin." Antioxidants & Redox Signaling, 18(17), 2013, 2298-2313.
Bottino, et al. Study on the scope of tert-amino effect: new extensions of type 2 reactions to bridged biaryls. J. Phys. Org. Chem. 2012; 25(11):1033-1041.
Bradbury et al., "New nonpeptide angiotensin II receptor antagonists", Journal of Medicinal Chemistry, 1993, vol. 36, pp. 1245-1254.
Braga, et al. Making crystals from crystals: a green route to crystal engineering and polymorphism. Chem Commun (Camb). Aug. 7, 2005;(29):3635-45. Epub Jun. 15, 2005.
Britton et al., "Structure-activity relationships of a series of benzothlophens-derived NPY Y1 antagonists: optimization of the C-2 side chain". Bioorganic & Medicinal Chemistry Letters (1999), 9(3), 475-480 CODEN:BMCLE8;ISSN: 0960-894X.
Brown et al., "1,2-Dihydroisoquinollnes. III, Dimerization", Tetrahedron (1966), 22(8), 2437-43 CODEN: TETRAB; ISSN;0040-4020.
Caira. Crystalline Polymorphism of Organic Compounds. Topics in Current Chemistry, Springer, Berlin, DE. 1998; 198:163-208.
CAS Registry No. 1039841-20-7; entry dated Aug. 10, 2008.
CAS Registry No. 1096911-11-3; entry dated Jan. 28, 2009.
CAS Registry No. 1153166-41-6; entry dated Jun. 7, 2009.
CAS Registry No. 1153961-01-3; entry dated Jun. 8, 2009.
CAS Registry No. 1184809-65-1; entry dated Sep. 15, 2009.
CAS Registry No. 1303782-57-1; entry dated Jun. 1, 2011.
CAS Registry No. 1306264-96-9; entry dated Jun. 5, 2011.
CAS Registry No. 631858-40-7; entry dated Dec. 29, 2003.
Chemical Abstract Registry No. 1142191-55-6, indexed in the Registry File on STN CA Online May 4, 2009.
Cheng, et al. Vilsmeier formylation of tert-anilines: dibenzo[b,f][1,5]diazocines and quinazolinium salts via the 't-amino effect'. J. Chem. Soc., Perkin Trans 1. 1998; 1257-1262.
Cherian et al., "Structure-Activity Relationships of Antitubercular Nitroimidazoles 3. Exploration of the Linker and Lipophilic Tail of ((S)-2-Nitro-6,7-dihydro-5H-imidazo[2,1-b][1,3]oxazin-6-yl)-(4-trifluoromethoxybenzyl)amine (6-Amino PA-824).," J. Med. Chem., Aug. 2011, vol. 54(16), pp. 5639-5659.
Ciganek, "The catalyzed a-hydroxyalkylation and a-aminoalkylation of activated olefins (the Morita-Baylis-Hillman reaction", Organic Reactions (Hoboken, NJ, United States) (1997), 51, No pp given CODEN:ORHNBA URL:http://www3.Interscience.wiley.com/cgi-bin/mnwhome/107610747/HOME.

CMU Pharmaceutical polymorphism, internet p. 1-3 (2002) printout Apr. 3, 2008.
Concise Encyclopedia Chemistry, NY: Walter de Gruyter, 1993, 872-873.
Congreve et al. Application of Fragment Screening by X-ray Crystallography to the Discovery of Aminopyridines as Inhibitors of Beta-Secretase. J. Med. Chem. 50:1124-1132 (2007).
Cos et al., "Structure-Activity Relationship and Classification of Flavonoids as Inhibitors of Xanthine Oxidase and Superoxide Scavengers," J. Nat. Prod., (1998), 61:71-76.
Database CA Chemical Abstract Service, Li et al., "Substituted-benzoheterocycle derivatives, preparation, and application for preparation of antiviral or antineoplastic drugs," XP002726578 retrieved from STN Database accession No. 2013:366779 (abstract); RN:1427163-92-5 & CN 102 952 062 A, Mar. 6, 2013, 2 pages.
Database Pubchem Compound Dec. 4, 2011 XP 003033770 (11 pages).
Database Registry, 2011, RN 1289869-72-2, 1027970-95-1, 959671-57-9.
Database Registry, 2012, RN 1390863-18-9, 1390573-58-6, 1389652-57-6, 1387166-17-7, 1318517-26-8, 1318395-05-9, 933829-46-0, 879919-21-8.
Davidovich, et al. Detection of polymorphism by powder x-ray diffraction: interference by preferred orientation. Am. Pharm. Rev. 2004; 10, 12, 14, 16, 100.
Dean. Analytical Chemistry Handbook. University of Tennesse, Knoxville. McGraw-Hill, Inc. 1995; 10.24-10.26.
Deem. "Red Blood Cells and Hemoglobin in Hypoxic Pulmonary Vasoconstriction" Advances in experimental medicine and biology, (2006) 588, 217-231.
Desai et al. Preparation of N-[ro-(4-aryl-1-piperazinyl)ethyl/propyl]-3-hydroxyphthalimidines. Indian Journal of Chemistry. 39:455-457 (2000).
Desideri et al., "Guanylhydrazones of 3-substituted 2-pyridinecarboxaldehyde and of (2-substituted 3-pyridinyloxy) acetaldehyde as prostanoid biosynthesis and platelet aggregation inhibitors", European Journal of Medicinal Chemistry, Editions Scientifique Elsevier, Paris, FR, 1991, vol. 26, No. 4, pp. 455-460.
Di Stilo, et al. New 1,4-dihydropyridines conjugated to furoxanyl moieties, endowed with both nitric oxide-like and calcium channel antagonist vasodilator activities. J. Med. Chem. 41:5393-5401 (1998).
Ding et al., "Crystal structure of bis[μ2-2-(2-formylphenoxy)acetato-O,O]-bis[μ2-2-2-formylphynoxy)acetato-O,O]-octakis(n-butyl)tetratin(IV), Sn4O2(C9H7O4)4(C4H9)8", Zeitschrift fuer Kristallographie—New Crystal Structures (2011), 226(1), 31-32 CODEN:ZKNSFT; ISSN: 1433-7266.
Doelker, English translation of S.T.P, Pratiques (1999), 9(5), 399-409.
Doelker. English translation of Ann. Pharm. Fr., 2002, 60: 161-176.
Einfalt, et al. Methods of amorphization and investigation of the amorphous state. Acta Pharm. 2013; 63:305-334.
Elwahy, "Synthesis of new benzo-substituted macrocyclic containing quinoxaline subunits" Tetrahedron (2000), 56(6), 897-907 CODEN:TETRAB; ISSN:0040-4020.
Epsztajn et al., "Application of organolithium", Tetrahedron, Elsevier Science Publishers, Amsterdam, NL, 1991, vol. 47, No. 9, pp. 1697-1706.
European Search Report and Search Opinion dated Aug. 4, 2015 for EP Application No. 12862525.8. 9 pages.
European Search Report and Search Opinion dated Jul. 21, 2016 for EP Application No. 14769616.5. 8 pages.
European Search Report and Search Opinion dated May 28, 2015 for EP Application No. 12862096.0. 13 pages.
European Search Report and Search Opinion dated Nov. 16, 2016 for EP Application No. 16194019.2. 13 pages.
European Search Report and Search Opinion dated Sep. 26, 2016 for EP Application No. 14768759.4. 6 pages.
Extended European Search Report and opinion dated Jul. 20, 2016 for EP Application No. 14768414.6. 10 pages.
Extended European Search Report and Search Opinion dated Jul. 18, 2016 for EP Application No. 14770695.6. 13 pages.
Extended European Search Report and Search Opinion dated Jul. 7, 2016 for EP Application No. 14768317.1. 7 pages.

(56) References Cited

OTHER PUBLICATIONS

Extended European Search Report and Search Opinion dated May 17, 2017 for EP Application No. 15746995.8. 8 pages.
Extended European Search Report and Search Opinion dated Nov. 23, 2015 for EP Application No. 12862525.8. 16 pages.
Gadaginamath, et al., "Synthesis and antibacterial activity of novel 1-butyl-2-phenoxyl2-phenylthlol2-aminomethyl-5-methoxyindole derivatives", Polish Journal of Chemistry (1997), 71(7), 923-928 CODEN: PJCHDQ; ISSN:0137-5083.
Gao et al, "A novel one-pot three-step synthesis of 2-(1-benzofuran-2-yl)quinoline-3-carboxylic acid derivatives", Journal of the Brazilian Chemical Society (2010), 21(5). 806-812 CODEN:JOCSET; ISSN: 0103-5053.
Ghate et al., "Synthesis of vanillin ethers from 4-(bromomethyl) coumarins as anti-inflammatory agents, "European Journal of Medicinal Chemistry (2003), 38(3), 297-302 CODEN: EJMCAS; ISSN: 0223-5234.
Gibson et al., "Novel small molecule bradykinin B2 receptor antagonists", Journal of Medicinal Chemistry, 2009, vol. 52, pp. 4370-4379.
Glasson et al. Metal Template Synthesis of a Tripodal Tris(bipyridyl) Receptor that Encapsulates a Proton and an Iron (ii) Centre in a Pseudo Cage. Aust. J. Chem. 65:1371-1376 (2012).
Grashey, "The nitro group as a 1,3-dipole in cycloadditions" Angewandte Chemie (1962), 74, 155 CODEN: ANCEAD; ISSN: 0044-8249.
Guillaumel, et al. Synthetic routes to 2-(2-benzofuranyl)benzoic acids and their cyclization into benz[6]indeno[2,1-d]furan-10-ones. Journal of Heterocyclic Chemistry, 1990; 27: 1047-1051. doi:10.1002/jhet.5570270444.
Guillory (in Brittain ed.) Polymorphism in Pharmaceutical Solids. NY, Marcel Dekker, Inc. 1999; 1-2:183-226.
Gunter et al., "Structural control of co-receptor binding in porphyrin-bipyridinium supramolecular assemblies", Journal of the Chemical Society, Perkin Transactions 1: Organic and Bio-Organic Chemistry (1998), (12), 1945-1958 CODEN: JCPRB4; ISSN: 0300-922X.
Hang, Song. "Pharmaceutical Separation Engineering" East China University of Technology Press. Aug. 31, 2011; 270-272. (in Chinese with English abstract).
Hanmantgad et al., "Synthesis and pharmacological properties of some r-(2-benzo[b]furanyl)coumarins" Indian Journal of Chemistry, Section B: Organic Chemistry Including Medicinal Chemistry (1986), 25B(7), 779-81 CODEN: IJSBDB; ISSN: 0376-4699.
He et al., "Prodrugs of Phosphonates, Phosphinates, and Phosphates", Prodrugs: Challenges and rewards Part 2, edited by Stella et al., 2007, pp. 223-264.
Heimbach et al., "Enzyme-mediated precipitation of patent drugs from their phosphate prodrugs", International Journal of Pharmaceutics, 261, p. 81-92, 2003.
Heimbach et al., "Prodrugs: Challenges and Rewards Part I," New York, NY, Singer:AAPS Press, (2007), 5(Chapter 2.2.1):157-215 Overcoming Poor Aqueous Solubility of Drugs for Oral Delivery.
Heimgartner et al., "Stereoselective synthesis of swainsonines from pyridines", Tetrahedron, Elsevier Science Publishers, Amsterdam, NL, 2005, vol. 61, No. 3, pp. 643-655.
Hoffman, et al. 3-Hydroxy-3-methylglutaryl-coenzyme A Reductase Inhibitors, 2. Structural Modification of 7-(Substituted aryl)-3,5-dihydroxy-6-heptenoic Acids and Their Lactone Derivatives. Journal of Medical Chemistry. 29(2):159-169 (1986).
Hong et al., "Potential Anticancer Agents VI: 5-Substituted Pyrimidine-6-Carboxaldehydes", Journal of Pharmaceutical Sciences, American Pharmaceutical Association, Washington, US, 1970, vol. 59, No. 11, pp. 1637-1645.
Huckauf, et al., "Oxygen Affinity of Haemoglobin and Red Cell Acid-Base Status in Patients with Severe Chronic Obstructive Lung Disease" Bull. Europe Physiopath. Resp., 1976, 12, 129-142.
International Preliminary Report on Patentability for PCT/US2014/022846 dated Sep. 15, 2015. 7 pages.
International Preliminary Report on Patentability for PCT/US2014/022742 dated Sep. 15, 2015. 7 pages.
International Preliminary Report on Patentability for PCT/US2014/022733 dated Sep. 15, 2015. 11 pages.
International Preliminary Report on Patentability for PCT/US2014/022769 dated Sep. 15, 2015. 8 pages.
International Search Report and Written Opinion dated Aug. 19, 2014 for PCT Application No. PCT/US2014/022736. 14 pages.
International Search Report and Written Opinion dated Aug. 27, 2014 for PCT Application No. PCT/US2014/022742. 11 pages.
International Search Report and Written Opinion dated Aug. 4, 2017 for PCT Application No. PCT/US2017/032104. 10 pages.
International Search Report and Written Opinion dated Dec. 8, 2014 for PCT Application No. PCT/US2014/052575. 10 pages.
International Search Report and Written Opinion dated Jan. 22, 2018 for PCT Application No. PCT/US2017/056352. 12 pages.
International Search Report and Written Opinion dated Jul. 22, 2014 for PCT Application No. PCT/US2014/022846. 11 pages.
International Search Report and Written Opinion dated Jul. 30, 2014 for PCT Application No. PCT/US2014/029682. 16 pages.
International Search Report and Written Opinion dated Jul. 31, 2014 for PCT Application No. PCT/US2014/022789. 13 pages.
International Search Report and Written Opinion dated Jul. 4, 2014 for PCT Application No. PCT/US2014/022769. 11 pages.
International Search Report and Written Opinion dated Mar. 5, 2013 for PCT Application No. PCT/US2012/072177. 7 pages.
International Search Report and Written Opinion dated May 11, 2015 for PCT Application No. PCT/US2015/014589. 5 pages.
International Search Report and Written Opinion dated May 20, 2013 for PCT Application No. PCT/US2012/072183. 11 pages.
International Search Report and Written Opinion dated Nov. 28, 2014 for PCT Application No. PCT/US2014/052576. 10 pages.
International Search Report and Written Opinion dated Oct. 31, 2014 for PCT Application No. PCT/US2014/013575. 10 pages.
Israel office action dated Aug. 11, 2016 for Israeli Patent Application No. 233329.
Ito et al., A medium-term rat liver bioassay for rapid in vivo detection of carcinogenic potential of chemicals,01D Cancer Science, Jan. 2003, 94, pp. 3-8.
Ivanisevic, et al. Uses of x-ray powder diffraction in the pharmaceutical industry. Pharm. Sci. Encycl. 2010; 1-42.
Jain, et al., "Polymorphism in Pharmacy", Indian Drugs, 1986, 23(6) 315-329.
Jarvest et al., "Discovery and optimisation of potent, selective, ethanolamine Inhibitors of bacterial phenylalanyl tRNA synthetase", Bioorganic & Medicinal Chemistry Letter (2005), 15(9), 2305-2309 CODEN: BMCLES; ISSN: 0960-894X.
Karche et al., "Electronic Effects in Migratory Groups [1,4]—versus [1,2]—Rearrangement in Rhodium Carbenoid Generated Bicyclic Oxonium Ylides", Journal of Organic Chemistry (2001), 66(19), 6323-6332 CODEN: JOCEAH; ISSN: 0022-3263.
Katritzky et al., "Syntheses of 3-hydroxymethyl-2-3-dihydrobenzofurans and 3-hydroxymethylbenzofurans", ARKIVOC (Gainesville, FL, United States) (2003), (6), 49-61 CODEN: AGFUAR URL: http://www.arkat-usa.org/ark/journal/2003/Vargoglis/AV-622A/6ss.pdf.
Kaye et al., "DABCO-catalyzed reactions of salicylaldehydes with acrylate derivatives", Synthetic Communications (1996), 26(11), 2085-97 CODEN: SYNCAV; ISSN: 0039-7911.
Kaye et al., "Does the DABCO-catalyzed reaction of 2-hydroxybenzaldehydes with methyl acrylate follow a Baylis-Hillman pathway?", Organic & Biomolecular Chemistry (2003), 1(7), 1133-1138 CODEN: OBCRAK; ISSN: 1477-0520.
Keidan, et al. Effect of BW12C on oxygen affinity of hemoglobin in sickle-cell disease. The Lancet. 1986; 327(8485):831-834.
Kessar et al., "Synthesis of Isoindolobenzazepines via photocyclisation of N-(2-formylphenethyl)phthalimide derivatives", Indian Journal of Chemistry, Section B: Organic Chemistry Including Medicinal Chemistry (1991), 30B(11), 999-1005 CODEN: JSBDB; ISSN:3076-4699.
Kessar et al., An Interesting Application of Photocyclisation in Apophdeadane Alkaloid Synthesis. Tetrahedron Letters (1987), 28(44), 5323-5326. CODEN: TELEAY; ISSN: 0040-4039.
Kirk-Othmer Encyclopedia of Chemical Technology. 2002; 8:95-147.

(56) References Cited

OTHER PUBLICATIONS

Kise et al., "Electroreductive Intramolecular Coupling of Phthalimides with Aromatic Aldehydes: Application to the Synthesis of Lennoxamine". Journal of Organic Chemistry (2011), 76(23), 9856-9880 CODEN:JOCEAH; ISSN: 0022-3263.

Klis, et al. Halogen-lithium exchange versus deprotonation: synthesis of diboronic acids derived from aryl-benzyl ethers. Tetrahedron Letters, 48(7):1169-1173 (2007).

Kratochvil. Chapter 8 Solid Forms of Pharmaceutical Molecules. J. Sestak et al. (eds.), Glassy, Amorphous and Nano-Crystalline Materials. Hot Topics in Thermal Analysis and Calorimetry 8, 2011, pp. 129-140.

Kraus, et al. Michael additions in anhydrous media. A novel synthesis of oxygenated coumarins. J. Org. Chem., 1979, 44 (14), pp. 2480-2482.

Krow,"The Baeyer-Villiger oxidation of ketones and aldehydes", Organic Reactions (Hoboken, NJ, United States) (1993), 43, No pp. given CODEN: ORHNBA URL: http://www3.interscience.wiley.com/cgi-bin/mrwhome/107610747/HOME.

Kucera, et al. Evaluation of Ceolus(TM) microcrystalline cellulose grades for the direct compression of enteric-coated pellets. Drug Development and Industrial Pharmacy. Mar. 1, 2012; 38(3):341-350.

Lakkannavar et al., "4-[2'-benzylideneanlino arylownethyl] coumarins E and Z isomers". Indian Journal of Heterocyclic Chemistry (1995), 4(4), 303-4 CODEN: IJCHEI; ISSN: 0971-1627.

Lin et al. Synthesis and anticancer activity of benzyloxybenzaldehyde derivatives against HL-60 cells. Bioorganic & Medicinal Chemistry. 13(5), 1537-1544 (2005).

Lin et al., "Potential Antitumor Agents.8. Derivatives of 3- and 5-Benzyloxy-2-formylpyridine Thiosemicarbazone", Journal of Medicinal Chemistry, American Chemical Society, US, 1972, vol. 15, No. 6, pp. 615-618.

Liu et al., "Synthesis of Double-Armed Benzo-15-crown-5 and Their Complexation Thermodynamics with Alkali Cations", Journal of Inclusion Phenomena and Macrocyclic Chemistry (2005), 52(3-4), 229-235 CODEN: JIPCF5; ISSN: 1388-3127.

Luan, et al. Tops-Mode model of multiplexing neuroprotective effects of drugs and experimental-theoretic study of new 1,3-rasagiline derivatives potentially useful in neurodegenerative diseases. Bioorganic & Medicinal Chemistry. 2013; 21:1870-1879.

Mahoney et al., "Functionalization of Csp3-H bond-Sc(OTf)3-catalyzed domino 1,5-hydride shift/cyclization/Friedel-Crafts acylation reaction of benzylidene Meldrum's acids", Tetrahedron Letters (2009), 50(33), 4706-4709 CODEN: TELEAY; ISSN: 0040-4039.

Majhi et al., "An efficient synthesis of novel dibenzo-fused nine-membered oxacycles using a sequential Baylis-Hillman reaction and radical cyclization", Synthesis (2008), (1), 94-100 CODEN: SYNTBF; ISSN: 0039-7881.

Manna et al., Synthesis and beta-adrenoreceptor blocking activity of [[3-(alkylamine)-2-hydroxypropyl]oximino]pyridines and 0[3-(alkylamine)-2-hydroxypropyl]methylpyridine ketone oximes derivatives, IL Farmaco, 1996, vol. 51, No. 8, 9, pp. 579-587.

Mantyla et al., Synthesis, in vitro evaluation, and antileishmanial activity of water-soluble prodrugs of buparvaquone. J. Med. Chem. 2004, 47:188-195.

Marchetti et al., "Synthesis and biological evaluation of 5-substituted O4-alkylpyrimidines as CDK2 inhibitors," Org. Biomol. Chem, 2010, vol. 8, pp. 2397-2407.

Mathur. "Microcrystalline Cellulose" In: "Handbook of Pharmaceutical Excipients, Second Edition", Jan. 1, 1994, The Pharmaceutical Press, London, pp. 84-87.

McKay et al., 7,11,15,28-Tetrakis[(2-formylphenoxy)methyl]-1,21,23,25-tetramethylresorcin[4]arene cavitand ethyl acetate clathrate at 173 K, Acta Crystallographica, Section E: Structure Reports Online (2009), E65(4), 692-693 CODEN: ACSEBH; ISSN: 1600-5368 URL: http://journals.iucr.org/e/issues/2009/04/00/fl22 33/fl2233.pdf.

McKay et al., "Microwave-assisted synthesis of a new series of resorcin[4]arene cavitand-capped porphyrin capsules", Organic & Biomolecular Chemistry (2009), 7(19), 3958-3968 CODEN: OBCRAK; ISSN: 1477-0520.

Merlino et al., "Development of second generation amidinohydrazones, thio- and semicarbazones as Trypanosoma cruzi-inhibitors bearing benzofuroxan and benzimidazole 1,3-dioxide core scaffolds", MedChemComm (2010), 1(3), 216-228 CODEN: MCCEAY; ISSN: 2040-2503.

Mesguiche et al.,"4-Alkoxy-2,6-diaminopyrimidine Derivatives: Inhibitors of Cyclin Dependent Kinases 1 and 2," Bioorganic & Medicinal Chemistry Letters, Jan. 2003, vol. 13, pp. 217-222.

Metcalf, et al., "Discovery of GBT440, an Orally Bioavailable R-State Stabilizer of Sickle Cell Hemoglobin," ACS Med. Chem. Lett., 2017, 8, 321-326.

Mitra et al., "Synthesis and biological evaluation of dibenz[b,f][1,5]oxazocine derivatives for agonist activity at x-opioid receptor", European Journal of Medicinal Chemistry (2011), 46(5), 1713-1720 CODEN: EJMCAS; ISSN: 0223-5234.

Mulwad et al., "Synthesis and antimicrobial activity of [6'-methyl-4'-methoxy-2-oxo-2H-[1]-benzopyran)-2",4" dihydro-[1",2",4"]-triazol-3'-one and 3'phenylthiazolidin-4'-one-phenoxymethyl derivatives of dipyranoquinoline", Pharmaceutical Chemistry Journal Ahead of Print CODEN: PCJOAU; ISSN: 0091-150, 2011; pp. 427-432.

Muzaffar, et al., "Polymorphism and Drug Availability: a ReReview" J of Pharm. (Lahore), 1979, 1(1), 59-66.

Nagy et al., Selective coupling of methotrexate to peptide hormone carriers through a y-carboxamide linkage of its glutamic acid moiety: Benzotriazol-1-yloxytris(dimethylamino)phosphonium hexafluorophosphate activation in salt coupling. Proc. Natl. Acad. Sci. USA 1993, 90:6373-6376.

Neelima et al., "A novel annelation reaction: synthesis of 6H-[1]benzopyrano[4,3-b]quinolines" Chemistry & Industry (London, United Kingdom) (1986), (4), 141-2 CODEN: CHINAG; ISSN: 0009-3068.

Nnamani, et al., "Pyridyl derivatives of benzaldehyde as potential antisickling agents," Chem. Biodivers., (2008), 5(9):1762-1769.

Nogrady, Medicinal Chemistry A Biochemical Approach, Oxford University Press, New York, pp. 388-393 (1985).

Nonoyama et al.,"Cyclometallation of 2-(2-pyridyl)benzo[b]furen and 1-(2-pyridyl and 2-pyrimidyl)indole with palladium(II) and rhodium(III). Structures of unexpectedly formed nitro palladium(II) complexes", Polyhedron 1999, 533-543 CODEN: PLYHDE; ISSN: 0277-5387.

Notice of Allowance dated Dec. 19, 2014 for U.S. Appl. No. 13/730,730. 11 pages.

Nyerges et al, "Synthesis of Indazole N-oxides via the 1,7-electrocyclization of azomethine ylides", Tetrahedron Letters (2001), 42(30), 5081-5083 CODEN: TELEAY; ISSN:0040-4039.

Nyerges et al, "Synthesis of Indazole N-oxides via the 1,7-electrocyclization of azomethine ylides", Tetrahedron Letters (2004), 60(44), 9937-9944 CODEN: TETRAB; ISSN:0040-4020.

OECD SIDS "SIDS Initial Assessment Report for 13th SIAM," Nov. 2001, pp. 1-95.

Office Action dated Aug. 29, 2014 for U.S. Appl. No. 13/730,730. 17 pages.

Office Action dated Dec. 3, 2013 for U.S. Appl. No. 13/730,674. 8 pages.

Office Action dated Jul. 6, 2015 for U.S. Appl. No. 13/815,874. 14 pages.

Office Action dated Jun. 12, 2015 for CN Application No. 201280070743.5. 13 pages.

Office Action dated Jun. 29, 2015 for U.S. Appl. No. 13/815,810. 19 pages.

Office Action dated Jun. 30, 2014 for U.S. Appl. No. 13/730,674. 9 pages.

Office Action dated Sep. 18, 2013 for U.S. Appl. No. 13/730,674. 10 pages.

Oh, et al. Solid-phase synthesis of 1,3-oxazolidine derivatives. Tetrahedron Letters. 2000; 41:5069-5072.

(56) References Cited

OTHER PUBLICATIONS

O'Reilly, "Metal-phenoxyalkanoic acid interactions, XXV. The crystal structures of (2-formyl-6-methoxyphenoxy)acetic acid and its zinc(II)complex and the lithium, zinc(II) and cadmium(II) complexes of (2-chlorophenoxy)acetic acid", Australian Journal of Chemistry (1987), 40(7)m 1146-59 CODEN; AJCHAS; ISSN:0004-9425.
Otsuka, et al., "Effect of Polymorphic Forms of Bulk Powders on Pharmaceutical Properties of Carbamazepine Granules." Chem. Pharm. Bull., 47(6) 852-856 (1999).
Patani, et al. Bioisosterism: A Rational Approach in Drug Design. J. Chem Rev. 1996, 96(8), pp. 3147-3176.
Pearson, et al. Experimental and Computational Studies into an ATPH-Promoted exo-Selective IMDA Reaction: A Short Total Synthesis of Δ9-THC*. Chem. Eur. J. 2010, 16, 8280-8284.
Perez et al., "Preparation of new 1,2-disubstituted ferrocenyl ammonium salt", Polyhedron (2009), 28(14), 3115-3119 CODEN: PLYHE; ISSN:0277-5387.
Perkins et al., "Manganese(II), Iron(II), cobalt(II), and cooper(II)complexes of an extended inherently chiral tris-bipyridyl cage", Proceedings of the National Academy of Sciences of the United States of America (2006), 103(3), 532-537 CODEN: PNASA6; ISSN: 0027-8424.
Potapov, et al. A convenient synthesis of heterocyclic compounds containing 11-oxo-6,11,12,13-tetrahydrodibenzo[b,g][1,5]oxazonine fragment. Mendeleev Communications. 2009; 19:287-289.
Prohens, et al. Polymorphism in pharmaceutical industry. The Pharmacist. Apr. 1, 2007; 373:58-68. (in Spanish with English abstract).
Pubchem CID 54009805 Create Date: Dec. 4, 2011 p. 1.
Pubchem CID 54883281 Create Date: Aug. 19, 2012 p. 1.
Remington's Pharmaceutical Sciences, 17th Edition, A. Gennaro editor, Easton Pennsylvania. Table of Contents. (1985).
Rodriguez-Spong, et al. General principles of pharmaceutical solid polymorphism: a supramolecular perspective. Adv Drug Deliv Rev. Feb. 23, 2004;56(3):241-74.
Rolan et al., "The pharmacokinetics, tolerability and pharmacodynamics of tucaresol (589C80); 4[2-formyl-3-hydroxyphenoxymethyl] benzoic acid), a potential anti-sickling agent, following oral administration to healthy subjects", British Journal of Clinical Pharmacology, 1993, 35(4):419-425.
Rooseboom et al., Enzyme-catalyzed activation of anticancer prodrugs. Pharmacol. Rev. 2004, 56:53-102.
Ruchirawat et al., "A novel synthesis of aporhoeadanes", Tetrahedron Letters (1984), 25(32), 3485-8 CODEN: TELEAY; ISSN: 0040-4039.
Safo, et al. Structural basis for the potent antisickling effect of a novel class of five-membered heterocyclic aldehydic compounds. J Med Chem. Sep. 9, 2004;47(19):4665-76.
Sahakitpichan et al., "A practical and highly efficient synthesis of lennoxamine and related isoindoloenzazepines" Tetrahedron (2004), 60(19), 4169-4172 CODEN: TETRAB; ISSN: 0040-4020.
Sahm et al., "Synthesis of 2-arylbenzofurans" Justus Liebigs Annalen der Chemie (1974), (4), 523-38 CODEN: JLACBF; ISSN: 0075-4617.
Sainsbury et al., "1,2-Dihydroisoquinolines, IV. Acylation" Tetrahedron (1966), 22(8), 2445-52 CODEN: TETRAB; ISSN: 0040-4020.
Sarodnick et al., "Quinoxalines XV, Convenient Synthesis and Structural Study of Pyrazolo[1,5-a]quinolines", Journal of Organic Chemistry (2009), 74(3), 1282-1287 CODEN: JOCEAH; ISSN: 0022-3263.
Schudel, et al. Uber die Chemie des Vitamins E. Helvetica Chimica Acta. 1963; 66:636-649.
Seddon. Pseudopolymorph: A Polemic. The QUILL Centre, the Queen's University of Belfast, United Kingdom. Jul. 26, 2004. 2 pages.

Shetty et al. Palladium catalyzed alpha-arylation of methyl isobutyrate and isobutyronitrile: an efficient synthesis of 2,5-disubstituted benzyl alcohol and amine intermediates. Tetrahedron Letters, 47:8021-8024 (2006).
Siddiqui et al., "The Presence of Substitutents on the Aryl Moiety of the Aryl Phosphoramidate Derivative of d4T Enhances Anti-HIV Efficacy in Cell Culture-Activity Relationship," J. Med. Chem., (1999), 42:393-399.
Silva et al., "Advances in prodrug design," Mini Rev. Med. Chem., (2005), 5(10):893-914.
Singh et al., "Reductive-Cyclization-Mediated Synthesis of Fused Polycyclic Quinolines from Baylis-Hillman Adducts of Acrylonitrile: Scope and Limitations", European Journal of Organic Chemistry (2009), (20), 3454-3466 CODEN: EJOCFK; ISSN:1434-193X.
Singhal, et al., "Drug Polymorphism and Dosage Form Design: a Practical Perspective" Advanced Drug Delivery reviews 56, p. 335-347 (2004).
Sobolev et al., Effect of acyl chain length and branching on the enantioselectivity of Candida rugosa lipase in the kinetic resolution of 4-(2-difluoromethoxyphenyl)-substituted 1,4-dihydropyridine 3,5-diesters. J. Org. Chem. 2002, 67:401-410.
Srivastava et al., "Synthesis and biological evaluation of 4-substituted tetrazolo[4,5-a]quinolines and 2,3-disubstituted quinoline derivatives", Indian Journal of Chemistry, Section B: Organic Chemistry Including Medicinal Chemistry (1989), 28B(7), 562-73 CODEN: IJSBOB; ISSN:0376-4699.
Starke et al., "Quinoxalines, Part 13: Synthesis and mass spectrometric study of aryloxymethylquinoxalines and benzo[b]furylquinoxalines" Tetrahedron (2004), 60(29), 6063-6078 CODEN: TETRAB; ISSN:0040-4020.
Stetinova, et al. Synthesis and Properties of 4-Alkylaminomethyl and 4-Alkoxymethyl Derivatives of 5-Methyl-2-Furancarboxylic Acid. Collection Czechosloval Chem. Commun. 1985; 51:2186-2192.
STN Registry Database Entry: CAS RN 1039927-57-5 (Entered STN: Aug. 20, 2008).
STN Registry Database Entry: CAS RN 1243541-58-3 (Entered STN: Sep. 29, 2010).
Strickley. Solubilizing excipients in oral and injectable formulations. Pharm Res. Feb. 2004;21(2):201-30.
Swann et al., "Rates of reductive elimination of substituted nitrophenols from the (indol-3-yl)methyl position of indolequinones", Journal of the Chemical Society, Perkin Transactions 2 (2001), (8), 1340-1345.
Table of Compounds, each of which can be found either in Table 1 of U.S. Pat. No. 9,018,210 or Table 1 of U.S. Pat. No. 9,012,450.
Taday, et al., "Using Terahertz Pulse Spectroscopy to Study the Crystalline Structure of a Drug: A Case Study of the Polymorphs of Ranitidine Hydrochloride." J of Pharm. Sci., 92(4), 2003, 831-838.
Testa et al., Hydrolysis in Drug and Prodrug Metabolism, Jun. 2003, Wiley-VCH, Zurich, 419-534.
Tome et al., "Product class 13: 1,2,3-triazoles", Science of Synthesis (2004), 13, 415-601 CODEN: SSCYJ9.
Tsuge, et al. Suppressive Effect of Vitamin B6-Sugar Derivatives on the Proliferation of Feline Mammary Tumor Cell, FRM. Vitamins (Japan), 2006; 80(11):537-542. (In Japanese with English Abstract).
U.S. Pharmacopia #23, National Formulary #18, 1995, 1843-1844.
Van Halbeek, et al., "Sialic Acid in Permethylation Analysis: Prepared and Identification of Partially O-Methylated Derivatives of methyl N-Acetyl-N-Methyl-beta-D-Neurominate Methyl Glycoside", Carbohydrate Research, vol. 60, No. 1, 1978, pp. 51-62, 53, and 59.
vanRompaey et al., "A versatile synthesis of 2-substituted 4-amino-1,2,4,5-tetrahydro-2-benzazepine-3-ones", Tetrahedron (2003), 59(24), 4421-4432 CODEN: TETRAB; ISSN:0040-4020.
vanRompaey et al., "Synthesis and evaluation of the 3B2-turn properties of 4-amino-1,2,4,5-tetrahydro-2-benzazepin-3-ones and of their spirocyclic derivative", European Journal of Organic Chemistry (2006), (13), 2899-2911 CODEN: EJOCFK; ISSN: 1434-193X.
Vicente et al., "Carbopalladation of Maleate and Fumarate Esters and 1,1-Dimethylallene with Ortho-Substituted Aryl Palladium Complexes" Organometallics (2010), 29(2), 409-416.

(56) References Cited

OTHER PUBLICATIONS

Vichinsky. "Emerging 'A' therapies in hemoglobinopathies: agonists, antagonists, antioxidants, and arginine." Hematology 2012, 271-275.
Vippagunta, et al. Crystalline Solids. Advanced Drug Delivery Reviews. 2001; 48:3-26.
Wang et al., "Studies of Benzothiophene Template as Potent Factor IXa (FIXa) Inhibitors in Thrombosis", Journal of Medicinal Chemistry (2010), 53, 1465-1472.
Warshawsky et al., "The synthesis of aminobenzazespinones as anti-phenylalanine dipeptide mimics and their use in NEP inhibition", Bioorganic & Medicinal Chemistry Letter (1996), 6(8), 957-962 CODEN: BMCLE8; ISSN: 0960-894X.
Wendt et al., "Synthesis and SAR of 2-aryl pyrido[2,3-d]pyrimidines as potent mGlu5 receptor antagonists", Bioorganic & Medicinal Chemistry Letters, Pergamon, Amsterdam, NL, vol. 17, No. 19, Sep. 14, 2007 (Sep. 14, 2007), pp. 5396-5399.
Wermuth, Camille G., "Molecular Variations Based on Isosteric Replacements", The Practice of Medicinal Chemistry, 1996, pp. 203-232.
Yan et al., "Synthesis, crystal structure and antibacterial activity of dibutyltin carboxylate", Huaxue Tongbao (2007), 70(4), 313-316 CODEN: HHTPAU; ISSN: 0441-3776.
Yan et al., "Synthesis, crystal structure and antibacterial activity of di-n-butyltin di-2(2-formylphenoxy)acetic ester", Yingyong Huaxue (2007), 24(6), 660-664.
Yang, et al. Structural requirement of chalcones for the inhibitory activity of interleukin-5. Bioorg Med Chem. Jan. 1, 2007;15(1):104-11. Epub Oct. 10, 2006.
Yoon et al., The Chirality Conversion Reagent for Amino Acids Based on Salicyl Aldehyde. Bull. Korean Chem. Soc., (2012), 33:1715-1718.
Zhang et al., "DFT study on RuII-catalyzed cyclization of terminal alkynals to cycloalkenes", International Journal of Quantum Chemistry (2009), 109(4), 679-687 CODEN: IJQCB2; ISSN:0020-7608.
Zhang, et al. A selective fluorescent chemosensor with 1, 2, 4-triazole as subunit for Cu (II) and its application in imaging Cu (II) in living cells. Dyes and Pigments. 2012; 92(3):1370-1375.
Zhang, et al. Current prodrug strategies for improving oral absorption of nucleoside analogues. Asian Journal of Pharmaceutical Sciences. Apr. 2014; 9(2):65-74.
Zhu et al., "Isoquinoline-pyridine-based protein kinase B/Akt antagonists: SAR and in vivo antitumor activity", Bioorganic & Medicinal Chemistry Letters, Pergamon, Amsterdam, NL, 2006, vol. 16, No. 12, pp. 3150-3155.
Zwaagstra et al., "Synthesis and Structure-Activity Relationships of Carboxylated Chalcones: A Novel Series of Cys-LT1 (LTD4) Receptor Antagonists", Journal of Medicinal Chemistry (1997), 40(7), 1075-1089 CODEN: JMCMAR; ISSN: 0022-2623.
Ashizawa et al., Polymorphism and crystallization of the pharmaceutical drugs (Iyakuhin No Takeigensho to Shoseki No Kagaku) Maruzen Planet Co., Ltd., Sep. 20, 2002, pp. 3-16 and pp. 273-278. (in Japanese with partial English translation).
Beringer et al., Remington's Pharmaceutical Sciences, Mack Pub., 21st Edition, 2005, pp. 1072-1076.
"Can Voxelotor Offer New HOPE for Sickle Cell Disease?," Dec. 3, 2018, available at: https://www.ashclinicalnews.org/on-location/voxelotor-offers-new-hope-sickle-cell-disease/. 4 pages.
Experimental Chemistry (vol. 2)(Jikken Kagaku Koza, Zoku), Separation and refining, Maruzen Co.Ltd. Jan. 25, 1967, pp. 159-178 and pp. 186-187. (in Japanese with partial English translation).
GBT Announces Positive Top-line Data from Part A of the Phase 3 HOPE Study of Voxelotor in Sickle Cell Disease, Press Release dated Jun. 27, 2018. Available at http://ir.gbt.com/phoenix.zhtml?c=254105&p=irol-newsArticle&ID=2356168.
Gu, et al. Grouping solvents by statistical analysis of solvent property parameters: implication to polymorph screening. Int J Pharm. Sep. 28, 2004;283(1-2):117-25.
International Preliminary Report on Patentability dated Jun. 5, 2018 for PCT/US2016/064723. (10 pages).
International Search Report and Written Opinion dated May 3, 2017 for PCT Application No. PCT/US2016/064723. 15 pages.
Lehrer, et al. GBT440, a novel anti-polymerization agent, for the treatment of sickle cell disease. Global Blood Therapeutics. Apr. 1, 2016. (50 pages) Retrieved from the Internet: http://casicklecell.org/img/PresentationSlidesWebinar3.pdf.
New Introduction of Pharmacology (Sin Yakuzaigaku Soron)(revised 3rd Edition),Apr. 10,1987, Nankodo Co., Ltd p. 111. (in Japanese with partial English translation).
New Pharmaceutical Preparation (Shin Seizaigaku), Nanzando Co.,Ltd., Apirl 25, 1984, p. 102-103 and pp. 232-233. (in Japanese with partial English translation).
Paul, et al. Hydroxyl directed C-arylation: synthesis of 3-hydroxyflavones and 2-phenyl-3-hydroxy pyran-4-ones under transition-metal free conditions. Org. Biomol. Chem., 2018, 16:444-451.
Pharmacy—Foundation and Application—(Chozaigaku, Kiso to Ouyou), Nanzando Co.,Ltd., Sep. 20, 1977 p. 142-145. (in Japanese with partial English translation).
Reagan-Shaw, et al. Dose translation from animal to human studies revisited. The FASEB Journal. Mar. 2007; 22:659-661.
Shin, et al. Interpretation of Animal Dose and Human Equivalent Dose for Drug Development. The Journal of Korean Oriental Medicine. 2010; 31(3):1-7.
The Pharmacopoeia of Japan the Sixteen edition, 2011 pp. 64-68 2.58 X-ray powder diffraction measuring method p. 2070 (in Japanese with partial English translation).

* cited by examiner

TABLETS COMPRISING 2-HYDROXY-6-((2-(1-ISOPROPYL-1H-PYRAZOL-5-YL)PYRIDIN-3-YL)METHOXY)BENZALDEHYDE

CROSS-REFERENCE TO RELATED APPLICATIONS

This application claims the benefit under 35 U.S.C. § 119(e) of U.S. Provisional Application 62/407,406, filed Oct. 12, 2016, and U.S. Provisional Application 62/553,716, filed Sep. 1, 2017, which are hereby incorporated by reference in their entireties.

FIELD

Provided herein are high strength/high drug load tablets comprising 2-hydroxy-6-((2-(1-isopropyl-1H-pyrazol-5-yl)pyridin-3-yl)methoxy)benzaldehyde (hereinafter "Compound 1" or "voxelotor"), formulations and compositions of Compound 1, and processes of manufacturing such tablets. The present disclosure also provides rapidly disintegrating dispersible tablets of Compound 1. Also included are methods of treating patients with the tablets. Compound 1 is useful for treating hematological disorders such as sickle cell disease, pulmonary disease such as idiopathic pulmonary fibrosis, and hypoxia and hypoxemia conditions.

BACKGROUND

It has been reported that approximately 50% of patients in developed countries do not take their medications as prescribed, that complex drug regimen is a factor contributing to poor medication adherence, and that adherence lies between treatment and outcomes.

Non-adherence to medicines is estimated to cost the health care system $100 billion-$300 billion per year, and numerous studies have shown that high rates of non-adherence directly relates to poor clinical outcomes. Further, simple dosing, for example one pill per day, helps maximize adherence, and medicines that lower the number of pills per day help eliminate some of the known barriers to adherence.

Compound 1 is a small molecule active pharmaceutical ingredient in clinical development stage for the treatment of sickle cell disease, pulmonary disease such as idiopathic pulmonary fibrosis, and hypoxia and hypoxemia conditions. The clinical doses of Compound 1, in adults, can be considered high. Clinical doses include Compound 1 in the range of 500 mg to 1000 mg, or up to 1500 mg, administered orally once a day in either 100 or 300 mg capsules. The high dose 300 mg capsules are Size 0 HPMC capsules and contain over 80% of Compound 1. For example, a size 0 capsule measures 21.6 mm length×7.64 mm diameter and only 300 mg of Compound 1 drug can be loaded in to such a capsule. Therefore, for the capsule formulation, 300 mg is the maximum strength feasible due to the density characteristics and the fixed fill volume and dimensions of the Size 0 capsule shell used.

Thus, there is a need for developing a pharmaceutical formulation containing Compound 1 that is suitable for making alternative dosage forms such as tablets that contain varying amounts of higher doses of Compound 1 to minimize the number of pills to be swallowed by a patient (pill burden) per dose, has suitable size for ease of swallowing, and releases Compound 1 such that it leads to the desired therapeutic effect. Another important advantage of tablet formulations over the capsules is the ability to scale up to commercial volumes and use high speed manufacturing equipment while keeping low cost of goods. The present disclosure fulfills this and related needs.

SUMMARY

Provided herein are pharmaceutical compositions that are amenable to large scale manufacturing of high dose (high drug loaded) tablets of Compound 1, including Form II. Such compositions can possess high tablet hardness and low friability, are easily swallowed by patients, and/or release Compound 1 such that it leads to the desired therapeutic effect. Also provided herein are tablets that can provide a wide range of tablet strengths for achieving high dosing requirements and also low dosing needs.

In a first aspect is a tablet comprising from about 50% to about 70% by weight of Compound 1 and a microcrystalline cellulose as a filler provided that at least one microcrystalline cellulose is a high-compactable microcrystalline cellulose and wherein the % by weight is relative to the total weight of the tablet.

Also provided herein are dispersible tablets of Compound 1, wherein the tablet rapidly disintegrates in liquid. In some embodiments, the tablet rapidly disintegrates in less than about 10 mL of liquid. Such tablets can be easily administrated to patients, such as patients between the ages of 9 months old to about 11 years old or patients with difficulty swallowing tablets or capsules.

Some embodiments herein also provide for methods of treating a condition associated with oxygen deficiency in a patient in need thereof comprising administering to the patient a tablet or dispersible tablet as described herein.

Also provided herein are methods of making tablets described herein.

EMBODIMENTS

Figure 1:
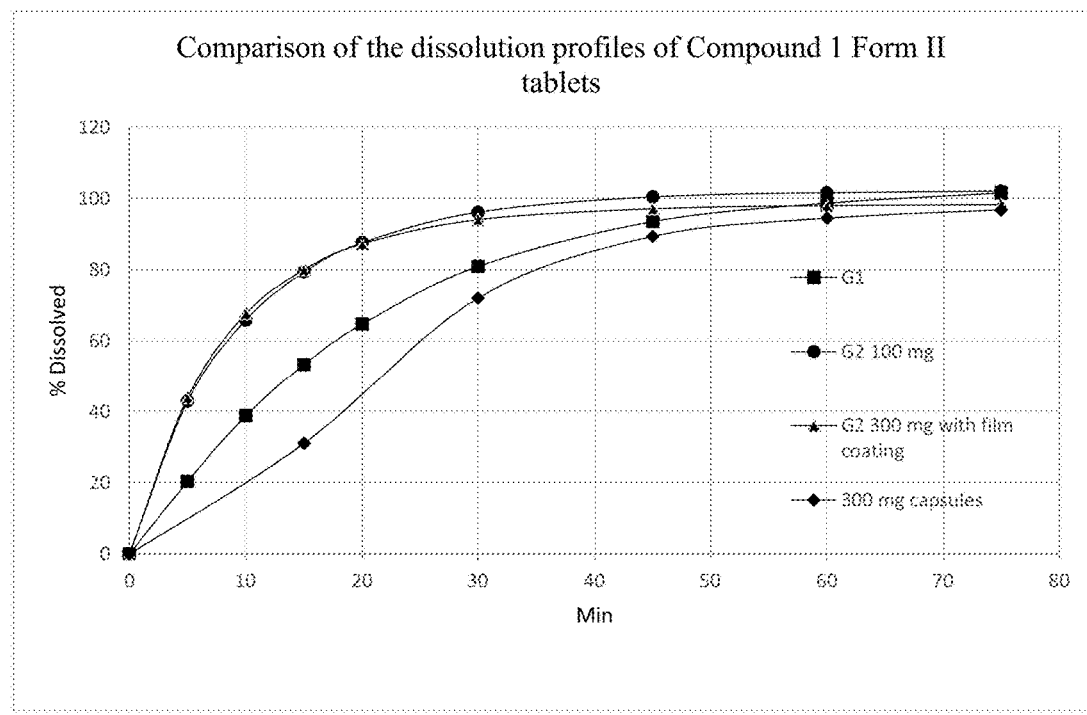
FIG. 1 shows in vitro dissolution profiles of Form II of Compound 1 tablets G1 and G2, compared to capsule reference product. G1 tablets were at 100 mg strength; G2 tablets were at 100 mg strength and at 300 mg strength with the film coating as per Example 4. Capsules were at 300 mg strength.
Figure 2:
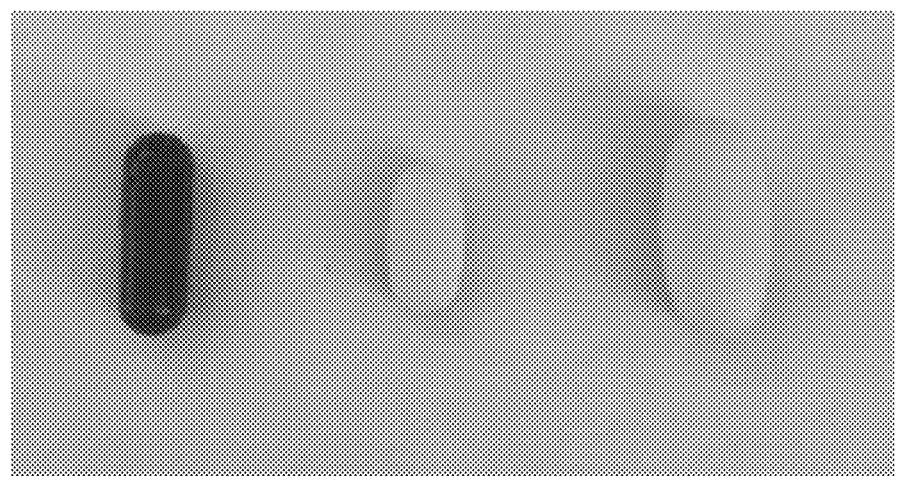
FIG. 2 provides a visual comparison of the size differences between a capsule at 300 mg strength (on the left), a tablet of Compound 1 at 300 mg strength (middle), and a tablet of Compound 1 at 900 mg strength (on the right).

In embodiment 1a, the tablet of the first aspect comprises from about 50% to about 65% by weight of Compound 1. In one embodiment, the tablet comprises Compound 1 in an amount of from about 50% to about 65% by weight of the tablet. In one sub-embodiment of embodiment 1a, the tablet comprises Compound 1 in an amount about of 65% by weight of the tablet. In a second sub-embodiment of embodiment 1a, the tablet comprises Compound 1 in an amount of about 60% by weight of the tablet. In a third sub-embodiment of embodiment 1a, the tablet comprises Compound 1 in an amount of about 60%±5% by weight of the tablet. In a fourth sub-embodiment of embodiment 1a, the tablet comprises Compound 1 in an amount of about 60%±2% by weight of the tablet. In a fifth sub-embodiment of embodiment 1a, the tablet comprises Compound 1 in an amount of about 60% by weight of the tablet.

In embodiment 1b, the tablet of the first aspect and embodiment 1a and sub-embodiments contained therein, the tablet comprises a high-compactable microcrystalline cellulose in an amount from about 20% to about 40% by weight of the tablet. In one sub-embodiment of embodiment 1b, the tablet comprises a high-compactable microcrystalline cellulose in an amount of about 30% by weight of the tablet. In another sub-embodiment of embodiment 1b, the tablet comprises a high-compactable microcrystalline cellulose in an amount of about 35% by weight of the tablet. In yet another sub-embodiment of embodiment 1b, the tablet comprises a high-compactable microcrystalline cellulose in an amount of 35%±2% by weight of the tablet. In yet another sub-embodiment of embodiment 1b, the tablet comprises a high-compactable microcrystalline cellulose in an amount of 35% by weight of the tablet. In yet another sub-embodiment of embodiment 1b, the tablet comprises a high-compactable microcrystalline cellulose in an amount of 35%±2% by weight of the tablet. In yet another sub-embodiment of embodiment 1b and sub-embodiments contained therein, the microcrystalline cellulose is a high-compactable microcrystalline cellulose. In yet another sub-embodiment of embodiment 1b and sub-embodiments contained therein, the high-compactable microcrystalline cellulose is Ceolus™ UF-711. In another sub-embodiment of embodiment 1b and sub-embodiments contained therein, the high-compactable microcrystalline cellulose is Ceolus™ KG-1000 or KG-802.

In embodiment 1c, the tablet of the first aspect and embodiments 1a and 1b and sub-embodiments contained therein, Compound 1 is a substantially pure crystalline ansolvate form (Form II) characterized by at least two, three, or four X-ray powder diffraction peaks (Cu Kα radiation) selected from 13.37°, 14.37°, 19.95° and 23.92° 2θ (each ±0.2° 2θ). In one embodiment of embodiment 1c, Compound 1 is 95% in the crystalline ansolvate form characterized by at least two, three, or four X-ray powder diffraction peaks (Cu Kα radiation) selected from 13.37°, 14.37°, 19.95° and 23.92° 2θ (each ±0.2° 2θ) and 5% Form I and/or Form N.

In embodiment 1d, the tablet of the first aspect and embodiments 1a and 1b and sub-embodiments contained therein, the tablet consists essentially of Compound 1 as a crystalline ansolvate form (Form II) characterized by at least two, three, or four X-ray powder diffraction peaks (Cu Kα radiation) selected from 13.37°, 14.37°, 19.95° and 23.92° 2θ (each ±0.2° 2θ).

In embodiment 1e, the tablet of the first aspect, embodiments 1a, 1b, 1c, and 1d, and sub-embodiments contained therein further comprises a disintegrant wherein the amount of disintegrant is from 0% to about 10% by weight of the tablet. In one subembodiment of embodiment 1e, the amount of disintegrant is from about 0.75% to about 1.5% by weight of the tablet. In another subembodiment of embodiment 1e, the amount of disintegrant is from about 1% to about 1.5% by weight of the tablet. In another subembodiment of embodiment 1e, the amount of disintegrant is 1.25±0.2% by weight of the tablet. In yet another subembodiment of embodiment 1e, and subembodiments contained therein, the disintegrant is croscarmellose sodium.

In embodiment 1f, the tablet of the first, second, third, fourth and fifth aspects, embodiments 1a, 1b, 1c, 1d, and 1e and sub-embodiments contained therein is, the tablet further comprises a lubricant, wherein the amount of lubricant is from about 1.75% to about 2.75% by weight of the tablet. In one subembodiment of embodiment 1f, the amount of lubricant is from about 2.0% to about 2.5% by weight of the tablet. In another subembodiment of embodiment 1f, the amount of lubricant is 2.25±0.2% w/w of the tablet. In another subembodiment of embodiment 1f, and subembodiments contained therein, the lubricant is magnesium stearate.

In embodiment 1g, the tablet of the first aspect, embodiments 1a and 1b and sub-embodiments contained therein further comprises a surfactant wherein the amount of surfactant is from about 1% to about 2% by weight of the tablet. In one subembodiment of embodiment 1g, the amount of surfactant is 1.5±0.2% by weight of the tablet. In another subembodiment of embodiment 1g, and subembodiments contained therein, the surfactant is sodium lauryl sulfate.

In a second aspect, provided herein is a tablet comprising a granular component wherein the granular component comprises:
  (i) about 60% by weight of Compound 1;
  (ii) a high-compactable microcrystalline cellulose;
  (iii) optionally a disintegrant;
  (iv) a lubricant;
  (v) optionally a surfactant; and
  (vi) optionally a binder;
wherein the percentage by weight is relative to the total weight of the tablet.

In embodiment 2a, the granular component of the second aspect comprises:
  (i) a high-compactable microcrystalline cellulose in the amount of about 27.50% by weight of the tablet;
  (ii) a disintegrant is present in the amount of about 1% by weight of the tablet; and
  (iii) a lubricant is present in the amount of about 1.50% by weight of the tablet.

In one subembodiment of embodiment 2a:
  (i) the amount of high-compactable microcrystalline cellulose is 27.50±2% by weight of the tablet;
  (ii) the amount of disintegrant is 1±0.2% by weight of the tablet; and
  (iii) the amount of lubricant is 1.50±0.2% by weight of the tablet.

In embodiment 2b, the tablet of embodiment 2a and subembodiment thereof the high-compactable microcrystalline cellulose is Ceolus™ UF-711; the disintegrant is croscarmellose sodium, the lubricant is magnesium stearate and Compound 1 is a substantially pure crystalline ansolvate form characterized by at least two, three or four X-ray powder diffraction peaks (Cu Kα radiation) selected from 13.37°, 14.37°, 19.95° and 23.92° 2θ (each ±0.2° 2θ). In one subembodiment of embodiment 2b, Compound 1 is 95% in crystalline ansolvate form characterized by at least two, three, or four X-ray powder diffraction peaks (Cu Kα radiation) selected from 13.37°, 14.37°, 19.95° and 23.92° 2θ (each ±0.2° 2θ) and 5% in Form I and/or Form N; and surfactant is absent.

In a third aspect, provided herein is a tablet comprising a granular component wherein the granular component consists essentially of:
  (i) about 60% by weight of Compound 1;
  (ii) a high-compactable microcrystalline cellulose;
  (iii) optionally a disintegrant;
  (iv) a lubricant;
  (v) optionally a surfactant; and
  (vi) optionally a binder;
wherein the percentage by weight is relative to the total weight of the tablet.

In embodiment 3a, the granular component of the third aspect comprises:
  (i) a high-compactable microcrystalline cellulose in the amount of about 27.50% by weight of the tablet;

(ii) the disintegrant is present in the about of about 1% by weight of the tablet; and
(iii) the lubricant is present in the amount of about 1.50% by weight of the tablet; and
(iv) optionally about 1.5% by weight a surfactant.

In one subembodiment of embodiment 3a:
(i) the amount of high-compactable microcrystalline cellulose is 27.50±2% by weight of the tablet;
(ii) the amount of disintegrant is 1±0.2% by weight of the tablet;
(iii) the amount of lubricant is 1.50±0.2% by weight of the tablet;
(iv) surfactant is absent.

In embodiment 3b, the tablet of embodiment 2a and subembodiment thereof the high-compactable microcrystalline cellulose is Ceolus™ UF-711; the disintegrant is croscarmellose sodium, the lubricant is magnesium stearate and Compound 1 is a substantially pure crystalline ansolvate form characterized by at least two, three or four X-ray powder diffraction peaks (Cu Kα radiation) selected from 13.37°, 14.37°, 19.95° and 23.92° 2θ (each ±0.2° 2θ). In one subembodiment of embodiments 3b, Compound 1 is 95% in crystalline ansolvate form characterized by at least two, three, or four X-ray powder diffraction peaks (Cu Kα radiation) selected from 13.37°, 14.37°, 19.95° and 23.92° 2θ (each ±0.2° 2θ) and 5% in Form I and/or Form N and the surfactant is absent.

In embodiment 3c, the tablet of the second and third aspects and embodiments contained therein (e.g., 2a, 2b, 3a and 3b) further comprises an extragranular component.

In embodiment 3d, the extragranular component of embodiment 3c comprises:
(i) a microcrystalline cellulose;
(ii) a disintegrant;
(iii) optionally a surfactant;
(iv) a lubricant; and
(v) optionally a coating;
provided that at least one of intragranular or extragranular component of the tablet contains a surfactant.

In embodiment 3f, the tablet of embodiments 3d wherein:
(i) the amount of extragranular microcrystalline cellulose is about 7.50% by weight of the tablet;
(ii) the amount of extragranular disintegrant is about 0.25% by weight of the tablet;
(iii) a surfactant is present in the amount of is about 1.50% by weight of the tablet; and
(iv) the amount of extragranular lubricant is about 0.75% by weight of the tablet.

In embodiment 3g, the tablet of embodiment 3f wherein the microcrystalline cellulose is a high-compactable microcrystalline cellulose selected from Ceolus™ UF-711, Ceolus™ KG-1000 or KG-802, preferably Ceolus™ UF-711; the disintegrant is croscarmellose sodium, the lubricant is magnesium stearate and the surfactant is sodium lauryl sulfate.

In embodiment 3h, the extragranular component of embodiment 3c consists essentially of:
(i) a microcrystalline cellulose;
(ii) a disintegrant;
(iii) optionally a surfactant;
(iv) a lubricant and
(v) optionally a coating;
provided that at least one of intragranular or extragranular component of the tablet contains a surfactant.

In embodiment 3i, the tablet of embodiments 3h comprises:
(i) the amount of extragranular microcrystalline cellulose is about 7.50% by weight of the tablet;
(ii) the amount of extragranular disintegrant is about 0.25% by weight of the tablet;
(iii) a surfactant is present and the amount is about 1.50% by weight of the tablet; and
(iv) the amount of extragranular lubricant is about 0.75% by weight of the tablet.

In embodiment 3j, the tablet of embodiment 3i comprises a microcrystalline cellulose wherein the microcrystalline cellulose a high-compactable microcrystalline cellulose Ceolus™ UF-711; the disintegrant is croscarmellose sodium, the lubricant is magnesium stearate and the surfactant is sodium lauryl sulfate.

In embodiment 4, the tablet of the first, second, and third aspects, embodiments 1a, 1b, 3(a-j) and embodiments contained therein the tablet comprises from about 300 mg to about 900 mg of Compound 1.

In embodiment 4a, the tablet comprises 300 mg, 400 mg, 500 mg, 750 mg, or 900 mg. In one subembodiment of embodiment 4a, the tablet comprises 300 mg of Compound 1. In one subembodiment of embodiment 4a, the tablet comprises 900 mg of Compound 1. In one subembodiment of embodiment 4a, the tablet comprises 1500 mg of Compound 1.

In another embodiment is a tablet comprising from about 50% to about 70% by weight of Compound 1 and a microcrystalline cellulose as a filler provided that at least one microcrystalline cellulose is a high-compactable microcrystalline cellulose; wherein the % by weight is relative to the total weight of the tablet. In another embodiment is a tablet comprising from about 30% to about 70% by weight of Compound 1 and a microcrystalline cellulose as a filler provided that at least one microcrystalline cellulose is a high-compactable microcrystalline cellulose; wherein the % by weight is relative to the total weight of the tablet.

In one embodiment, the tablet comprises from about 50% to about 65% by weight of Compound 1. In one embodiment, the tablet comprises about 65% by weight of Compound 1. In one embodiment, the tablet comprises about 60% by weight of Compound 1. In one embodiment, the tablet comprises about 60%±5% by weight of Compound 1. In one embodiment, the tablet comprises about 60±2% by weight of Compound 1. In one embodiment, the tablet comprises about 60% by weight of Compound 1.

In another embodiment, the tablet comprises from about 20% to about 40% of a high-compactable microcrystalline cellulose by weight of the tablet. In another embodiment, the tablet comprises about 30% of a high-compactable microcrystalline cellulose by weight of the tablet. In another embodiment, the tablet comprises about 35% of a high-compactable microcrystalline cellulose by weight of the tablet. In yet another embodiment, the tablet comprises about 35±2% of a high-compactable microcrystalline cellulose by weight of the tablet. In yet another embodiment, the tablet comprises about 35% of a high-compactable microcrystalline cellulose by weight of the tablet. In yet another embodiment, the table comprises about 35±2% of a high-compactable microcrystalline cellulose by weight of the tablet. In one embodiment, the microcrystalline cellulose is a high-compactable microcrystalline cellulose. In yet another embodiment the high-compactable microcrystalline cellulose is Ceolus™ UF-711. In another embodiment, the high-compactable microcrystalline cellulose is Ceolus™ KG-1000 or KG-802.

In another embodiment, the tablet comprises Compound 1 as a substantially pure crystalline ansolvate form characterized by at least two, three, or four X-ray powder diffraction peaks (Cu Kα radiation) selected from 13.37°, 14.37°, 19.95° and 23.92° 2θ (each ±0.2° 2θ). In one embodiment, Compound 1 is 95% crystalline ansolvate form characterized by at least two, three, or four X-ray powder diffraction peaks (Cu Kα radiation) selected from 13.37°, 14.37°, 19.95° and 23.92° 2θ (each ±0.2° 2θ) and 5% Form I and/or Form N.

In another embodiment, the tablet consists essentially of Compound 1 as a crystalline ansolvate form characterized by at least two, three, or four X-ray powder diffraction peaks (Cu Kα radiation) selected from 13.37°, 14.37°, 19.95° and 23.92° 2θ (each ±0.2° 2θ).

In one embodiment, the tablets described herein further comprise a disintegrant wherein the amount of disintegrant is from 0% to about 10% by weight of the tablet. In one embodiment, the amount of disintegrant is from about 0.75% to about 1.5% by weight of the tablet. In another embodiment, the amount of disintegrant is from about 1% to about 1.5% by weight of the tablet. In another embodiment, the amount of disintegrant is 1.25±0.2% by weight of the tablet. In yet another embodiment, the disintegrant is croscarmellose sodium.

In another embodiment, the tablets described herein further comprise a lubricant, wherein the amount of lubricant is from about 1.75% to about 2.75% by weight of the tablet. In one embodiment, the amount of lubricant is from about 2.0% to about 2.5% by weight of the tablet. In another embodiment, the amount of lubricant is 2.25±0.2% w/w of the tablet. In another embodiment, the lubricant is magnesium stearate.

In another embodiment, the tablets described herein further comprise a surfactant wherein the amount of surfactant is from about 1% to about 2% by weight of the tablet. In one embodiment, the surfactant comprises about 1.5% by weight of the tablet. In one embodiment, the amount of surfactant is 1.5±0.2% by weight of the tablet. In another embodiment, the surfactant is sodium lauryl sulfate.

In another embodiment, the tablets described herein further comprise a glidant, wherein the glidant is in an amount of less than about 2% by weight of the tablet.

In another aspect, provided herein is a tablet comprising a granular component wherein the granular component comprises:
  (i) about 60% by weight of Compound 1;
  (ii) a high-compactable microcrystalline cellulose;
  (iii) optionally a disintegrant;
  (iv) a lubricant;
  (v) optionally a surfactant; and
  (vi) optionally a binder;
wherein the percentage by weight is relative to the total weight of the tablet.

In one embodiment, the granular component comprises:
  (i) a high-compactable microcrystalline cellulose in the amount of about 27.50% by weight of the tablet;
  (ii) a disintegrant in the amount of about 1% by weight of the tablet; and
  (iii) a lubricant in the amount of about 1.50% by weight of the tablet.

In one embodiment the granular component comprises:
  (i) high-compactable microcrystalline cellulose at an amount of 27.50±2% by weight of the tablet;
  (ii) disintegrant at an amount of 1±0.2% by weight of the tablet; and
  (iii) lubricant at an amount of 1.50±0.2% by weight of the tablet.

In one embodiment, the high-compactable microcrystalline cellulose is Ceolus™ UF-711; the disintegrant is croscarmellose sodium, the lubricant is magnesium stearate and Compound 1 is a substantially pure crystalline ansolvate form characterized by at least two, three or four X-ray powder diffraction peaks (Cu Kα radiation) selected from 13.37°, 14.37°, 19.95° and 23.92° 2θ (each ±0.2° 2θ). In one embodiment, Compound 1 is 95% in crystalline ansolvate form characterized by at least two, three, or four X-ray powder diffraction peaks (Cu Kα radiation) selected from 13.37°, 14.37°, 19.95° and 23.92° 2θ (each ±0.2° 2θ) and 5% Form I and/or Form N; and surfactant is absent.

In another aspect, provided herein is a tablet comprising a granular component consisting essentially of:
  (i) about 60% by weight of Compound 1;
  (ii) a high-compactable microcrystalline cellulose;
  (iii) optionally a disintegrant;
  (iv) a lubricant;
  (v) optionally a surfactant; and
  (vi) optionally a binder;
wherein the percentage by weight is relative to the total weight of the tablet.

In one embodiment, the granular component comprises:
  (i) a high-compactable microcrystalline cellulose in the amount of about 27.50% by weight of the tablet;
  (ii) a disintegrant in the amount of about 1% by weight of the tablet;
  (iii) a lubricant in the amount of about 1.50% by weight of the tablet; and
  (iv) optionally about 1.5% by weight a surfactant.

In one embodiment, the granular component comprises:
  (i) a high-compactable microcrystalline cellulose in the amount of about 27.50% by weight of the tablet;
  (ii) a disintegrant in the amount of about 1% by weight of the tablet;
  (iii) a lubricant in the amount of about 1.50% by weight of the tablet; and
  (iv) optionally a surfactant in the amount of about 1.5% by weight of the tablet.

In one embodiment, the granular component comprises:
  (i) high-compactable microcrystalline cellulose at an amount of 27.50±2% by weight of the tablet;
  (ii) disintegrant at an amount of 1±0.2% by weight of the tablet;
  (iii) lubricant at an amount of 1.50±0.2% by weight of the tablet; and
  (iv) surfactant is absent.

In one embodiment, the high-compactable microcrystalline cellulose is Ceolus™ UF-711; the disintegrant is croscarmellose sodium, the lubricant is magnesium stearate; and Compound 1 is a substantially pure crystalline ansolvate form characterized by at least two, three or four X-ray powder diffraction peaks (Cu Kα radiation) selected from 13.37°, 14.37°, 19.95° and 23.92° 2θ (each ±0.2° 2θ). In one embodiment, Compound 1 is 95% in crystalline ansolvate form characterized by at least two, three, or four X-ray powder diffraction peaks (Cu Kα radiation) selected from 13.37°, 14.37°, 19.95° and 23.92° 2θ (each ±0.2° 2θ) and 5% Form I and/or Form N and the surfactant is absent.

In one embodiment, the tablet further comprises an extragranular component.

In one embodiment, the extragranular component comprises:
  (i) a microcrystalline cellulose;
  (ii) a disintegrant;
  (iii) optionally a surfactant;
  (iv) a lubricant; and
  (v) optionally a coating;
provided that at least one of intragranular or extragranular components of the tablet contains a surfactant.

In one embodiment, a tablet described herein comprises:
(i) an extragranular microcrystalline cellulose in the amount of about 7.50% by weight of the tablet;
(ii) an extragranular disintegrant in the amount of about 0.25% by weight of the tablet;
(iii) a surfactant in the amount of is about 1.50% by weight of the tablet; and
(iv) an extragranular lubricant in the amount of about 0.75% by weight of the tablet.

In one embodiment, a tablet described herein comprises:
(i) an extragranular microcrystalline cellulose in the amount of about 7.50% by weight of the tablet;
(ii) an extragranular disintegrant in the amount of about 0.25% by weight of the tablet;
(iii) an extragranular surfactant in the amount of is about 1.50% by weight of the tablet; and
(iv) an extragranular lubricant in the amount of about 0.75% by weight of the tablet.

In one embodiment, a tablet described herein comprises:
(i) an extragranular microcrystalline cellulose in the amount of about 5% to about 10% by weight of the tablet;
(ii) an extragranular disintegrant in the amount of about 0.1% to about 0.5% by weight of the tablet;
(iii) a surfactant in the amount of about 1% to about 2% by weight of the tablet; and
(iv) an extragranular lubricant in the amount of about 0.5% to about 1% by weight of the tablet.

In one embodiment, the microcrystalline cellulose is a high-compactable microcrystalline cellulose selected from Ceolus™ UF-711, Ceolus™ KG-1000 or KG-802. In one embodiment, the high-compactable microcrystalline cellulose is Ceolus™ UF-711, the disintegrant is croscarmellose sodium, the lubricant is magnesium stearate and the surfactant is sodium lauryl sulfate. In one embodiment, the high-compactable microcrystalline cellulose is Ceolus™ UF-711, the disintegrant is croscarmellose sodium, the lubricant is magnesium stearate, the surfactant is sodium lauryl sulfate, and the glidant is colloidal silicon dioxide. In one embodiment, the extragranular microcrystalline cellulose is high-compactable microcrystalline cellulose, the extragranular disintegrant is croscarmellose sodium, the extragranular lubricant is magnesium stearate; and the extragranular surfactant is present and is sodium lauryl sulfate. In one embodiment, the high-compactable microcrystalline cellulose is Ceolus™ UF-711.

In one embodiment, the extragranular component consists essentially of:
(i) a microcrystalline cellulose;
(ii) a disintegrant;
(iii) optionally a surfactant;
(iv) a lubricant; and
(v) optionally a coating;
provided that at least one of intragranular or extragranular components of the tablet contains a surfactant.

In one embodiment, the tablets described herein comprise:
(i) an extragranular microcrystalline cellulose in the amount of about 7.50% by weight of the tablet;
(ii) an extragranular disintegrant in the amount of about 0.25% by weight of the tablet;
(iii) a surfactant in the amount of about 1.50% by weight of the tablet; and
(iv) an extragranular lubricant in the amount of about 0.75% by weight of the tablet.

In one embodiment, a tablet described herein comprises:
(i) an extragranular microcrystalline cellulose in the amount of about 5% to about 10% by weight of the tablet;
(ii) an extragranular disintegrant in the amount of about 0.1% to about 0.5% by weight of the tablet;
(iii) a surfactant in the amount of about 1% to about 2% by weight of the tablet; and
(iv) an extragranular lubricant in the amount of about 0.5% to about 1% by weight of the tablet.

In one embodiment, a tablet described herein comprises:
(i) an extragranular microcrystalline cellulose in the amount of about 5% to about 10% by weight of the tablet;
(ii) an extragranular disintegrant in the amount of about 0.1% to about 0.5% by weight of the tablet;
(iii) a surfactant in the amount of about 1% to about 2% by weight of the tablet;
(iv) an extragranular lubricant in the amount of about 0.5% to about 1% by weight of the tablet; and
(vii) optionally a glidant in the amount of less than about 2% by weight of the tablet.

In one embodiment, the microcrystalline cellulose is a high-compactable microcrystalline cellulose Ceolus™ UF-711; the disintegrant is croscarmellose sodium, the lubricant is magnesium stearate and the surfactant is sodium lauryl sulfate.

In one embodiment, the tablets described herein comprise from about 300 mg to about 900 mg of Compound 1.

In one embodiment, the tablets described herein comprise 300 mg, 400 mg, 500 mg, 750 mg, or 900 mg. In one embodiment, the tablets described herein comprise 300 mg of Compound 1. In one embodiment, the tablets described herein comprise 900 mg of Compound 1.

In one embodiment, the dispersible tablets described herein comprise:
(i) about 30% to about 70% by weight of Compound 1;
(ii) filler;
(iii) disintegrant;
(iv) glidant; and
(v) a lubricant;
wherein the percentage by weight is relative to the total weight of the tablet.

In one embodiment, the dispersible tablets described herein comprise:
(i) about 30% to about 70% by weight of Compound 1;
(ii) a filler;
(iii) a disintegrant;
(iv) a glidant;
(v) a lubricant;
(vi) a surfactant; and
(vii) optionally a binder;
wherein the amount of disintegrant to filler is in a ratio of about 1:28, and wherein the percentage by weight is relative to the total weight of the tablet.

In one embodiment, the tablets described herein comprise:
(i) about 30% to about 70% by weight of Compound 1;
(ii) a filler;
(iii) less than about 2% by weight of disintegrant;
(iv) a glidant;
(v) a lubricant
(vi) a surfactant; and
(vii) optionally a binder;
wherein the amount of disintegrant to filler is in a ratio of about 1:28, and wherein the percentage by weight is relative to the total weight of the tablet.

In one embodiment, the dispersible tablets described herein comprise:
(i) about 60% by weight of Compound 1 Form II;
(ii) about 20% to about 35% by weight of microcrystalline cellulose;
(iii) about 1% to about 2% by weight of croscarmellose sodium;
(iv) less than about 2% by weight of colloidal silicon dioxide;
(v) about 1% to about 5% by weight of magnesium stearate;
(vi) a sweetener;
(vii) a flavoring agent; and
(viii) a coloring agent;
wherein the percentage by weight is relative to the total weight of the tablet and wherein the dispersible tablet disintegrates in a liquid in less than 1 minute.

In a fourth aspect, provided is a method of increasing affinity of hemoglobin for oxygen in a patient comprising administering to the patient in need thereof a tablet described herein, wherein the tablet comprises a therapeutically effective amount of Compound 1. In one embodiment, the therapeutic amount of Compound 1 is from 50 mg to 2000 mg per day. In one embodiment, the therapeutic amount of Compound 1 is from 600 mg to 2000 mg per day. In one embodiment, the therapeutic amount of Compound 1 is 600 mg per day. In another embodiment, the therapeutic amount of Compound 1 is 900 mg. In another embodiment the therapeutic amount of Compound 1 is 1500 mg.

In a fifth aspect, provided is a method for treating a condition associated with oxygen deficiency in a patient having a condition associated with oxygen deficiency. In one embodiment, the method comprises administering to the patient in need thereof a tablet as described herein comprising a therapeutically effective amount of Compound 1. In one embodiment, the condition is sickle cell disease, cancer, a pulmonary disorder such as interstitial pulmonary fibrosis, stroke, high altitude sickness, an ulcer, a pressure sore, acute respiratory disease syndrome, acute lung injury, or a wound. In one embodiment, the condition is idiopathic pulmonary fibrosis. In one embodiment, the therapeutic amount of Compound 1 is from 50 mg to 2000 mg per day. In one embodiment, the therapeutic amount of Compound 1 is from 600 mg to 2000 mg per day. In one embodiment, the therapeutic amount of Compound 1 is 900 or 1500 mg once a day. In one embodiment, the therapeutic amount of Compound 1 is 600 mg per day. In another embodiment, the therapeutic amount of Compound 1 is 900 mg. In another embodiment the therapeutic amount of Compound 1 is 1500 mg.

DETAILED DESCRIPTION

Definitions

Unless defined otherwise, all technical and scientific terms used herein have the same meaning as is commonly understood by one of ordinary skill in the art. As used herein, the below terms have the following meanings unless specified otherwise. Any methods, devices and materials similar or equivalent to those described herein can be used in the practice of the compositions and methods described herein. The following definitions are provided to facilitate understanding of certain terms used frequently herein and are not meant to limit the scope of the present disclosure. All references referred to herein are incorporated by reference in their entirety.

Headings used in this application are for reference purposes only and do not in any way limit the present disclosure.

It is noted here that as used in this specification and the appended claims, the singular forms "a" "an" and "the" and the like include plural referents unless the context clearly dictates otherwise.

The term "about" or "approximately" means within ±30%, 20%, 15%, 10%, 9%, 8%, 7%, 6%, 5%, 4%, 3%, 2%, 1%, 0.5%, or 0.05% of a given value or range. In one embodiment, about means±5%. In another embodiment, about means±4% of a given value or range. In another embodiment, about means±3% of a given value or range. In another embodiment, about means±2% of a given value or range. In another embodiment, about means±1% of a given value or range. In another embodiment, about means±0.5% of a given value or range. In another embodiment, about means±0.05% of a given value or range.

It is to be understood that "w/w" refers to the percent weight of an agent or excipient relative to the total weight of the tablet only. Percent weights described herein do not include the weight of coatings as described herein unless explicitly stated as such.

As used herein "substantially pure" shall refer to ansolvate Form II of Compound 1 associated with about <10% or Form I and/or Form N, preferably <5% Form I and/or Form N; and most preferably it shall refer to about <2% Form I and/or Form N. When the Form II polymorph of Compound 1 is formulated as a pharmaceutical composition, "substantially pure" shall preferably refer to about <15% Form I and/or Form N polymorph of Compound 1; preferably, the term shall refer to about <10% Form I and/or Form N polymorph of Compound 1 and more preferably the term shall refer to about <5% Form I and/or Form N polymorph of Compound 1. Form I of Compound 1 is characterized by X-ray powder diffraction peaks (Cu Kα radiation) at 12.82°, 15.74°, 16.03°, 16.63°, 17.60°, 25.14°, 25.82° and 26.44° 2θ (each ±0.2° 2θ); and Form N of Compound 1 is characterized by X-ray powder diffraction peaks (Cu Kα radiation) at 11.65°, 11.85°, 12.08°, 16.70°, 19.65° and 23.48° 2θ (each ±0.2° 2θ).

"UF-711" is used in accordance with its ordinary and common usage in the art refers to microcrystalline cellulose (MCC) (Compendial name: microcrystalline cellulose, NF, Ph. Eur., JP—Chemical Formula $(C_6H_{10}O_5)_n$) sold under the trade name CEOLUS®, grade UF-711. UF-711 typically has a powder grade/average particle size of about 50 µm and a bulk density of about 0.2-0.26 g/cm$^3$ (0.22 g/cm$^3$). UF-711 is typically characterized by about a 2% to about a 6% loss on drying and has an angle of repose of about 42 degrees. UF-711 typically has a compactibility index of about 1.5. UF-711 as used herein includes microcrystalline cellulose produced under the CEOLUS UF trademark by Asahi Kasei and any microcrystalline cellulose having substantially similar or identical properties.

The term "administration" refers to introducing an agent into a patient. A therapeutic amount can be administered, which can be determined by the treating physician or the like. An oral route of administration is preferred. The related terms and phrases administering" and "administration of," when used in connection with a compound or tablet (and grammatical equivalents) refer both to direct administration, which may be administration to a patient by a medical professional or by self-administration by the patient, and/or to indirect administration, which may be the act of prescribing a drug. Administration entails delivery to the patient of the drug.

The "crystalline ansolvate" of 2-hydroxy-6-((2-(1-isopropyl-1H-pyrazol-5-yl)pyridin-3-yl)methoxy)benzaldehyde (Compound 1) is a crystalline solid form of the free base of Compound 1, such as, e.g., crystalline Form I, Form II or Form N as disclosed in International Publication No. WO 2015/120133 A1 (see, e.g., pages 3-9 and pages 51-54), the disclosure of which is incorporated herein by reference in its entirety. Compound 1 (also known as "voxelotor") has the structure:

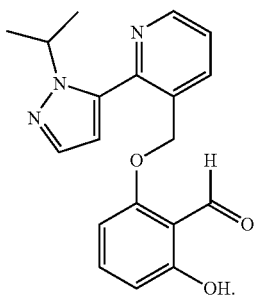 [SMILES: CC(C)n1nccc1-c1ncccc1COc1cccc(O)c1C=O]

"Characterization" refers to obtaining data which may be used to identify a solid form of a compound, for example, to identify whether the solid form is amorphous or crystalline and whether it is unsolvated or solvated. The process by which solid forms are characterized involves analyzing data collected on the polymorphic forms so as to allow one of ordinary skill in the art to distinguish one solid form from other solid forms containing the same material. Chemical identity of solid forms can often be determined with solution-state techniques such as $^{13}C$ NMR or $^{1}H$ NMR. While these may help identify a material, and a solvent molecule for a solvate, such solution-state techniques themselves may not provide information about the solid state. There are, however, solid-state analytical techniques that can be used to provide information about solid-state structure and differentiate among polymorphic solid forms, such as single crystal X-ray diffraction, X-ray powder diffraction (XRPD), solid state nuclear magnetic resonance (SS-NMR), and infrared and Raman spectroscopy, and thermal techniques such as differential scanning calorimetry (DSC), Solid state $^{13}C$-NMR, thermogravimetry (TG), melting point, and hot stage microscopy.

To "characterize" a solid form of a compound, one may, for example, collect XRPD data on solid forms of the compound and compare the XRPD peaks of the forms. For example, the collection of peaks which distinguish e.g., Form II from the other known forms is a collection of peaks which may be used to characterize Form II. Those of ordinary skill in the art will recognize that there are often multiple ways, including multiple ways using the same analytical technique, to characterize solid forms. Additional peaks could also be used, but are not necessary, to characterize the form up to and including an entire diffraction pattern. Although all the peaks within an entire XRPD pattern may be used to characterize such a form, a subset of that data may, and typically is, used to characterize the form.

An XRPD pattern is an x-y graph with diffraction angle (typically ° 2θ) on the x-axis and intensity on the y-axis. The peaks within this pattern may be used to characterize a crystalline solid form. As with any data measurement, there is variability in XRPD data. The data are often represented solely by the diffraction angle of the peaks rather than including the intensity of the peaks because peaks intensity can be particularly sensitive to sample preparation (for example, particle size, moisture content, solvent content, and preferred orientation effects influence the sensitivity), so samples of the same material prepared under different conditions may yield slightly different patterns; this variability is usually greater than the variability in diffraction angles. Diffraction angle variability may also be sensitive to sample preparation. Other sources of variability come from instrument parameters and processing of the raw X-ray data: different X-ray instruments operate using different parameters and these may lead to slightly different XRPD patterns from the same solid form, and similarly different software packages process X-ray data differently and this also leads to variability. These and other sources of variability are known to those of ordinary skill in the pharmaceutical arts. Due to such sources of variability, it is usual to assign a variability of ±0.2° 2θ to diffraction angles in XRPD patterns.

The term "dose" or "dosage" refers to the total amount of active material (e.g., Compound 1 disclosed herein) administered to a patient in a single day (24-hour period). The desired dose may be administered once daily. Alternatively, the desired dose may be administered in one, two, three, four or more sub-doses at appropriate intervals throughout the day, where the cumulative amount of the sub-doses equals the amount of the desired dose administered in a single day. The terms "dose" and "dosage" are used interchangeably herein.

As defined herein, where the mass of a Compound 1 is specified, for example, 300 mg or 900 mg of Compound 1, that amount corresponds to the mass of Compound 1 in its free base form in a single tablet.

The term "hemoglobin" as used herein refers to any hemoglobin protein, including normal hemoglobin (Hb) and sickle hemoglobin (HbS).

The term "sickle cell disease" refers to diseases mediated by sickle hemoglobin (HbS) that results from a single point mutation in the hemoglobin (Hb). Sickle cell diseases include sickle cell anemia, sickle-hemoglobin C disease (HbSC), sickle beta-plus-thalassaemia (HbS/β) and sickle beta-zero-thalassaemia (HbS/β0).

"Therapeutically effective amount" or "therapeutic amount" refers to an amount of a drug or an agent that when administered to a patient suffering from a condition, will have the intended therapeutic effect, e.g., alleviation, amelioration, palliation or elimination of one or more manifestations of the condition in the patient. The full therapeutic effect does not necessarily occur by administration of one dose, and may occur only after administration of a series of doses and can be administered in one dose form or multiples thereof. For example, 900 mg of the drug can be administered in a single 900 mg strength tablet or three 300 mg strength tablets. Thus, a therapeutically effective amount may be administered in one or more administrations. For example, and without limitation, a therapeutically effective amount of an agent, in the context of treating disorders related to hemoglobin S, refers to an amount of the agent that alleviates, ameliorates, palliates, or eliminates one or more manifestations of the disorders related to hemoglobin S in the patient.

The term "pharmaceutically acceptable" refers to generally safe and non-toxic for in vivo, preferably human, administration.

The term "patient" refers to a mammal, such as a human, bovine, rat, mouse, dog, monkey, ape, goat, sheep, cow, or deer. A patient as described herein can be a human. In some embodiments, the patient is an adult. In some embodiments, the patient is a child or juvenile. In some embodiments, the patient is about 9 months old to about 11 years old. In some embodiments, the patient is about 9 months old to about 11 years old and has difficulty swallowing.

"Treatment," "treating," and "treat" are defined as acting upon a disease, disorder, or condition with an agent to reduce or ameliorate the harmful or any other undesired effects of the disease, disorder, or condition and/or its symptoms. Treatment, as used herein, covers the treatment of a human patient, and includes: (a) reducing the risk of occurrence of the condition in a patient determined to be predisposed to the disease but not yet diagnosed as having the condition, (b) impeding the development of the condition, and/or (c) relieving the condition, i.e., causing regression of the condition and/or relieving one or more symptoms of the condition. For purposes of treatment of sickle cell disease, beneficial or desired clinical results include, but are not limited to, multi-lineage hematologic improvement, decrease in the number of required blood transfusions, decrease in infections, decreased bleeding, and the like. For purposes of treatment of interstitial pulmonary fibrosis, beneficial or desired clinical results include, but are not limited to, reduction in hypoxia, reduction in fibrosis, and the like.

As used herein, "% w/w" refers to the weight of a component based on the total weight of a composition comprising the component. For instance, if component 1 is present in an amount of 50% in a 100 mg composition, component 1 is present in an amount of 50 mg. In some embodiments, the composition refers to a formulation as described herein or tablet as described herein.

As used herein, "rapidly disintegrates" or "rapid disintegration" refers to, in some embodiments, disintegration (of, for example, a tablet as described herein) in a small amount of liquid in less than about 5 minutes, about 4 minutes, about 3 minutes, about 2 minutes, or about 1 minute. In some embodiments, the dispersible tablet disintegrates in a liquid in less than 1 minute. In some embodiments, a dispersible tablet disintegrates in less than about 10 mL, less than about 8 mL, less than about 7 mL, less than about 6 mL, or less than about 5 mL of liquid. In some embodiments, a dispersible tablet disintegrates in about 5 mL to about 30 mL, about 5 mL to about 25 mL, or about 5 mL to about 20 mL of liquid. In some embodiments, a dispersible tablet disintegrates in less than about 30 mL or less than about 25 mL of liquid.

Tablets

Many small molecule active pharmaceutical ingredients (APIs) can be formulated in low strength tablets because the physicochemical properties of the excipients used in the formulation dominate the properties of the solid composition rather than the physicochemical properties of the API. As the drug load increases the physicochemical properties of the drug substance become progressively dominant in the tablet manufacturing process. Because APIs can have a full spectrum of physicochemical properties and are not selected based on physicochemical properties that contribute favorably to the manufacturability and stability of a formulation, it is quite frequent that the physicochemical properties of API present the largest obstacles to creating a workable high strength formulation.

Compound 1 is a BCS II compound, where its solubility is the primary biopharmaceutical factor limiting absorption. Compound 1 exists in one form as an ansolvate crystalline form characterized by at least two, three or four X-ray powder diffraction peaks (Cu Kα radiation) selected from 13.37°, 14.37°, 19.95° and 23.92° 2θ (each ±0.2° 2θ) (see, e.g., PCT application Publication No. WO 2015/120133 A1, incorporated herein by reference in its entirety and for all purposes). This form can hereinafter also be referred to as Form II. The physicochemical properties of Compound 1, including its Form II, are not as conducive (compared to other drug substances for formulation) to making a high dosage form of Compound 1. For example, Form II of Compound 1 is considered to be poorly water soluble, lipophilic, and has a relatively low melting point. The bulk density of Form II of Compound 1 is considered low and its flowability considered poor. Upon milling, the flowability decreases. The compression characteristics of Form II of Compound 1 are also considered poor, exhibiting low tensile strength which does not increase significantly with compression force. Form II of Compound 1 is also prone to sticking to steel surfaces, such as in processing equipment for tablet manufacture.

In addition, another ansolvate crystalline form of Compound 1, referred to as Form N, is known. Form N has an enantiotropic relationship with Form II, with a transition temperature approximately in the range 30-40° C. Thus, under temperatures (e.g. storage) below 40° C., e.g., at 25° C., Compound 1 is more thermodynamically stable as Form II and at temperatures above 40° C., e.g., at 50° C., Compound 1 is more thermodynamically stable as Form N. To design tablets containing Compound 1, the above physicochemical property limitations of Compound 1 and the high dose requirements need to be accommodated while ensuring that the tablets have dissolution properties that lead to a therapeutic effect.

Described herein are tablets and dispersible tablets comprising Compound 1. It is also contemplated that the components of these tablets may also be comprised in a composition or a pharmaceutical formulation as described herein. Such compositions may be precursors to the tablets as described herein or may be other formulations known in the art, including, but not limited to, sachets.

In one embodiment, the tablets described herein comprise Compound 1 as a substantially pure crystalline ansolvate form characterized by at least two X-ray powder diffraction peaks (Cu Kα radiation) selected from 13.37°, 14.37°, 19.95° and 23.92° 2θ (each ±0.2° 2θ). In another embodiment, the tablets described herein consists essentially of Compound 1 as a crystalline ansolvate form characterized by at least two X-ray powder diffraction peaks (Cu Kα radiation) selected from 13.37°, 14.37°, 19.95° and 23.92° 2θ (each ±0.2° 2θ). In another embodiment, the crystalline ansolvate form of Compound 1 is characterized by at least three X-ray powder diffraction peaks (Cu Kα radiation) selected from 13.37°, 14.37°, 19.95° and 23.92° 2θ (each ±0.2° 2θ).

In one embodiment, the tablets described herein comprise Compound 1 that is 95% by weight Form II characterized by X-ray powder diffraction peaks (Cu Kα radiation) selected from 13.37°, 14.37°, 19.95° and 23.92° 2θ (each ±0.2° 2θ) and 5% by weight Compound 1 is Form I and/or Form N. In certain embodiments, the w/w of Form II to Form I/Form N is 99%/1%; 98%/2%; 97%/3%; 96%/4%, 95%/5%; 94%/6%; 93%/7%; 92%/8%, 91%/9% or 90%/10%. In certain embodiments, the w/w of Form II to Form I/Form N is 99.5%/0.5%; 99.6/0.4%; 99.7%/0.3%; 99.8%/0.2%; 99.9%/0.1%; or 99.95%/0.05%.

In one embodiment, the tablets described herein comprise Compound 1 that is at least 95% by weight Form II characterized by at least one X-ray powder diffraction peak (Cu Kα radiation) selected from 13.37°, 14.37°, 19.95° and 23.92° 2θ (each ±0.2° 2θ). In one embodiment, the tablets described herein comprise Compound 1 that is at least 96% by weight Form II characterized by at least one X-ray powder diffraction peak (Cu Kα radiation) selected from 13.37°, 14.37°, 19.95° and 23.92° 2θ (each ±0.2° 2θ). In one embodiment, the tablets described herein comprise Compound 1 that is at least 97% by weight Form II characterized by at least one X-ray powder diffraction peak (Cu Kα radiation) selected from 13.37°, 14.37°, 19.95° and 23.92° 2θ (each ±0.2° 2θ). In one embodiment, the tablets described herein comprise Compound 1 that is at least 98% by weight Form II characterized by at least one X-ray powder diffraction peak (Cu Kα radiation) selected from 13.37°, 14.37°, 19.95° and 23.92° 2θ (each ±0.2° 2θ). In one embodiment, the tablets described herein comprise Compound 1 that is at least 99% by weight Form II characterized by at least one X-ray powder diffraction peak (Cu Kα radiation) selected from 13.37°, 14.37°, 19.95° and 23.92° 2θ (each ±0.2° 2θ).

In one embodiment, the tablets described herein comprise Compound 1 that is at least 95% by weight Form II characterized by at least two X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 96% by weight Form II characterized by at least two X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 97% by weight Form II characterized by at least two X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 98% by weight Form II characterized by at least two X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 99% by weight Form II characterized by at least two X-ray powder diffraction peaks (Cu Kα radiation) selected from 13.37°, 14.37°, 19.95° and 23.92° 2θ (each ±0.2° 2θ).

In one embodiment, the tablets described herein comprise Compound 1 that is at least 95% by weight Form II characterized by at least three X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 96% by weight Form II characterized by at least three X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 97% by weight Form II characterized by at least three X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 98% by weight Form II characterized by at least three X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 99% by weight Form II characterized by at least three X-ray powder diffraction peaks (Cu Kα radiation) selected from 13.37°, 14.37°, 19.95° and 23.92° 2θ (each ±0.2° 2θ).

In one embodiment, the tablets described herein comprise Compound 1 that is at least 95% by weight Form II characterized by X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 96% by weight Form II characterized by X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 97% by weight Form II characterized by X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 98% by weight Form II characterized by X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 99% by weight Form II characterized by X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 99.5% by weight Form II characterized by X-ray powder diffraction peaks (Cu Kα radiation) selected from 13.37°, 14.37°, 19.95° and 23.92° 2θ (each ±0.2° 2θ). In one embodiment, the tablets described herein comprise Compound 1 that is at least 99.9% by weight Form II characterized by X-ray powder diffraction peaks (Cu Kα radiation) selected from 13.37°, 14.37°, 19.95° and 23.92° 2θ (each ±0.2° 2θ).

The tablets described herein can comprise Compound 1 (e.g. Form I, Form II, or Form N) at an amount of about: 40% to about 80%; 40% to about 70%; 40% to about 60%; 50% to about 80%; 50% to about 70%; or 50% to about 65% w/w. In one embodiment, tablets described herein comprise about 50% to about 70% or about 50% to about 65% w/w of Compound 1. Tablets described herein can comprise at least about: 40%, 45%, 50%, 55%, 60%, 65%, 70%, 75%, 80%, 85%, 90% or 95% w/w of Compound 1. Tablets described herein can comprise at least about: 40%, 45%, 50%, 55%, 60%, 65%, 70%, 75%, 80%, 85%, 90% or 95% (±2%) w/w of Compound 1. Tablets described herein can comprise at least about: 40%, 45%, 50%, 55%, 60%, 65%, 70%, 75%, 80%, 85%, 90% or 95% (±5%) w/w of Compound 1. In one embodiment, tablets described herein include about: 40%, 45%, 50%, 55%, 60%, 65%, 70%, 75%, 80%, 85%, 90% or 95% w/w of Compound 1. In one embodiment, tablets described herein include about: 40%, 45%, 50%, 55%, 60%, 65%, 70%, 75%, 80%, 85%, 90% or 95% (±2%) w/w of Compound 1. In one embodiment, tablets described herein include about: 25%, 30%, or 35% w/w of Compound 1. In one embodiment, tablets described herein include about: 25%, 30%, or 35% (±2%) w/w of Compound 1. In one embodiment, tablets described herein include about: 40%, 45%, 50%, 55%, 60%, 65%, 70%, 75%, 80%, 85%, 90% or 95% (±5%) w/w of Compound 1. In some embodiments, the tablets described herein comprise Compound 1 (e.g. Form I, Form II, or Form N) at an amount of about: 20% to about 40%; 30% to about 80%; 30% to about 70%; or 30% to about 60% w/w. In some embodiments, the tablets described herein comprise Compound 1 Form II at an amount of about 30% to about 70% w/w. In some embodiments, the tablets described herein comprise Compound 1 Form II at an amount of about 40% to about 70% w/w.

The tablets described herein can comprise Compound 1 (e.g. Form I, Form II, or Form N) in an amount of about: 300 mg, 450 mg, 600 mg, 750 mg, 900 mg, 1200 mg, 1500 mg, or 2000 mg. The tablets described herein can comprise Compound 1 (e.g. Form I, Form II, or Form N) in an amount of at least about: 300 mg, 450 mg, 600 mg, 750 mg, 900 mg, 1200 mg, 1500 mg, or 2000 mg. The tablets described herein can comprise Compound 1 (e.g. Form I, Form II, or Form N)

in an amount of about: 300 mg, 750 mg, or 900 mg. The tablets described herein can comprise Compound 1 (e.g. Form I, Form II, or Form N) in an amount of about: 300 mg to about 2000 mg; 600 mg to about 2000 mg; or 900 mg to about 1500 mg. In some embodiments, the tablets described herein can comprise Compound 1 (e.g. Form I, Form II, or Form N) in an amount of about 50 mg to about 2000 mg. In some embodiments, the tablets described herein can comprise Compound 1 (e.g. Form I, Form II, or Form N) in an amount of about 50 mg to about 900 mg. In some embodiments, the tablets described herein can comprise Compound 1 (e.g. Form I, Form II, or Form N) in an amount of about 300 mg to about 1500 mg. In some embodiments, the tablets described herein can comprise Compound 1 (e.g. Form I, Form II, or Form N) in an amount of about 900 mg to about 1500 mg. In some embodiments, the tablets described herein can comprise Compound 1 (e.g. Form I, Form II, or Form N) in an amount of about 100 mg to about 600 mg.

In some embodiments, the tablets described herein can comprise Compound 1 (e.g. Form I, Form II, or Form N) in an amount of about 50 mg. In some embodiments, the tablets described herein can comprise Compound 1 (e.g. Form I, Form II, or Form N) in an amount of about 100 mg. In some embodiments, the tablets described herein can comprise Compound 1 (e.g. Form I, Form II, or Form N) in an amount of about 200 mg. In some embodiments, the tablets described herein can comprise Compound 1 (e.g. Form I, Form II, or Form N) in an amount of about 300 mg. In some embodiments, the tablets described herein can comprise Compound 1 (e.g. Form I, Form II, or Form N) in an amount of about 450 mg. In some embodiments, the tablets described herein can comprise Compound 1 (e.g. Form I, Form II, or Form N) in an amount of about 600 mg. In some embodiments, the tablets described herein can comprise Compound 1 (e.g. Form I, Form II, or Form N) in an amount of about 900 mg.

In some embodiments, the tablets described herein can comprise Compound 1 Form II in an amount of about 50 mg. In some embodiments, the tablets described herein can comprise Compound 1 Form II in an amount of about 100 mg. In some embodiments, the tablets described herein can comprise Compound 1 Form II in an amount of about 300 mg. In some embodiments, the tablets described herein can comprise Compound 1 Form II in an amount of about 450 mg. In some embodiments, the tablets described herein can comprise Compound 1 Form II in an amount of about 600 mg. In some embodiments, the tablets described herein can comprise Compound 1 Form II in an amount of about 900 mg. In some embodiments, the tablets described herein can comprise Compound 1 Form II in an amount of about 1500 mg.

The tablet of the present disclosure comprises excipients such as pharmaceutically acceptable filler (also known as diluent), disintegrant, lubricant, and surfactant (also known as a wetting agent). In some embodiments, the tablets described herein further comprise a glidant. Excipients can have two or more functions in a pharmaceutical composition. Characterization herein of a particular excipient as having a certain function, e.g., filler, disintegrant, etc., should not be read as limiting to that function. Further information on excipients can be found in standard reference works such as Handbook of Pharmaceutical Excipients, 3rd ed. (Kibbe, ed. (2000), Washington: American Pharmaceutical Association). While frequently it is possible for formulators of ordinary skill in the art to interchange one functional excipient in a tablet for an alternate, in the tablet of the present disclosure, in some embodiments, one of the filler (diluent) has a specific requirement to be highly compactable (also referred to herein as highly compressible). High compactibility of such excipients can achieve a high drug load in a single tablet of reasonable size and at suitably high tensile strength to yield a robust tablet that survives pharmaceutical processing, packaging, and handling. An example of such fillers is high compressibility grades of microcrystalline cellulose (MCC). In one embodiment, the drug load of Compound 1 can be maximized by including a high-compactable excipient as described herein.

Specialty grades of highly compactable MCC are available commercially, such as Ceolus™ UF-711, KG-802, and KG-1000 (e.g. by Asahi Kasei). In one embodiment, the highly compactable MCC is Ceolus™ UF-711. In one embodiment, the highly compactable MCC is KG-802 or KG-1000. In one embodiment, the highly compactable MCC is KG-802. In one embodiment, the highly compactable MCC is KG-1000. In one embodiment, the highly compactable MCC is Ceolus™ UF-711 or an equivalent highly compactable MCC. In one embodiment, the highly compactable MCC is KG-802 or KG-1000 or an equivalent highly compactable MCC. In one embodiment, the highly compactable MCC is KG-802 or an equivalent highly compactable MCC. In one embodiment, the highly compactable MCC is KG-1000 or an equivalent highly compactable MCC.

In one embodiment, the highly compactable MCC is present at about: 20% to about 50%; 20% to about 40%; 20 to about 35%; 20% to about 30%; 25% to about 40%; 25% to about 35%; 30% to about 40%; or 30% to about 35% w/w. In one embodiment, the highly compactable MCC is present at an amount of about: 10%, 15%, 20%, 25%, 30%, 35%, 40%, 45%, or 50% w/w. In one embodiment, the highly compactable MCC is present at an amount of about: 10%, 15%, 20%, 25%, 30%, 35%, 40%, 45%, or 50% w/w (±2%). In one embodiment, the highly compactable MCC is present at an amount of about: 10%, 15%, 20%, 25%, 30%, 35%, 40%, 45%, or 50% w/w (±5%).

In one embodiment, the highly compactable MCC is present at an amount of at least about: 10%, 15%, 20%, 25%, 30%, 35%, 40%, 45%, or 50% w/w. In one embodiment, the highly compactable MCC is present at an amount of at least about: 10%, 15%, 20%, 25%, 30%, 35%, 40%, 45%, or 50% w/w (±2%). In one embodiment, the highly compactable MCC is present at an amount of at least about: 10%, 15%, 20%, 25%, 30%, 35%, 40%, 45%, or 50% w/w (±5%).

MCC have unique particle morphology that can give higher compressibility on a unit mass basis. In one embodiment, tablets described herein comprise UF-711 where the UF-711 increases high drug load tablet of Compound 1 compared to tablets without UF-711. Such tablets can have high tablet hardness, and lack difficulty in flowability normally encountered for specialty grades of MCC with high compressibility. Increases in flowability can increase reliability and scalability using dry granulation methods described herein on a commercial manufacturing scale. It was discovered, inter alia, that the high-compactable grade of MCC UF-711 also acts as a binder to hold the granules together. In one embodiment, use of MCC UF-711 obviates the need for an additional excipient specifically with binder function, such as hypromellose.

A comparison of MCC grades is available from the website of Asahi Kasei Ceolus™. Compactibility (used interchangeably with the term compressibility) refers to the extent of plastic deformation the material undergoes upon imposing a mechanical load. At increasing mechanical loads, such as in a hydraulic tablet press, a compressible material will continue to increase in density, as the volume occupied by a given mass is reduced under the load force. Compressible materials yield increasing tensile strength (tablet hardness) as the mechanical load force increases. Incompressible materials reach a plateau in hardness at even low load forces, and the resulting compact or tablet lacks integrity and will fall apart to powder rather than staying intact as a discrete hard compacted mass. "High-compactable" grades of MCC are considered as those yielding higher compactibility than PH-101 or PH-102 common grades of MCC.

The compressibility of UF-711 MCC grade is 50% higher than that of conventional PH-101 grade MCC. In addition, using angle of repose as an indicator of flow properties, the UF-711 grade has better flow than PH-101, and flow equally well as PH-102, despite having increased compactibility than either PH-101 or PH-102. This is unexpected since the high compressibility grades of MCC often have worse flow properties in exchange for increased compactibility. These two properties of UF-711 were surprisingly useful for Compound 1 high drug load blends and tablets since they facilitate high tablet hardness. In one embodiment, the compactibility of UF-711 allows a greater drug load than otherwise expected. In another embodiment, tablets described herein include pharmaceutical excipients such as filler(s) and optionally with a glidant and/or binding agent to prepare a mixture that has compressibility and flowability properties similar to those of UF-711 for use in preparing high strength tablets of Compound 1.

In some embodiments, other grades of microcrystalline cellulose (MCC) known in the art and commercially available can be used. In some embodiments, microcrystalline cellulose (MCC) having a compactability less than UF-711 can be used. In some embodiments, the microcrystalline cellulose is PH-101, PH-102, PH-103, PH-105, PH-112, PH-113, PH-200, PH-310, or PH-302. In some embodiments, the microcrystalline cellulose is PH-101, PH-102, PH-301, PH-302, PH-200, or UF-702. Other grades of microcrystalline cellulose include various Vivapur® and Emcocel® grades of MCC.

In some embodiments, the filler is microcrystalline cellulose, lactose monohydrate, starch, mannitol, sorbitol, dextrose, dibasic calcium phosphate, dicalcium phosphate dihydrate, tricalcium phosphate, calcium phosphate anhydrous lactose, spray-dried lactose, pregelatinized starch, compressible sugar, such as Di-Pac® (Amstar), hydroxypropylmethylcellulose, hydroxypropylmethylcellulose acetate stearate, sucrose-based diluents, confectioner's sugar, monobasic calcium sulfate monohydrate, calcium sulfate dihydrate, calcium lactate trihydrate, dextrates, hydrolyzed cereal solids, amylose, powdered cellulose, calcium carbonate, glycine, kaolin, mannitol, sodium chloride; inositol, bentonite, or combinations thereof.

In one embodiment, the filler is present at about: 20% to about 50%; 20% to about 40%; 20 to about 35%; 20% to about 30%; 25% to about 40%; 25% to about 35%; 30% to about 40%; or 30% to about 35% w/w. In one embodiment, the filler is present at an amount of about: 10%, 15%, 20%, 25%, 30%, 35%, 40%, 45%, or 50% w/w. In one embodiment, the filler is present at an amount of about: 10%, 15%, 20%, 25%, 30%, 35%, 40%, 45%, or 50% w/w (±2%). In one embodiment, the filler is present at an amount of about: 10%, 15%, 20%, 25%, 30%, 35%, 40%, 45%, or 50% w/w (±5%).

In one embodiment, the filler is present at an amount of at least about: 10%, 15%, 20%, 25%, 30%, 35%, 40%, 45%, or 50% w/w. In one embodiment, the filler is present at an amount of at least about: 10%, 15%, 20%, 25%, 30%, 35%, 40%, 45%, or 50% w/w (±2%). In one embodiment, the filler is present at an amount of at least about: 10%, 15%, 20%, 25%, 30%, 35%, 40%, 45%, or 50% w/w (±5%).

The other functional excipients may include disintegrants, lubricants, surfactants, and binders. In one example such excipients include croscarmellose sodium, magnesium stearate, and sodium lauryl sulfate, respectively. In one embodiment, such excipients include croscarmellose sodium, magnesium stearate, colloidal silicon dioxide, and sodium lauryl sulfate. Other useful excipients include those described herein, such as a glidant. In one embodiment, tablets described herein comprise a low percent content (e.g. about <1, 2, 3, 4, 5, or 10%) of one or more excipients on a mass basis.

In certain embodiments, the formulations may also include a disintegrant. A "disintegrant" as used herein refers to an excipient that can breakup or disintegrate the dosage form when it comes in contact with, for example, the gastrointestinal fluid. Suitable disintegrants include, either individually or in combination, starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like. In one embodiment, the disintegrant is carmellose sodium. In one embodiment, the disintegrant is powdered cellulose, microcrystalline cellulose, methylcellulose, or low-substituted hydroxypropylcellulose, or a combination thereof. In one embodiment, the disintegrant is carmellose, carmellose calcium, carmellose sodium or croscarmellose sodium, or a combination thereof. In one embodiment, the disintegrant is croscarmellose sodium. In one embodiment, the disintegrant is colloidal silicon dioxide.

In one embodiment, the disintegrant is present at an amount of about: 0% to about 10%; 0% to about 5%; 0.5% to about 5%; 0.5% to about 2%; 0.75% to about 2%; 0.75% to about 1.5%; 1% to about 5%; or 1% to about 1.5% w/w. In one embodiment, the disintegrant is present at an amount of about 0.25% to about 10%; 0.25% to about 5%; 0.25% to about 4%; 0.25% to about 3.5%; 0.25% to about 3%; 0.25% to about 2.5% w/w, 0.25% to about 2% w/w, or about 0.25% to about 1.5% w/w. In one embodiment, the disintegrant is present at an amount of about: 0.25%, 0.5%, 0.75%, 1%, 1.25%, 1.5%, 2%, 3%, 4%, 5%, 6%, 7%, 8%, 9%, or 10% w/w. In one embodiment, the disintegrant is present at an amount of about: 0.25%, 0.5%, 0.75%, 1%, 1.25%, 1.5%, 2%, 3%, 4%, 5%, 6%, 7%, 8%, 9%, or 10% (±0.1%) w/w. In one embodiment, the disintegrant is present at an amount of about: 0.25%, 0.5%, 0.75%, 1%, 1.25%, 1.5%, 2%, 3%, 4%, 5%, 6%, 7%, 8%, 9%, or 10% (±0.2%) w/w. In one embodiment, the disintegrant is present at an amount of at least about: 0.25%, 0.5%, 0.75%, 1%, 1.25%, 1.5%, 2%, 3%, 4%, 5%, 6%, 7%, 8%, 9%, or 10% w/w. In one embodiment, the disintegrant is present at an amount of at least about: 0.25%, 0.5%, 0.75%, 1%, 1.25%, 1.5%, 2%, 3%, 4%, 5%, 6%, 7%, 8%, 9%, or 10% (±0.1%) w/w. In one embodiment, the disintegrant is present at an amount of at least about: 0.25%, 0.5%, 0.75%, 1%, 1.25%, 1.5%, 2%, 3%, 4%, 5%, 6%, 7%, 8%, 9%, or 10% (±0.2%) w/w. In such embodiments, the disintegrant can be croscarmellose sodium.

In certain embodiments, the formulations may include surfactants (also known as wetting agents). Surfactants are normally selected to maintain the drug or drugs in close association with water, a condition that is believed to improve bioavailability of the composition. Non-limiting examples of surfactants that can be used as wetting agents include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers); polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters; polyoxyethylene sorbitan esters, for example polysorbate 20 and polysorbate 80; propylene glycol fatty acid esters, for example propylene glycol laurate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; sorbitan esters, for example sorbitan monolaurate, sorbitan monooleate, sorbitan monopalmitate and sorbitan monostearate; tyloxapol; and the like.

In one embodiment, the surfactant is sodium lauryl sulfate (SLS). In one embodiment, 1.5% of SLS was used. In vitro dissolution and in vivo beagle dog bioavailability studies demonstrated that where 1.5% SLS was included, complete dissolution of Form II of Compound 1 occurred in vitro, and comparable bioavailability in beagle dogs was achieved relative to formulations that lacked high lubricant levels. Therefore, the sticking properties of Form II of Compound 1 can be minimized and/or eliminated with a high level (e.g. greater than about 0.5, 1, 3, or 5%) of magnesium stearate lubricant. and the potential impact of high lubricant level on drug release was overcome via use of a commonly used surfactant, SLS, at 1.5% w/w, which is an acceptable concentration.

In one embodiment, the surfactant is present at an amount of about: 0.5% to about 5%; 0.5% to about 2.5%; 0.5% to about 2%; 1% to about 5%; 1% to about 2.5%; or 1% to about 1.5% w/w. In one embodiments, the surfactant is present at an amount of about: 0% to about 5%; 0% to about 2%; 0.5% to about 3.5%; 0.5% to about 3%; 0.5% to about 2%; or 0.5% to about 1.5% w/w. In one embodiment, the surfactant is present at an amount of about 1% to about 2%. In one embodiment, the surfactant is present at an amount of about: 0.25%, 0.5%, 0.75%, 1%, 1.25%, 1.5%, 2%, 3%, 4%, or 5% w/w. In one embodiment, the surfactant is present at an amount of about: 0.25%, 0.5%, 0.75%, 1%, 1.25%, 1.5%, 2%, 3%, 4%, or 5% w/w (±0.1%). In one embodiment, the surfactant is present at an amount of about: 0.25%, 0.5%, 0.75%, 1%, 1.25%, 1.5%, 2%, 3%, 4%, or 5% w/w (±0.2%). In one embodiment, the surfactant is present at an amount of at least about: 0.25%, 0.5%, 0.75%, 1%, 1.25%, 1.5%, 2%, 3%, 4%, or 5% w/w. In one embodiment, the surfactant is present at an amount of at least about: 0.25%, 0.5%, 0.75%, 1%, 1.25%, 1.5%, 2%, 3%, 4%, or 5% w/w (±0.1%). In one embodiment, the surfactant is present at an amount of at least about: 0.25%, 0.5%, 0.75%, 1%, 1.25%, 1.5%, 2%, 3%, 4%, or 5% w/w (±0.2%). In one embodiment, the surfactant is present at an amount of less than about 5%, less than about 4%, less than about 3%, or less than about 2%. In such embodiments, the surfactant can be SLS. In some embodiments, the formulations described herein do not include a surfactant.

In certain embodiments, the formulation may contain a lubricant. Lubricants can reduce friction between a tableting mixture and tableting equipment during compression of tablet formulations. Exemplary lubricants include, either individually or in combination, glyceryl behenate; stearic acid and salts thereof, including magnesium, calcium and sodium stearates; hydrogenated vegetable oils; glyceryl palmitostearate; talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like. In one embodiment, the lubricant is stearic acid. In one embodiment, the lubricant is magnesium stearate. In one embodiment, the lubricant is magnesium stearate present in the amount of from about 1.75% to about 2.75% by weight of the tablet. In one embodiment, the lubricant is sodium benzoate, sodium acetate, or sodium fumarate. In one embodiment, the lubricant is polyvinyl alcohol. In one embodiment, the lubricant is sodium lauryl sulfate or magnesium lauryl sulfate.

In one embodiment, the lubricant is present at an amount of about: 0.5% to about 5%; 0.5% to about 2.5%; 0.5% to about 2%; 1% to about 5%; 1% to about 2.5%; 1% to about 2%; 1.75% to about 2.75%; or 2% to about 2.5% w/w. In one embodiment, the lubricant is present at an amount of about: 0.5% to about 5%; 0.5% to about 2.75%, or about 0.5% to about 2%. In one embodiment, the lubricant is present at an amount of about 1.75% to about 2.75%. In one embodiment, the lubricant is present at an amount of about 0.5% to about 2.75%. In one embodiment, the lubricant is present at an amount of about: 0.25%, 0.5%, 0.75%, 1%, 1.25%, 1.5%, 2%, 3%, 4%, or 5% w/w. In one embodiment, the lubricant is present at an amount of about: 0.25%, 0.5%, 0.75%, 1%, 1.25%, 1.5%, 2%, 3%, 4%, or 5% w/w (±0.1%). In one embodiment, the lubricant is present at an amount of about: 0.25%, 0.5%, 0.75%, 1%, 1.25%, 1.5%, 2%, 3%, 4%, or 5% w/w (±0.2%). In one embodiment, the lubricant is present at an amount of at least about: 0.25%, 0.5%, 0.75%, 1%, 1.25%, 1.5%, 2%, 3%, 4%, or 5% w/w. In one embodiment, the lubricant is present at an amount of at least about: 0.25%, 0.5%, 0.75%, 1%, 1.25%, 1.5%, 2%, 3%, 4%, or 5% w/w (±0.1%). In one embodiment, the lubricant is present at an amount of at least about: 0.25%, 0.5%, 0.75%, 1%, 1.25%, 1.5%, 2%, 3%, 4%, or 5% w/w (±0.2%). In such embodiments, the lubricant can be magnesium stearate.

In one embodiment, tablets comprising Form II of Compound 1 comprise a greater level of lubricant (e.g. greater than about 1%) compared to standard tablets. The greater levels of magnesium stearate lubricant can increase hydrophobicity of pharmaceutical preparations.

In certain embodiments, the formulation may include a binder. Binding agents or adhesives are useful excipients, particularly where the composition is in the form of a tablet. Such binding agents or adhesives should impart sufficient cohesion to the blend being tableted to allow for normal processing operations such as sizing, lubrication, compression and packaging, but still allow the tablet to disintegrate and the composition to be absorbed upon ingestion. Exemplary binding agents and adhesives include, individually or in combination, acacia; tragacanth; glucose; polydextrose; starch including pregelatinized starch; gelatin; modified celluloses including methylcellulose, carmellose sodium, hydroxypropylmethylcellulose (HPMC or hypromellose), hydroxypropyl-cellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; and the like.

In one embodiment, one or more binding agents, if present, comprise about 0.1% to about 25%, for example about 0.1% to about 10%, about 0.1% to about 5%, or about 0.1% to about 2%, by weight of the composition. In one embodiment, one or more binding agents, if present, comprise about: 0.1%, 0.2%, 0.3%, 0.4%, 0.5%, 0.75%, 1%, 2%, 3%, 4%, 5%, 6%, 7%, 8%, 9%, or 10% w/w. In one embodiment, UF-711 is used in a percentage weight disclosed herein and provides granule binding properties sufficient to hold compacts intact through granule milling. Thus, in particular embodiments, tablets described herein include UF-711 in an amount wherein UF-711 acts as a filler and a binder.

In certain embodiments, the formulation may contain a glidant. Glidants are frequently used to improve flow properties and reduce static in a tableting mixture. Exemplary glidants include, either individually or in combination, colloidal silicon dioxide, starch, powdered cellulose, sodium lauryl sulfate, magnesium trisilicate and metallic stearates. In some embodiments, the glidant is talc. In some embodiments, the glidant is colloidal silicon dioxide.

In one embodiment, one or more glidants, if present, comprise about 0.1% to about 10%, for example about 0.1% to about 5%, or about 0.1% to about 2%, by weight of the composition. In one embodiment, one or more glidants, if present, comprise about: 0.1%, 0.2%, 0.3%, 0.4%, 0.5%, 0.75%, 1%, 2%, 3%, 4%, 5%, 6%, 7%, 8%, 9%, or 10% w/w. In one embodiment, one or more glidants, if present, comprise about 0.01% to about 2% w/w. In some embodiments, the glidant is not more than about 9%, 8%, 7%, 6% or 5% w/w. In some embodiments, the glidant is less than about 3% w/w, 2.5% w/w, or 2% w/w. In some embodiments, the glidant is less than about 2% w/w. In some embodiments, the glidant is in an amount of about 0.75% by weight of the tablet. In one embodiment, the glidant is Talc and colloidal silicon dioxide, either individually or in combination. In particular embodiments, tablets described herein do not comprise a glidant or flow aid. In certain embodiments, adequate blend flowability for purposes of feeding to the compaction zone in, for example, a pharmaceutical roller compaction dry granulation machine during manufacture is obtained in the absence of a glidant or flow aid. In one embodiment, the glidant is added to both the intragranular component and the extrangranular component or to one of the granular components.

Other excipients such as colorants (coloring agents), coating polymers, flavors (flavoring agents) and sweeteners are known in the pharmaceutical art and can be used in compositions of the present disclosure. In one embodiment, tablets described herein include a coating surrounding the core described herein comprising Compound 1. Tablets can be coated using formulations known in the art, such as for example, excipients such as talc, polyvinyl alcohol, and PEG (e.g., PEG 4000 and PEG 6000). In some embodiments, the coating polymer can be hydroxypropyl methylcellulose (HPMC). When coated, tablets comprise a core that is coated with a nonfunctional film or a release-modifying or enteric coating.

In some embodiments, tablets described herein comprise a sweetener (also known as a sweetening agent). In some embodiments, the sweetener may improve the palatability of the tablet by reducing bitterness and thereby improving the acceptability of the formulation for patients, such as a patient about 9 months old to about 11 years old. Non-limiting examples of a sweetener are sucrose, xylitol, maltitol, mannitol, sorbitol, sucralose, sodium saccharin, acesulfame potassium, aspartame, and others known to those skilled in the art. In some embodiments, one or more sweeteners can be used. In some embodiments, the sweetener is sucralose.

In some embodiments, one or more sweeteners, if present, comprise about 2% to about 20% or about 0.1% to about 10%, for example about 0.1% to about 5%, or about 0.1% to about 3%, by weight of the composition. In one embodiment, one or more sweeteners, if present, comprise about: 0.1%, 0.2%, 0.3%, 0.4%, 0.5%, 0.75%, 1%, 2%, 3%, 4%, 5%, 6%, 7%, 8%, 9%, or 10% w/w.

Also provided herein are tablets as described herein further comprising a flavoring agent. The flavoring agent may enhance the flavor of the tablet to increase its palatability for patients. A flavoring agent includes but is not limited to Grape, Orange, Cherry, Mango, and Tropical. In some embodiments, a flavoring agent is from an artificial origin, a natural origin, or a combination of natural and artificial origins. In some embodiments, one or more flavoring agents can be used. In some embodiments, the flavoring agent is an artificial grape flavor.

In some embodiments, one or more flavoring agent, if present, comprise about 1% to about 5% or about 0.1% to about 10%, for example about 0.1% to about 5%, or about 0.1% to about 3%, by weight of the composition. In one embodiment, one or more flavoring agents, if present, comprise about: 0.1%, 0.2%, 0.3%, 0.4%, 0.5%, 0.75%, 1%, 2%, 3%, 4%, 5%, 6%, 7%, 8%, 9%, or 10% w/w.

Also provided herein are tablets as described herein further comprising a coloring agent. Coloring agents may be used to enhance the appearance of the tablet. Non-limiting examples of a coloring agent are dyes and pigments, including but not limited to iron oxide pigment. In some embodiments, the coloring agent is iron oxide yellow.

In some embodiments, one or more coloring agents, if present, comprise about 0% to about 1%, 0.1% to about 10%, for example about 0.1% to about 5%, or about 0.1% to about 3%, by weight of the composition. In one embodiment, one or more coloring agents, if present, comprise about: 0.1%, 0.2%, 0.3%, 0.4%, 0.5%, 0.75%, 1%, 2%, 3%, 4%, 5%, 6%, 7%, 8%, 9%, or 10% w/w.

Further provided herein is a tablet comprising a granular component wherein the granular component comprises:
  (i) about 60% by weight of Compound 1;
  (ii) a high-compactable microcrystalline cellulose as described herein;
  (iii) optionally a disintegrant as described herein;
  (iv) a lubricant as described herein;
  (v) optionally a surfactant as described herein; and
  (vi) optionally a binder as described herein;
wherein the percentage by weight is relative to the total weight of the tablet.

Further provided herein is a tablet comprising a granular component wherein the granular component comprises:
  (i) about 60% by weight of Compound 1;
  (ii) a high-compactable microcrystalline cellulose as described herein;
  (iii) optionally a disintegrant as described herein;
  (iv) a lubricant as described herein;

(v) optionally a surfactant as described herein;
(vi) optionally a binder as described herein; and
(vii) optionally a glidant as described herein;
wherein the percentage by weight is relative to the total weight of the tablet.

In one embodiment, the granular component comprises:
(i) a high-compactable microcrystalline cellulose as described herein in the amount of about 27.50% by weight of the tablet;
(ii) a disintegrant as described herein is present in the amount of about 1% by weight of the tablet; and
(iii) a lubricant as described herein is present in the amount of about 1.50% by weight of the tablet.

In one embodiment, the granular component comprises:
(i) high-compactable microcrystalline cellulose as described herein at an amount of about 27.50±2% by weight of the tablet;
(ii) a disintegrant as described herein at an amount of about 1±0.2% by weight of the tablet; and
(iii) a lubricant as described herein at an amount of about 1.50±0.2% by weight of the tablet.

In one embodiment, the intragranular component comprises:
(i) high-compactable microcrystalline cellulose as described herein at an amount of 27%±2% by weight of the tablet;
(ii) disintegrant as described herein at an amount of 1%±0.2% by weight of the tablet;
(iii) lubricant as described herein at an amount of 1.5%±0.2% by weight of the tablet; and
(iv) glidant at an amount of 0.5%±0.2% by weight of the tablet.

The high-compactable microcrystalline cellulose of such granular components can be Ceolus™ UF-711. The disintegrant of such granular components can be croscarmellose sodium. The lubricant of such granular components can be magnesium stearate. Compound 1 of such granular components can be a substantially pure crystalline ansolvate form characterized by at least two, three or four X-ray powder diffraction peaks (Cu Kα radiation) selected from 13.37°, 14.37°, 19.95° and 23.92° 2θ (each ±0.2° 2θ), preferably 2 Compound 1 is 95% in crystalline ansolvate form characterized by at least two, three, or four X-ray powder diffraction peaks (Cu Kα radiation) selected from 13.37°, 14.37°, 19.95° and 23.92° 2θ (each ±0.2° 2θ) and 5% in Form I and/or Form N; and surfactant is absent.

In some embodiments, the high-compactable microcrystalline cellulose is Ceolus™ UF-711; the disintegrant is croscarmellose sodium; the lubricant is magnesium stearate; Compound 1 is a substantially pure crystalline ansolvate form characterized by at least two X-ray powder diffraction peaks (Cu Kα radiation) selected from 13.37°, 14.37°, 19.95° and 23.92° 2θ (each ±0.2° 2θ); and the surfactant is absent.

Further provided herein is a tablet comprising a granular component wherein the granular component consists essentially of:
(i) about 60% by weight of Compound 1;
(ii) a high-compactable microcrystalline cellulose as described herein;
(iii) optionally a disintegrant as described herein;
(iv) a lubricant as described herein;
(v) optionally a surfactant as described herein; and
(vi) optionally a binder as described herein;
wherein the percentage by weight is relative to the total weight of the tablet.

Further provided herein is a tablet comprising a granular component wherein the granular component consists essentially of:
(i) about 60% by weight of Compound 1;
(ii) a high-compactable microcrystalline cellulose as described herein;
(iii) optionally a disintegrant as described herein;
(iv) a lubricant as described herein;
(v) optionally a surfactant as described herein;
(vi) optionally a binder as described herein; and
(vii) optionally a glidant;
wherein the percentage by weight is relative to the total weight of the tablet.

In one embodiment, the granular component comprises:
(i) a high-compactable microcrystalline cellulose as described herein in the amount of about 27.50% by weight of the tablet;
(ii) a disintegrant as described herein an amount of about 1% by weight of the tablet; and
(iii) a lubricant as described herein in an amount of about 1.50% by weight of the tablet; and
(iv) optionally about 1.5% by weight of a surfactant as described herein.

In one embodiment, the granular component comprises:
(i) the amount of high-compactable microcrystalline cellulose is about 27.50% by weight of the tablet;
(ii) the amount of disintegrant is about 1% by weight of the tablet;
(iii) the amount of lubricant is about 1.50% by weight of the tablet; and
(iv) optionally, the amount of surfactant is about 1.5% by weight of the tablet.

In one embodiment, the intragranular component comprises:
(i) a high-compactable microcrystalline cellulose as described herein in the amount of about 27% by weight of the tablet;
(ii) a disintegrant as described herein an amount of about 1% by weight of the tablet; and
(iii) a lubricant as described herein in an amount of about 1.50% by weight of the tablet;
(iv) optionally about 1.5% by weight of a surfactant as described herein; and
(v) optionally about 0.5% by weight of a glidant as described herein.

In another embodiment, the granular component comprises:
(i) a high-compactable microcrystalline cellulose as described herein in an amount of about 27.50±2% by weight of the tablet;
(ii) a disintegrant as described herein is 1±0.2% by weight of the tablet;
(iii) a lubricant as described herein is 1.50±0.2% by weight of the tablet; and
(iv) surfactant as described herein is absent.

In another embodiment, the intragranular component comprises:
(i) a high-compactable microcrystalline cellulose as described herein in an amount of about 27%±2% by weight of the tablet;
(ii) a disintegrant as described herein is 1±0.2% by weight of the tablet;
(iii) a lubricant as described herein is 1.50±0.2% by weight of the tablet;
(iv) surfactant as described herein is absent; and
(v) optionally about 0.5% by weight of a glidant as described herein.

The high-compactable microcrystalline cellulose of such granular components can be Ceolus™ UF-711. The disintegrant of such granular components can be croscarmellose sodium. The lubricant of such granular components can be magnesium stearate. The Compound 1 of such granular components can be a substantially pure crystalline ansolvate form characterized by at least two, three or four X-ray powder diffraction peaks (Cu Kα radiation) selected from 13.37°, 14.37°, 19.95° and 23.92° 2θ (each ±0.2° 2θ), preferably 2 Compound 1 is 95% in crystalline ansolvate form characterized by at least two, three, or four X-ray powder diffraction peaks (Cu Kα radiation) selected from 13.37°, 14.37°, 19.95° and 23.92° 2θ (each ±0.2° 2θ) and 5% in Form I and/or Form N and the surfactant is absent.

In certain embodiments, the tablets described herein further comprise an extragranular component, which comprises:
(i) a microcrystalline cellulose as described herein;
(ii) a disintegrant as described herein;
(iii) optionally a surfactant as described herein;
(iv) a lubricant as described herein; and
(v) optionally a coating as described herein;
provided that at least one of the intragranular or extragranular component of the tablet contains a surfactant.

In certain embodiments, the tablets described herein further comprise an extragranular component, which comprises:
(i) a microcrystalline cellulose as described herein;
(ii) a disintegrant as described herein;
(iii) optionally a surfactant as described herein;
(iv) a lubricant as described herein;
(v) optionally a coating as described herein; and
(vi) optionally a glidant as described herein;
provided that at least one of the intragranular or extragranular component of the tablet contains a surfactant.

In certain embodiments, extragranular components described herein do not include Compound 1.

In one embodiment, the extragranular component comprises:
(i) an amount of extragranular microcrystalline cellulose as described herein of about 7.50% by weight of the tablet;
(ii) an amount of extragranular disintegrant as described herein of about 0.25% by weight of the tablet;
(iii) a surfactant as described herein in an amount of about 1.50% by weight of the tablet; and
(iv) an amount of extragranular lubricant as described herein of about 0.75% by weight of the tablet.

In one embodiment, the extragranular component comprises:
(i) an amount of extragranular microcrystalline cellulose as described herein of about 7.50% by weight of the tablet;
(ii) an amount of extragranular disintegrant as described herein of about 0.25% by weight of the tablet;
(iii) a surfactant as described herein in an amount of about 1.50% by weight of the tablet;
(iv) an amount of extragranular lubricant as described herein of about 0.75% by weight of the tablet; and
(v) optionally a glidant.

In one embodiment, the extragranular component comprises:
(i) an extragranular microcrystalline cellulose in the amount of about 5% to about 10% by weight of the tablet;
(ii) an extragranular disintegrant in the amount of about 0.1% to about 0.5% by weight of the tablet;
(iii) a surfactant in the amount of about 1% to about 2% by weight of the tablet; and
(iv) an extragranular lubricant in the amount of about 0.5% to about 1% by weight of the tablet.

The microcrystalline cellulose of the extragranular component can be a high-compactable microcrystalline cellulose selected from Ceolus™ UF-711, Ceolus™ KG-1000 or KG-802, preferably Ceolus™ UF-711. The disintegrant of the extragranular component can be croscarmellose sodium. The lubricant of the extragranular component can be magnesium stearate. The surfactant of the extragranular component can be sodium lauryl sulfate.

In one embodiment, the extragranular component consists essentially of:
(i) a microcrystalline cellulose as described herein;
(ii) a disintegrant as described herein;
(iii) optionally a surfactant as described herein;
(iv) a lubricant as described herein; and
(v) optionally a coating as described herein;
provided that at least one of the intragranular or extragranular component of the tablet contains a surfactant.

In one embodiment, the extragranular component consists essentially of:
(i) a microcrystalline cellulose as described herein;
(ii) a disintegrant as described herein;
(iii) optionally a surfactant as described herein;
(iv) a lubricant as described herein;
(v) optionally a coating as described herein; and
(vi) optionally a glidant as described herein;
provided that at least one of the intragranular or extragranular component of the tablet contains a surfactant.

In one embodiment, the extragranular component comprises:
(i) an amount of extragranular microcrystalline cellulose as described herein of about 7.50% by weight of the tablet;
(ii) an amount of extragranular disintegrant as described herein of about 0.25% by weight of the tablet;
(iii) a surfactant is present and the amount as described herein is of about 1.50% by weight of the tablet; and
(iv) an amount of extragranular lubricant as described herein of about 0.75% by weight of the tablet.

In one embodiment, the extragranular component described herein comprises:
(i) an extragranular microcrystalline cellulose in the amount of about 5% to about 10% by weight of the tablet;
(ii) an extragranular disintegrant in the amount of about 0.1% to about 0.5% by weight of the tablet;
(iii) a surfactant in the amount of about 1% to about 2% by weight of the tablet; and
(iv) an extragranular lubricant in the amount of about 0.5% to about 1% by weight of the tablet.

The microcrystalline cellulose of the extragranular component can be a high-compactable microcrystalline cellulose. The microcrystalline cellulose of the extragranular component can be a high-compactable microcrystalline cellulose Ceolus™ UF-711. The disintegrant of the extragranular component can be croscarmellose sodium. The lubricant of the extragranular component can be magnesium stearate. The surfactant of the extragranular component can be sodium lauryl sulfate.

Further provided herein is a tablet comprising:
(i) an intragranular component comprising:
(a) 60% by weight of 2-hydroxy-6-((2-(1-isopropyl-1H-pyrazol-5-yl)pyridin-3-yl)methoxy)benzaldehyde as a crystalline form characterized by two, three or four X-ray powder diffraction peaks (Cu Kα radiation) selected from 13.37°, 14.37°, 19.95° and 23.92° 2θ (each ±0.2° 2θ);
    (b) 27.50% by weight of microcrystalline cellulose Ceolus™ UF-711;
    (c) 1.0% by weight of Croscarmellose Sodium; and
    (d) 1.50% by weight of Magnesium Stearate; and
  (ii) an extragranular component comprising:
    (a) 9.0% by weight of microcrystalline cellulose Ceolus™ UF-711;
    (b) 0.25% by weight of Croscarmellose Sodium; and
    (c) 0.75% by weight of Magnesium Stearate;
wherein the percentage by weight is relative to the total weight of the tablet.

Further provided herein is a tablet comprising:
  (i) an intragranular component comprising:
    (a) 60% by weight of 2-hydroxy-6-((2-(1-isopropyl-1H-pyrazol-5-yl)pyridin-3-yl)methoxy)benzaldehyde as a crystalline form characterized by two, three or four X-ray powder diffraction peaks (Cu Kα radiation) selected from 13.37°, 14.37°, 19.95° and 23.92° 2θ (each ±0.2° 2θ);
    (b) 27.50% by weight of microcrystalline cellulose Ceolus™ UF-711;
    (c) 1.0% by weight of Croscarmellose Sodium; and
    (d) 1.50% by weight of Magnesium Stearate; and
  (ii) an extragranular component comprising:
    (a) 7.50% by weight of microcrystalline cellulose Ceolus™ UF-711;
    (b) 0.25% by weight of Croscarmellose Sodium;
    (c) 0.75% by weight of Magnesium Stearate; and
    (d) 1.50% by weight Sodium Lauryl Sulfate;
wherein the percentage by weight is relative to the total weight of the tablet.

The tablets described herein having inter- and extragranular components can contain amounts of Compound 1 as described herein (e.g. about 300 mg to about 900 mg; or about 300, 400, 500, 750, or 900 mg).

Further provided herein is a tablet comprising a granular component wherein the granular component comprises:
  (i) about 30% to about 70% by weight of Compound 1;
  (ii) a filler;
  (iii) a disintegrant;
  (iv) a glidant;
  (v) a lubricant;
  (vi) optionally a surfactant; and
  (vii) optionally a binder;
wherein the percentage by weight is relative to the total weight of the tablet.

Further provided herein is a tablet comprising a granular component wherein the granular component comprises:
  (i) about 60% by weight of Compound 1;
  (ii) a filler;
  (iii) a disintegrant;
  (iv) a glidant;
  (v) a lubricant;
  (vi) optionally a surfactant; and
  (vii) optionally a binder;
wherein the percentage by weight is relative to the total weight of the tablet.

Some embodiments provide for a tablet comprising a granular component wherein the granular component comprises:
  (i) about 60% by weight of Compound 1;
  (ii) about 27.5% by weight of filler;
  (iii) about 1% by weight of disintegrant;
  (iv) about 1.25% by weight of glidant;
  (v) about 1.5% by weight of lubricant;
  (vi) optionally about 1.5% by weight of surfactant; and
  (vii) optionally a binder;
wherein the percentage by weight is relative to the total weight of the tablet.

Some embodiments provide for a tablet comprising a granular component wherein the granular component comprises:
  (i) about 60% by weight of Compound 1;
  (ii) about 27.5% by weight of filler;
  (iii) about 1% by weight of disintegrant;
  (iv) about 1.25% by weight of glidant;
  (v) about 1.5% by weight of lubricant;
  (vi) optionally about 2.5% by weight of sweetener;
  (vii) optionally about 0.5% by weight of flavoring agent; and
  (viii) optionally about 0.2% by weight of colorant.
wherein the percentage by weight is relative to the total weight of the tablet.

In one embodiment, provided herein is a dispersible tablet that comprises:
  (i) about 50% to about 70% by weight of Compound 1;
  (ii) about 20% to about 35% by weight of filler;
  (iii) about 1% to about 2% by weight of disintegrant;
  (iv) less than about 2% by weight of glidant;
  (v) about 1% to about 5% by weight of lubricant;
  (vi) optionally a sweetener;
  (vii) optionally a flavoring agent; and
  (viii) optionally a coloring agent;
wherein the percentage by weight is relative to the total weight of the tablet.

In one embodiment, provided herein is a dispersible tablet that comprises:
  (i) about 50% to about 70% by weight of Compound 1;
  (ii) about 20% to about 35% by weight of filler;
  (iii) about 1% to about 2% by weight of disintegrant;
  (iv) less than about 2% by weight of glidant;
  (v) about 1% to about 5% by weight of lubricant;
  (vi) optionally about 1% to about 3% by weight of sweetener;
  (vii) optionally about 0.2% to about 1.5% by weight of flavoring agent; and
  (viii) optionally about 0.1% to about 1% by weight of coloring agent;
wherein the percentage by weight is relative to the total weight of the tablet.

In one embodiment, provided herein is a tablet that comprises:
  (i) about 50% to about 65% by weight of Compound 1;
  (ii) a filler;
  (iii) a surfactant; and
  (iv) about 0.01% to about 2% by weight of glidant;
wherein the percentage by weight is relative to the total weight of the tablet.

In one embodiment, provided herein is a tablet that comprises:
  (i) about 50% to about 65% by weight of Compound 1;
  (ii) about 20% to about 35% by weight of filler;
  (iii) about 0.5% to about 2% by weight of surfactant; and
  (iv) about 0.01% to about 2% by weight of glidant;
wherein the percentage by weight is relative to the total weight of the tablet.

Also provided herein are dispersible tablets, wherein the tablets rapidly disintegrate in a small amount of liquid for administration to a patient. In some embodiments, tablets described herein may be crushed and mixed with an appropriate vehicle, such as food, for administration to a patient.

Tablets as described herein may be useful for pediatric patients or patients that have difficulty swallowing capsules or tablets.

In some embodiments, the dispersible tablets provided herein disintegrate in a liquid in less than about 5 minutes, about 4 minutes, about 3 minutes, about 2 minutes, or about 1 minute. In some embodiments, the dispersible tablet disintegrates in a liquid in less than 1 minute.

In some embodiments, the tablet rapidly disintegrates in less than about 15 mL, about 14 mL, about 13 mL, about 12 mL, about 11 mL, 10 mL, about 9 mL, about 8 mL, about 6 mL, or about 5 mL of liquid. In some embodiments, the tablet rapidly disintegrates in about 10 mL, about 9 mL, about 8 mL, about 6 mL, or about 5 mL of liquid. In some embodiments, the tablet rapidly disintegrates in less than about 5 mL, about 4 mL, or 3 mL of liquid.

In one embodiment, provided herein is a dispersible tablet comprising:
  (i) about 30% to about 70% by weight of Compound 1;
  (ii) filler;
  (iii) disintegrant;
  (iv) glidant; and
  (v) a lubricant;
wherein the percentage by weight is relative to the total weight of the tablet.

In one embodiment, provided herein is a dispersible tablet comprising:
  (i) about 60% by weight of Compound 1;
  (ii) filler;
  (iii) disintegrant;
  (iv) glidant; and
  (v) a lubricant;
wherein the percentage by weight is relative to the total weight of the tablet.

In one embodiment, provided herein is a tablet that comprises:
  (i) about 30% to about 70% by weight of Compound 1;
  (ii) a filler;
  (iii) a disintegrant;
  (iv) a glidant;
  (v) a lubricant;
  (vi) a surfactant; and
  (vii) optionally a binder;
wherein the amount of disintegrant to filler is in a ratio of about 1:28 and wherein the percentage by weight is relative to the total weight of the tablet.

In one embodiment, provided herein is a tablet that comprises:
  (i) about 30% to about 70% by weight of Compound 1;
  (ii) a filler;
  (iii) less than about 2% by weight of disintegrant;
  (iv) a glidant;
  (v) a lubricant;
  (vi) a surfactant; and
  (vii) optionally a binder;
wherein the amount of disintegrant to filler is in a ratio of about 1:28, and wherein the percentage by weight is relative to the total weight of the tablet.

In one embodiment, provided herein is a tablet that comprises:
  (i) about 60% by weight of Compound 1;
  (ii) a filler;
  (iii) a disintegrant;
  (iv) a glidant;
  (v) a lubricant
  (vi) a surfactant; and
  (vii) optionally a binder;

wherein the amount of disintegrant to filler is in a ratio of about 1:28, and wherein the percentage by weight is relative to the total weight of the tablet.

In one embodiment, provided herein is a tablet that comprises:
  (i) about 60% by weight of Compound 1;
  (ii) a filler;
  (iii) less than about 2% by weight of disintegrant;
  (iv) a glidant;
  (v) a lubricant
  (vi) a surfactant; and
  (vii) optionally a binder;
wherein the amount of disintegrant to filler is in a ratio of about 1:28, and wherein the percentage by weight is relative to the total weight of the tablet.

In one embodiment, provided herein is a tablet that comprises:
  (i) about 30% to about 70% by weight of Compound 1;
  (ii) a filler;
  (iii) a disintegrant;
  (iv) a lubricant;
  (v) a surfactant; and
  (vi) optionally a binder;
wherein the amount of disintegrant to filler is in a ratio of about 1:28, and wherein the percentage by weight is relative to the total weight of the tablet.

In one embodiment, provided herein is a tablet that comprises:
  (i) about 30% to about 70% by weight of Compound 1;
  (ii) a filler;
  (iii) less than about 2% by weight of disintegrant;
  (iv) a lubricant;
  (v) a surfactant; and
  (vi) optionally a binder;
wherein the amount of disintegrant to filler is in a ratio of about 1:28, and wherein the percentage by weight is relative to the total weight of the tablet.

In one embodiment, provided herein is a tablet that comprises:
  (i) about 60% by weight of Compound 1;
  (ii) a filler;
  (iii) a disintegrant;
  (iv) a lubricant;
  (v) a surfactant; and
  (vi) optionally a binder;
wherein the amount of disintegrant to filler is in a ratio of about 1:28, and wherein the percentage by weight is relative to the total weight of the tablet.

In one embodiment, provided herein is a tablet that comprises:
  (i) about 60% by weight of Compound 1;
  (ii) a filler;
  (iii) less than about 2% by weight of disintegrant;
  (iv) a lubricant;
  (v) a surfactant; and
  (vi) optionally a binder;
wherein the amount of disintegrant to filler is in a ratio of about 1:28, and wherein the percentage by weight is relative to the total weight of the tablet.

In some embodiments, the amount of disintegrant to filler is in ratio of about 0:35, 1:60; about 1:56; about 1:55; about 1:50; about 1:45; about 1:40; about 1:35; about 1:30; about 1:25; about 1:20; about 1:15; about 1:10; about 1:7; and about 1:5. In some embodiments, the amount of disintegrant to filler is in ratio of between about 0:35 to about 1:5. In some embodiments, the amount of disintegrant to filler is in ratio of between about 0:35 to about 1:7. In some embodiments, the amount of disintegrant to filler is in ratio of between about 1:60 to about 1:7. In some embodiments, the amount of disintegrant to filler is in ratio of between about 1:56 to about 1:7. In some embodiments, the amount of disintegrant to filler is in ratio of between about 1:50 to about 1:10. In some embodiments, the amount of disintegrant to filler is in ratio of between about 1:40 to about 1:20. In some embodiments, the amount of disintegrant to filler is in ratio of between about 1:25 to about 1:35. In some embodiments, the amount of disintegrant to filler is in ratio of about 1:30. In some embodiments, the amount of disintegrant to filler is in ratio of about 1:29. In some embodiments, the amount of disintegrant to filler is in ratio of about 1:28. In some embodiments, the amount of disintegrant to filler is in ratio of about 1:27. In some embodiments, the amount of disintegrant to filler is in ratio of about 1:26. In some embodiments, the amount of disintegrant to filler is in ratio of about 1:25.

In one embodiment, provided herein is a dispersible tablet that comprises:
(i) about 30% to about 70% by weight of Compound 1;
(ii) about 20% to about 35% by weight of filler;
(iii) about 1% to about 2% by weight of disintegrant;
(iv) less than about 2% by weight of glidant; and
(v) a lubricant;
wherein the percentage by weight is relative to the total weight of the tablet and wherein the dispersible tablet disintegrates in a liquid in less than 1 minute.

In one embodiment, provided herein is a dispersible tablet that comprises:
(i) about 30% to about 70% by weight of Compound 1;
(ii) about 20% to about 35% by weight of filler;
(iii) about 1% to about 2% by weight of disintegrant;
(iv) less than about 2% by weight of glidant; and
(v) about 1% to about 5% by weight of lubricant;
wherein the percentage by weight is relative to the total weight of the tablet and wherein the dispersible tablet disintegrates in a liquid in less than 1 minute.

In one embodiment, provided herein is a dispersible tablet that comprises:
(i) about 50% to about 70% by weight of Compound 1;
(ii) about 20% to about 35% by weight of filler;
(iii) about 1% to about 2% by weight of disintegrant;
(iv) less than about 2% by weight of glidant; and
(v) a lubricant;
wherein the percentage by weight is relative to the total weight of the tablet and wherein the dispersible tablet disintegrates in a liquid in less than 1 minute.

In one embodiment, provided herein is a dispersible tablet that comprises:
(i) about 50% to about 70% by weight of Compound 1;
(ii) about 20% to about 35% by weight of filler;
(iii) about 1% to about 2% by weight of disintegrant;
(iv) less than about 2% by weight of glidant; and
(v) about 1% to about 5% by weight of lubricant;
wherein the percentage by weight is relative to the total weight of the tablet and wherein the dispersible tablet disintegrates in a liquid in less than 1 minute.

In one embodiment, provided herein is a dispersible tablet that comprises:
(i) about 60% by weight of Compound 1;
(ii) about 20% to about 35% by weight of filler;
(iii) about 1% to about 2% by weight of disintegrant;
(iv) less than about 2% by weight of glidant; and
(v) a lubricant;
wherein the percentage by weight is relative to the total weight of the tablet and wherein the dispersible tablet disintegrates in a liquid in less than 1 minute.

In one embodiment, provided herein is a dispersible tablet that comprises:
(i) about 60% by weight of Compound 1;
(ii) about 20% to about 35% by weight of filler;
(iii) about 1% to about 2% by weight of disintegrant;
(iv) less than about 2% by weight of glidant; and
(v) about 1% to about 5% by weight of lubricant;
wherein the percentage by weight is relative to the total weight of the tablet and wherein the dispersible tablet disintegrates in a liquid in less than 1 minute.

In one embodiment, provided herein is a dispersible tablet that comprises:
(i) about 30% to about 70% by weight of Compound 1;
(ii) about 20% to about 35% by weight of filler;
(iii) about 1% to about 2% by weight of disintegrant;
(iv) less than about 2% by weight of glidant; and
(v) a lubricant;
wherein the percentage by weight is relative to the total weight of the tablet.

In one embodiment, provided herein is a dispersible tablet that comprises:
(i) about 30% to about 70% by weight of Compound 1;
(ii) about 20% to about 35% by weight of filler;
(iii) about 1% to about 2% by weight of disintegrant;
(iv) less than about 2% by weight of glidant; and
(v) about 1% to about 5% by weight of lubricant;
wherein the percentage by weight is relative to the total weight of the tablet.

In one embodiment, provided herein is a dispersible tablet that comprises:
(i) about 50% to about 70% by weight of Compound 1;
(ii) about 20% to about 35% by weight of filler;
(iii) about 1% to about 2% by weight of disintegrant;
(iv) less than about 2% by weight of glidant; and
(v) a lubricant;
wherein the percentage by weight is relative to the total weight of the tablet.

In one embodiment, provided herein is a dispersible tablet that comprises:
(i) about 50% to about 70% by weight of Compound 1;
(ii) about 20% to about 35% by weight of filler;
(iii) about 1% to about 2% by weight of disintegrant;
(iv) less than about 2% by weight of glidant; and
(v) about 1% to about 5% by weight of lubricant;
wherein the percentage by weight is relative to the total weight of the tablet.

In one embodiment, provided herein is a dispersible tablet that comprises:
(i) about 60% by weight of Compound 1;
(ii) about 20% to about 35% by weight of filler;
(iii) about 1% to about 2% by weight of disintegrant;
(iv) less than about 2% by weight of glidant; and
(v) a lubricant;
wherein the percentage by weight is relative to the total weight of the tablet.

In one embodiment, provided herein is a dispersible tablet that comprises:
(i) about 60% by weight of Compound 1;
(ii) about 20% to about 35% by weight of filler;
(iii) about 1% to about 2% by weight of disintegrant;
(iv) less than about 2% by weight of glidant; and
(v) about 1% to about 5% by weight of lubricant;
wherein the percentage by weight is relative to the total weight of the tablet.

In some embodiments, the dispersible tablet further comprises a sweetener, a colorant, a flavoring agent, or a combination thereof.

In one embodiment, provided herein is a dispersible tablet that comprises:
(i) about 30% to about 70% by weight of Compound 1;
(ii) about 20% to about 35% by weight of filler;
(iii) about 1% to about 2% by weight of disintegrant;
(iv) less than about 2% by weight of glidant;
(v) a lubricant;
(vi) a sweetener;
(vii) a flavoring agent; and
(viii) a coloring agent;
wherein the percentage by weight is relative to the total weight of the tablet and wherein the dispersible tablet disintegrates in a liquid in less than 1 minute.

In one embodiment, provided herein is a dispersible tablet that comprises:
(i) about 50% to about 70% by weight of Compound 1;
(ii) about 20% to about 35% by weight of filler;
(iii) about 1% to about 2% by weight of disintegrant;
(iv) less than about 2% by weight of glidant;
(v) a lubricant;
(vi) a sweetener;
(vii) a flavoring agent; and
(viii) a coloring agent;
wherein the percentage by weight is relative to the total weight of the tablet and wherein the dispersible tablet disintegrates in a liquid in less than 1 minute.

In one embodiment, provided herein is a dispersible tablet that comprises:
(i) about 60% by weight of Compound 1;
(ii) about 20% to about 35% by weight of filler;
(iii) about 1% to about 2% by weight of disintegrant;
(iv) less than about 2% by weight of glidant;
(v) a lubricant;
(vi) a sweetener;
(vii) a flavoring agent; and
(viii) a coloring agent;
wherein the percentage by weight is relative to the total weight of the tablet and wherein the dispersible tablet disintegrates in a liquid in less than 1 minute.

In one embodiment, provided herein is a dispersible tablet that comprises:
(i) about 60% by weight of Compound 1 Form II;
(ii) about 20% to about 35% by weight of filler;
(iii) about 1% to about 2% by weight of disintegrant;
(iv) less than about 2% by weight of glidant;
(v) about 1% to about 5% by weight of lubricant;
(vi) a sweetener;
(vii) a flavoring agent; and
(viii) a coloring agent;
wherein the percentage by weight is relative to the total weight of the tablet and wherein the dispersible tablet disintegrates in a liquid in less than 1 minute.

In one embodiment, provided herein is a dispersible tablet that comprises:
(i) about 60% by weight of Compound 1 Form II;
(ii) about 20% to about 35% by weight of filler;
(iii) about 1% to about 2% by weight of disintegrant;
(iv) less than about 2% by weight of glidant;
(v) about 1% to about 5% by weight of lubricant;
(vi) about 1% to about 3% by weight of sweetener;
(vii) about 0.2% to about 1.5% by weight of flavoring agent; and
(viii) about 0.1% to about 1% by weight of coloring agent;
wherein the percentage by weight is relative to the total weight of the tablet and wherein the dispersible tablet disintegrates in a liquid in less than 1 minute.

In one embodiment, provided herein is a dispersible tablet that comprises:
(i) about 60% by weight of Compound 1 Form II;
(ii) about 20% to about 35% by weight of microcrystalline cellulose;
(iii) about 1% to about 2% by weight of croscarmellose sodium;
(iv) less than about 2% by weight of colloidal silicon dioxide;
(v) about 1% to about 5% by weight of magnesium stearate;
(vi) a sweetener;
(vii) a flavoring agent; and
(viii) a coloring agent;
wherein the percentage by weight is relative to the total weight of the tablet and wherein the dispersible tablet disintegrates in a liquid in less than 1 minute.

In one embodiment, provided herein is a dispersible tablet that comprises:
(i) about 60% by weight of Compound 1 Form II;
(ii) about 20% to about 35% by weight of microcrystalline cellulose;
(iii) about 1% to about 2% by weight of croscarmellose sodium;
(iv) less than about 2% by weight of colloidal silicon dioxide;
(v) about 1% to about 5% by weight of magnesium stearate;
(vi) sucralose;
(vii) artificial grape flavor; and
(viii) iron oxide pigment;
wherein the percentage by weight is relative to the total weight of the tablet and wherein the dispersible tablet disintegrates in a liquid in less than 1 minute.

In one embodiment, provided herein is a dispersible tablet that comprises:
(i) about 60% by weight of Compound 1 Form II;
(ii) about 20% to about 35% by weight of microcrystalline cellulose;
(iii) about 1% to about 2% by weight of croscarmellose sodium;
(iv) less than about 2% by weight of colloidal silicon dioxide;
(v) about 1% to about 5% by weight of magnesium stearate;
(vi) about 1% to about 3% by weight of sweetener;
(vii) about 0.2% to about 1.5% by weight of flavoring agent; and
(viii) about 0.1% to about 1% by weight of coloring agent;
wherein the percentage by weight is relative to the total weight of the tablet and wherein the dispersible tablet disintegrates in a liquid in less than 1 minute.

In one embodiment, provided herein is a dispersible tablet that comprises:
(i) about 60% by weight of Compound 1 Form II;
(ii) about 20% to about 35% by weight of microcrystalline cellulose;
(iii) about 1% to about 2% by weight of croscarmellose sodium;
(iv) less than about 2% by weight of colloidal silicon dioxide;
(v) about 1% to about 5% by weight of magnesium stearate;
(vi) about 1% to about 3% by weight of sucralose;

(vii) about 0.2% to about 1.5% by weight of artificial grape flavor; and
(viii) about 0.1% to about 1% by weight of iron oxide pigment;

wherein the percentage by weight is relative to the total weight of the tablet and wherein the dispersible tablet disintegrates in a liquid in less than 1 minute.

In one embodiment, provided herein is a dispersible tablet that comprises:
(i) about 30% to about 70% by weight of Compound 1;
(ii) about 20% to about 35% by weight of filler;
(iii) about 1% to about 2% by weight of disintegrant;
(iv) less than about 2% by weight of glidant;
(v) a lubricant;
(vi) a sweetener;
(vii) a flavoring agent; and
(viii) a coloring agent;

wherein the percentage by weight is relative to the total weight of the tablet.

In one embodiment, provided herein is a dispersible tablet that comprises:
(i) about 50% to about 70% by weight of Compound 1;
(ii) about 20% to about 35% by weight of filler;
(iii) about 1% to about 2% by weight of disintegrant;
(iv) less than about 2% by weight of glidant;
(v) a lubricant;
(vi) a sweetener;
(vii) a flavoring agent; and
(viii) a coloring agent;

wherein the percentage by weight is relative to the total weight of the tablet.

In one embodiment, provided herein is a dispersible tablet that comprises:
(i) about 60% by weight of Compound 1;
(ii) about 20% to about 35% by weight of filler;
(iii) about 1% to about 2% by weight of disintegrant;
(iv) less than about 2% by weight of glidant;
(v) a lubricant;
(vi) a sweetener;
(vii) a flavoring agent; and
(viii) a coloring agent;

wherein the percentage by weight is relative to the total weight of the tablet.

In one embodiment, provided herein is a dispersible tablet that comprises:
(i) about 60% by weight of Compound 1 Form II;
(ii) about 20% to about 35% by weight of filler;
(iii) about 1% to about 2% by weight of disintegrant;
(iv) less than about 2% by weight of glidant;
(v) about 1% to about 5% by weight of lubricant;
(vi) a sweetener;
(vii) a flavoring agent; and
(viii) a coloring agent;

wherein the percentage by weight is relative to the total weight of the tablet.

In one embodiment, provided herein is a dispersible tablet that comprises:
(i) about 60% by weight of Compound 1 Form II;
(ii) about 20% to about 35% by weight of filler;
(iii) about 1% to about 2% by weight of disintegrant;
(iv) less than about 2% by weight of glidant;
(v) about 1% to about 5% by weight of lubricant;
(vi) about 1% to about 3% by weight of sweetener;
(vii) about 0.2% to about 1.5% by weight of flavoring agent; and
(viii) about 0.1% to about 1% by weight of coloring agent;

wherein the percentage by weight is relative to the total weight of the tablet.

In one embodiment, provided herein is a dispersible tablet that comprises:
(i) about 60% by weight of Compound 1 Form II;
(ii) about 20% to about 35% by weight of microcrystalline cellulose;
(iii) about 1% to about 2% by weight of croscarmellose sodium;
(iv) less than about 2% by weight of colloidal silicon dioxide;
(v) about 1% to about 5% by weight of magnesium stearate;
(vi) a sweetener;
(vii) a flavoring agent; and
(viii) a coloring agent;

wherein the percentage by weight is relative to the total weight of the tablet.

In one embodiment, provided herein is a dispersible tablet that comprises:
(i) about 60% by weight of Compound 1 Form II;
(ii) about 20% to about 35% by weight of microcrystalline cellulose;
(iii) about 1% to about 2% by weight of croscarmellose sodium;
(iv) less than about 2% by weight of colloidal silicon dioxide;
(v) about 1% to about 5% by weight of magnesium stearate;
(vi) about 1% to about 3% by weight of sweetener;
(vii) about 0.2% to about 1.5% by weight of a flavoring agent; and
(viii) about 0.1% to about 1% by weight of a coloring agent;

wherein the percentage by weight is relative to the total weight of the tablet.

In one embodiment, provided herein is a dispersible tablet that comprises:
(i) about 60% by weight of Compound 1 Form II;
(ii) about 20% to about 35% by weight of microcrystalline cellulose;
(iii) about 1% to about 2% by weight of croscarmellose sodium;
(iv) less than about 2% by weight of colloidal silicon dioxide;
(v) about 1% to about 5% magnesium stearate;
(vi) sucralose;
(vii) artificial grape flavor; and
(viii) iron oxide pigment;

wherein the percentage by weight is relative to the total weight of the tablet.

In one embodiment, provided herein is a dispersible tablet that comprises:
(i) about 60% by weight of Compound 1 Form II;
(ii) about 20% to about 35% by weight of microcrystalline cellulose;
(iii) about 1% to about 2% by weight of croscarmellose sodium;
(iv) less than about 2% by weight of colloidal silicon dioxide;
(v) about 1% to about 5% magnesium stearate;
(vi) about 1% to about 3% by weight of sucralose;
(vii) about 0.2% to about 1.5% by weight of artificial grape flavor; and
(viii) about 0.1% to about 1% by weight of iron oxide pigment;

wherein the percentage by weight is relative to the total weight of the tablet.

In one embodiment, provided herein is a dispersible tablet that comprises:
(i) an intragranular component comprising:
   (a) about 58% by weight of Compound 1 Form II;
   (b) about 26% by weight of microcrystalline cellulose;
   (c) about 1% by weight of croscarmellose sodium;
   (d) about 1.5% by weight of magnesium stearate;
   (e) about 0.5% by weight of colloidal silicon dioxide; and
(ii) an extragranular component comprising:
   (a) about 8% by weight of microcrystalline cellulose;
   (b) about 0.25% by weight of croscarmellose sodium;
   (c) about 0.8% by weight of magnesium stearate;
   (d) about 2.5% by weight of sucralose;
   (g) about 0.5% by weight of artificial grape flavor;
   (h) about 0.2% by weight of iron oxide pigment; and
   (viii) about 0.2% by weight of colloidal silicon dioxide;
wherein the percentage by weight is relative to the total weight of the tablet.

Manufacturing Processes

In one aspect, the tablets of the present disclosure can be prepared by dry granulation process. In one embodiment, the dry granulation process comprises: mixing Compound 1 with excipients and compacting the mix to form a compact mass. In another embodiment the compacts are milled to form dense flowable granules. The granular product is admixed with an extragranular component and compressed into tablets. Compaction can be done by conventional equipment. In one embodiment, the blended API and excipients are passed through a roller compactor, for example a Gerteis Minipactor, or Gerteis Macropactor, for compaction.

In one embodiment, a grade of MCC that increases the overall blend compressibility can yield drug loadings (w/w) of about: 40%-80%, 50%-80%, or 50%-70%. In one embodiment, a grade of MCC that increases the overall blend compressibility can yield drug loadings (w/w) of about: 40%, 50%, 55%, 60%, 65%, 66%, 68%, 70%, 72%, 75%, 80%, or more. In one embodiment, a grade of MCC that increases the overall blend compressibility can yield drug loadings (w/w) of at least: 40%, 50%, 55%, 60%, 65%, 66%, 68%, 70%, 72%, 75%, 80%, or more. Such drug yields can be useful in scalable manufacturing manner, e.g., adequate for large scale manufacturing purposes, in particular high tablet hardness and low friability.

In one embodiment, the tablets described herein include a drug loading of about 60%. At 60% load, 300 mg Form II of Compound 1 can be delivered from a 500 mg total tablet core weight. In one embodiment, the tablet is sufficiently sized to permit patients to swallow the tablet without difficulty. The dry granulation process described herein can be used to manufacture tablets comprising varying amounts of Compound 1. For example, the common blend can be tableted at to produce 300 mg, 600 mg, or 900 mg tablets. For a 900 mg tablet, a 1,500 mg total tablet core weight is needed. In some embodiments, for a 900 mg tablet, a 1,500 mg or 1,511 mg total tablet core weight is needed. In one embodiment, the tablet is sufficiently sized to permit patients to swallow the tablet without difficulty. In one embodiment, the tablets described herein provide advantages for ease of administration by patients over other dosages and dosage forms, which may result in increased patient compliance and clinical outcomes.

In some embodiments, the tablets described herein can be prepared by a wet granulation process. Wet granulation includes but is not limited to high/low shear wet granulation and fluid bed granulation. In some embodiments, Compound 1 and excipients (e.g., binder, disintegrant, surfactant, sweeteners, flavoring agents, and/or other excipients) are processed in a wet granulator and subsequently dried. The resulting granules are sized through a milling process, then blended with glidants and/or lubricants.

Various compression forces can be used to produce the tablets. The selected force used to compress tablets described herein meets the USP requirements for disintegration time. In some embodiments, the selected force for compression of a dispersible tablet described herein allows for a rapidly disintegration of the tablet that results in a flocculent suspension once the dispersible tablet is added to liquid for administration.

Methods

The tablets described herein are useful for the treatment of conditions associated with oxygen deficiency in a patient in need thereof and regardless of the age of the patient. Provided herein are methods of increasing affinity of hemoglobin for oxygen in a patient. In one embodiment, the methods comprise administering to the patient in need thereof a tablet described herein comprising a therapeutically effective amount of Compound 1. In one embodiment, the therapeutic amount of Compound 1 is from 600 mg to 2000 mg per day. In another embodiment, the therapeutic amount of Compound 1 is 600 mg. In another embodiment, the therapeutic amount of Compound 1 is 900 mg. In another embodiment, the therapeutic amount of Compound 1 is 1500 mg. In some embodiments, the therapeutic amount of Compound 1 is from 50 mg to 2000 mg per day. In some embodiments, the therapeutic amount of Compound 1 is from 50 mg to 1500 mg per day. In one embodiment, the therapeutic amount of Compound 1 is from 900 mg to 1500 mg per day. In one embodiment, the therapeutic amount of Compound 1 is from 600 mg to 1200 mg per day. In one embodiment, the therapeutic amount of Compound 1 is from 600 mg to 900 mg per day. In another embodiment, the methods comprise administering to the patient in need thereof a tablet described herein, wherein the tablet comprises about 900 mg to about 1500 mg of Compound 1. In another embodiment, the methods comprise administering to the patient in need thereof a tablet described herein, wherein the tablet comprises about 300 mg to 900 mg of Compound 1. In another embodiment, the methods comprise administering to the patient in need thereof a tablet described herein, wherein the tablet comprises about 300 mg of Compound 1 and wherein the administration is 1 to 5 times daily. In another embodiment, the methods comprise administering to the patient in need thereof a tablet described herein, wherein the tablet comprises about 300 mg of Compound 1 and wherein the patient is simultaneously administered 1 to 5 tablets. In another embodiment, the methods comprise administering to the patient in need thereof a tablet described herein, wherein the tablet comprises about 900 mg of Compound 1 and wherein the administration is once daily.

Also provided herein are methods of increasing affinity of hemoglobin for oxygen in a patient, wherein the patient is about 9 months old to about 11 years old. In one embodiment, the methods comprise administering to the patient in need thereof a tablet described herein comprising a therapeutically effective amount of Compound 1. In some embodiments, the tablet is mixed with an appropriate vehicle, such as food, prior to administration. In such embodiments, the tablet is crushed, mixed with food, and subsequently administered to the patient. In some embodiments, the therapeutic amount of Compound 1 is from 50 mg to 2000 mg per day. In one embodiment, the therapeutic amount of Compound 1 is from 600 mg to 2000 mg per day. In some embodiments, the therapeutic amount of Compound 1 is from 50 mg to 1500 mg per day. In some embodiments, the therapeutic amount of Compound 1 is from 100 mg to 600 mg per day. In one embodiment, the therapeutic amount of Compound 1 is from 600 mg to 900 mg per day. In another embodiment, the therapeutic amount of Compound 1 is 600 mg. In another embodiment, the therapeutic amount of Compound 1 is 900 mg. In another embodiment, the therapeutic amount of Compound 1 is 1500 mg. In another embodiment, the methods comprise administering to the patient in need thereof a tablet described herein, wherein the tablet comprises about 100 mg to 600 mg of Compound 1. In another embodiment, the methods comprise administering to the patient in need thereof a tablet described herein, wherein the tablet comprises about 100 mg to 300 mg of Compound 1. In another embodiment, the methods comprise administering to the patient in need thereof a tablet described herein, wherein the tablet comprises about 100 mg of Compound 1 and wherein the administration of the tablet is 1 to 9 times daily. In another embodiment, the methods comprise administering to the patient in need thereof a tablet described herein, wherein the tablet comprises about 300 mg of Compound 1 and wherein the administration of the tablet is 1 to 3 times daily. In another embodiment, the methods comprise administering to the patient in need thereof a tablet described herein, wherein the tablet comprises about 100 mg of Compound 1 and wherein the patient is simultaneously administered 1 to 9 tablets. In another embodiment, the methods comprise administering to the patient in need thereof a tablet described herein, wherein the tablet comprises about 300 mg of Compound 1 and wherein the patient is simultaneously administered 1 to 3 tablets.

Also provided herein are methods of increasing affinity of hemoglobin for oxygen in a patient, wherein the patient is about 9 months old to about 11 years old. In one embodiment, the methods comprise administering to the patient in need thereof a dispersible tablet described herein comprising a therapeutically effective amount of Compound 1. In some embodiments, the dispersible tablet is dissolved in a liquid prior to its administration to the patient. In some embodiments, the dispersible tablet is added to a liquid to be dispersed prior to its administration to the patient. In some embodiments, the liquid is water or other drink for consumption. In some embodiments, the dispersible tablet is dissolved in a liquid (for example, in a cup) prior to its administration to the patient, the liquid is administered to the patient, and the cup further rinsed with additional liquid, which is also administered to the patient. In some embodiments, the therapeutic amount of Compound 1 is from 50 mg to 2000 mg per day. In one embodiment, the therapeutic amount of Compound 1 is from 600 mg to 2000 mg per day. In some embodiments, the therapeutic amount of Compound 1 is from 100 mg to 600 mg per day. In one embodiment, the therapeutic amount of Compound 1 is from 600 mg to 900 mg per day. In another embodiment, the therapeutic amount of Compound 1 is 600 mg. In another embodiment the therapeutic amount of Compound 1 is 900 mg. In another embodiment the therapeutic amount of Compound 1 is 1500 mg. In another embodiment, the methods comprise administering to the patient in need thereof a tablet described herein, wherein the tablet comprises about 100 mg to 600 mg of Compound 1. In another embodiment, the methods comprise administering to the patient in need thereof a tablet described herein, wherein the tablet comprises about 100 mg to 300 mg of Compound 1. In another embodiment, the methods comprise administering to the patient in need thereof a tablet described herein, wherein the tablet comprises about 100 mg of Compound 1 and wherein the administration of the tablet is 1 to 9 times daily. In another embodiment, the methods comprise administering to the patient in need thereof a tablet described herein, wherein the tablet comprises about 300 mg of Compound 1 and wherein the administration of the tablet is 1 to 3 times daily. In another embodiment, the methods comprise administering to the patient in need thereof a tablet described herein, wherein the tablet comprises about 100 mg of Compound 1 and wherein the patient is simultaneously administered 1 to 9 tablets. In another embodiment, the methods comprise administering to the patient in need thereof a tablet described herein, wherein the tablet comprises about 300 mg of Compound 1 and wherein the patient is simultaneously administered 1 to 3 tablets.

Further provided herein are methods for treating a condition associated with oxygen deficiency in a patient. In one embodiment, the method comprises administering to the patient having a condition associated with oxygen deficiency; a tablet described herein comprising a therapeutically effective amount of Compound 1. In one embodiment, the condition is sickle cell disease, cancer, a pulmonary disorder such as interstitial pulmonary fibrosis, stroke, high altitude sickness, an ulcer, a pressure sore, acute respiratory disease syndrome, acute lung injury, or a wound. In one embodiment, the condition is sickle cell disease, cancer, a pulmonary disorder such as interstitial pulmonary fibrosis, stroke, high altitude sickness, an ulcer, a pressure sore, Alzheimer's disease, acute respiratory disease syndrome, acute lung injury, or a wound. In one embodiment, the condition is sickle cell disease, cancer, a pulmonary disorder such as idiopathic pulmonary fibrosis, stroke, high altitude sickness, an ulcer, a pressure sore, Alzheimer's disease, acute respiratory disease syndrome, acute lung injury, or a wound. In one embodiment, the condition is sickle cell disease. In one embodiment, the conditions is a pulmonary disorder. In one embodiment, the pulmonary disorder is interstitial pulmonary fibrosis. In one embodiment, the pulmonary disorder is idiopathic pulmonary fibrosis. In one embodiment, the therapeutic amount of Compound 1 is from 600 mg to 2000 mg once a day. In another embodiment, the therapeutic amount of Compound 1 is 600 mg. In another embodiment, the therapeutic amount of Compound 1 is 900 mg. In another embodiment the therapeutic amount of Compound 1 is 1500 mg.

In one embodiment, the therapeutically effective amount of Compound 1 is from 600 to 2000 mg once a day. In one embodiment, the therapeutically effective amount of Compound 1 is 900 mg or 1500 mg once a day. In one embodiment, the tablet contains 300, 750 or 900 mg of 2-hydroxy-6-((2-(1-isopropyl-1H-pyrazol-5-yl)pyridin-3-yl)methoxy) benzaldehyde.

It is understood that modifications which do not substantially affect the activity of the various embodiments of this disclosure are also included within the definition of the disclosure provided herein. Accordingly, the following examples are intended to illustrate but not limit the present disclosure.

EXAMPLES

Example 1: Compression Profile of Form II of Compound 1

The compressibility of crystalline Form II of Compound 1 ("API") was determined by compressing neat unformulated API at 200 mg scale compressed in a hydraulic press using 5/16th inch diameter, standard concave round tooling. The resulting tablets were measured for thickness using a digital caliper gauge, and for tensile strength using a tablet hardness tester. Table 1 shows the results of this compressibility study using 3 samples of Form II of Compound 1 (Lots 1a, 1b, and 2). Lots 1a and 2 were directly from the API manufacturing process, but from different API suppliers. Lot 1b was prepared by taking Lot 1a and subjecting it to hammer milling to cause reduction of particle size.

TABLE 1

| Compound 1 Form II API Lot # | Compression Force (lbf) | Tablet Thickness (mm) | Tablet Hardness (kp) |
| --- | --- | --- | --- |
| 1a | 2000 | 4.50 | 1.8 |
|  | 3000 | 4.34 | 1.5 |
|  | 4000 | 4.35 | 1.0 |
| 1b | 2000 | 4.55 | 2.4 |
| (hammer milled | 3000 | 4.32 | 1.2 |
| lot 1a) | 4000 | 4.43 | 1.5 |
| 2 | 2000 | 4.50 | 9.0 |
|  | 3000 | 4.27 | 3.7 |
|  | 4000 | 4.31 | 3.4 |

The compression profiles in Table 1 indicate low tablet hardness and that Form II of Compound 1 is a relatively incompressible solid. The implication of this is that compression of neat API does not achieve a tensile strength relevant for pharmaceutical tablet manufacture. Further, Form II of Compound 1 exhibits a flat or slightly negative response of hardness resulting from increasing compressive force. Hence compression at higher forces doesn't enable higher tensile strength tablets to be manufactured. Consequently neat API tablets would have weak integrity and be overly friable, prone to crumbling during manufacturing process, packaging, transport and storage in bottle or blister states. Milling of one lot of API did not result in appreciably increased tablet hardness. Increasing compression force if anything, resulted in slight over compression (slightly decreasing hardness at higher compression force). This may arise from breakage of crystals and agglomerates at higher tableting compression force. Overall, the Form II of Compound 1 compression profile is not acceptable as a neat API and requires formulation with excipients to overcome poor compression properties.

Example 2: Formulation and Manufacture of G1 and G2 Prototypes (Lab Scale)

Tablets of Form II of Compound 1 were prepared in 2 similar formulations: G1 and G2. G2 was compositionally the same as G1, except it also contained 1.5% sodium lauryl sulfate in the extragranular phase, and a concurrent 1.5% decrease in the extragranular level of extragranular MCC filler. Tables 2 and 3 below give the compositions. The tablets were prepared using the following sequence of manufacturing steps:

Form II of Compound 1 was blended with the intragranular quantities of microcrystalline cellulose and croscarmellose sodium, and then further blended with the intragranular quantity of magnesium stearate. The powder pre-blend was dry granulated by roller compaction, and then milled to produce granules. The granules were blended with the extragranular quantities of microcrystalline cellulose, croscarmellose sodium, and sodium lauryl sulfate (for G2 only), and then further blended with the extragranular quantity of magnesium stearate. The final blend was compressed into tablets using a tablet press.

TABLE 2

Composition of G1 Formulation of Form II of Compound 1 Tablets at 300 mg and 100 mg Strengths

| Ingredient | Grade | Conc. (% w/w) | Unit Weight (mg/tablet) | Unit Weight (mg/tablet) | Function |
| --- | --- | --- | --- | --- | --- |
| Intragranular |  |  |  |  |  |
| Compound 1 Form II, API | N/A | 60.00 | 300.00 | 100.00 | Active |
| Microcrystalline Cellulose | Ceolus ™ UF-711 | 27.50 | 137.50 | 45.83 | Filler |
| Croscarmellose Sodium | Ac-Di-Sol ® SD-711 | 1.00 | 5.00 | 1.67 | Disintegrant |
| Magnesium Stearate | Ligamed MF-2-V | 1.50 | 7.50 | 2.50 | Lubricant |
| Extragranular |  |  |  |  |  |
| Microcrystalline Cellulose | Ceolus ™ UF-711 | 9.00 | 45.00 | 15.00 | Filler |
| Croscarmellose Sodium | Ac-Di-Sol ® SD-711 | 0.25 | 1.25 | 0.42 | Disintegrant |
| Magnesium Stearate | Ligamed MF-2-V | 0.75 | 3.75 | 1.25 | Lubricant |
| Total |  | 100% | 500 mg | 167 mg |  |

TABLE 3

Composition of G2 Formulation of Form II of Compound 1 Tablets at 300 mg and 100 mg Strengths

| Ingredient | Grade | Conc. (% w/w) | Unit Weight (mg/tablet) | Unit Weight (mg/tablet) | Function |
| --- | --- | --- | --- | --- | --- |
| Intragranular |  |  |  |  |  |
| Compound 1 Form II, API[a] | N/A | 60.00 | 300.00 | 100.00 | Active |
| Microcrystalline Cellulose[a] | Ceolus ™ UF-711 | 27.50 | 137.50 | 45.83 | Filler |
| Croscarmellose Sodium | Ac-Di-Sol ® SD-711 | 1.00 | 5.00 | 1.67 | Disintegrant |
| Magnesium Stearate | Ligamed MF-2-V | 1.50 | 7.50 | 2.50 | Lubricant |

TABLE 3-continued

Composition of G2 Formulation of Form II of Compound 1 Tablets at 300 mg and 100 mg Strengths

| Ingredient | Grade | Conc. (% w/w) | Unit Weight (mg/tablet) | Unit Weight (mg/tablet) | Function |
|---|---|---|---|---|---|
| Extragranular | | | | | |
| Microcrystalline Cellulose | Ceolus ™ UF-711 | 7.50 | 37.50 | 12.50 | Filler |
| Croscarmellose Sodium | Ac-Di-Sol ® SD-711 | 0.25 | 1.25 | 0.42 | Disintegrant |
| Sodium Lauryl Sulfate | Kolliphor ® SLS Fine | 1.50 | 7.50 | 2.50 | Surfactant |
| Magnesium Stearate | Ligamed MF-2-V | 0.75 | 3.75 | 1.25 | Lubricant |
| | Total | 100% | 500 mg | 167 mg | |

Example 3: Accelerated Stability Testing of G1 and G2 Prototypes

Tablets of G2 were tested for stability at stressed storage conditions to accelerate stability testing. 100 mg G2 tablets were packaged in high density polyethylene bottles, and induction sealed with a aluminum foil faced lined cap. The bottles were stored in an environmental chamber at 40° C., 75% relative humidity (RH), and also in a chamber at 25° C., 60% RH to replicate ICH (International Conference on Harmonization) storage conditions. The tablets were tested at time zero and post 1 month of storage for appearance, assay, impurities, and dissolution properties. Table 4 summarizes the stability results.

TABLE 4

Stability data of Form II of Compound 1 tablets, 100 mg strength

| Stability Condition | Storage Time | Appearance | Assay | Total Impurities | Dissolution (% released at 60 min) |
|---|---|---|---|---|---|
| 25° C./ 60% RH | Time zero | Off-white tablets | 96.0% | <0.05% | 98 |
| | 1 month | Off-white tablets | 96.3% | <0.05% | 102 |
| 40° C./ 75% RH | Time zero | Off-white tablets | 96.0% | <0.05% | 98 |
| | 1 month | Off-white tablets | 96.4% | <0.05% | 98 |

The stability data demonstrates there were no significant changes in appearance, no loss of assay, no growth in impurities or degradants, and complete dissolution release within experimental limits. Therefore G2 tablet has good stability characteristics with no gross chemical incompatibilities between Form II of Compound 1 and the composite excipients. Since the 300 mg and higher strengths of Form II of Compound 1 G2 tablets are made using a common blend, the stability properties of the 100 mg strength tablet are representative of all strengths, such as 300-900 mg strengths.

Example 4: In Vitro Dissolution Testing of G1 and G2 Prototype Formulations

A dissolution study was conducted to compare the G1 and G2 tablet formulations and a formulated capsule product. This used a USP paddle dissolution apparatus and method. Each of six dissolution vessels was filled with 900 mL of dissolution media, including 0.1N hydrochloric acid, and 0.5% Tween 80 surfactant; the paddle was rotated at 75 RPM, and the extent of release was determined by concentration measurements at a UV absorbance detection wavelength of 345 nm. The compositions of the capsule shells; Compound 1, Form II Capsules; and Compound 1, Form II Common Placebo Capsules are given in Tables 5, 6, and 7, respectively. The dissolution profiles are given in FIG. 1. The G2 tablet formulation was tested at both uncoated state (100 mg) and film coated higher strength state (300 mg).

TABLE 5

Composition of the capsule shell

| Component | Function | Reference to Standards |
|---|---|---|
| HPMC (hypromellose) | Structure | (EU) 231/2012, Ph. Eur., JP, USP/NF |
| Red iron oxide | Colorant | (EU) 231/2012, 21 CFR, JPE, USP/NF |
| Titanium dioxide | Opacifier | (EU) 231/2012, 21 CFR, Ph. Eur., JP, USP/NF |

NF = National Formulary;
Ph. Eur. = European Pharmacopoeia;
USP = United States Pharmacopeia;
JP = Japanese Pharmacopoeia

TABLE 6

Quantitative Composition of Compound 1, Form II Capsules (300 mg)

| Components | Quantity (% w/w) | Quantity (mg/capsule) | Function | Reference to Standard or similar |
|---|---|---|---|---|
| Compound 1 Form II, Unmilled | 85.71 | 300.00 | Drug substance | In-house |
| Hydroxypropyl methylcellulose (Methocel ® E5 Premium LV) | 4.00 | 14.00 | Binder | USP |
| Microcrystalline Cellulose (Avicel ® PH-101) | 3.64 | 12.74 | Filler | NF |
| Lactose Monohydrate (Foremost Grade 310) | 2.65 | 9.28 | Filler | NF |
| Croscarmellose Sodium (Ac-Di-Sol ®) | 3.50 | 12.25 | Disintegrant | Ph. Eur./NF |

TABLE 6-continued

Quantitative Composition of Compound 1, Form II Capsules (300 mg)

| Components | Quantity (% w/w) | Quantity (mg/capsule) | Function | Reference to Standard or similar |
|---|---|---|---|---|
| Sterile Water for Irrigation[a] | N/A | N/A | Granulation Liquid | USP |
| Magnesium Stearate (Hyqual ®, Vegetable Source) | 0.50 | 1.75 | Lubricant | NF |
| Total Fill Weight | 100.00 | 350.02 | — | — |
| HPMC (hydroxypropyl methylcellulose (hypromellose)), Swedish orange opaque, Vcaps ® Plus Coni-Snap, capsules, size 0 | N/A | 96.0 | Capsule shell | USP/NF, Ph.Eur. |
| Total Weight | N/A | 446.02 | — | — |

The composition of the Compound 1, Form II Common Placebo Capsules is provided below in Table 7 below.

TABLE 7

Composition of Compound 1, Form II Common Placebo Capsules

| Components | Composition per Capsule (mg) | Function | Reference to Standards |
|---|---|---|---|
| Microcrystalline cellulose [#] | 298.5 | Bulking Agent | NF, Ph. Eur., JP |
| Magnesium Stearate, NF | 1.5 | Lubricant | NF, Ph. Eur. |
| HPMC (hydroxypropyl-methylcellulose (hypromellose)), Swedish orange opaque, Vcaps ® Plus Coni-Snap, capsules, size 0 | 1 unit (96 mg) | Capsule shell | Supplier's in-house |

[#] Avicel pH-102, or equivalent

The dissolution data (FIG. 1) shows that the G1 and G2 tablet formulations each achieved pharmaceutically useful release consistent with immediate release profile products. The G2 formulation is superior to G1 in that it achieves the most rapid and complete release profile compared to G1 and to the capsule product. This indicates that the SLS surfactant in G2 is assisting in the release of Form II of Compound 1 from the highly compacted tablet state in order to replicate the release observed from the non-compressed state in capsules, and with a more rapid rate of release. Further, the capsule product had been historically used in clinical trials where doses in the range of 300-900 mg have demonstrated efficacy in treating patients suffering SCD. Therefore this data is confirming that the SLS surfactant is a surprisingly useful functional excipient in order to make pharmaceutically useful tablets of Compound 1 Form II as shown in the dissolution profile as compared to Formulation G1. Formulation G1 in vivo also showed a reasonable bioavailability profile. This data also shows that the G2 tablet formulation has release properties by USP dissolution methods that are independent of tablet strength as well as independent of film coating versus uncoated tablet cores.

Example 5: In Vivo Absorption Study (Dog PK) of G1 and G2 Formulations and Capsule Products A beagle dog oral delivery study was performed to assess the absorption characteristics of the G1 and G2 tablets, and compared to the capsule product. Each prototype was prepared at 100 mg strength. Table 8 summarizes the results of this study. The bioavailability relative to the capsule product was calculated on a relative basis to compare the systemic exposure of G1 and G2 tablets to the capsules.

TABLE 8

| Product | Cmax (CV %) (µg/mL) | AUC (CV %) (h · µg/mL) | Bioavailability relative to capsule |
|---|---|---|---|
| G1 tablet - 100 mg | 7.80 (56.7) | 650 (31.0) | 83.3% |
| G2 tablet - 100 mg | 8.25 (19.9) | 770 (21.8) | 101.9% |

CV % is the coefficient of variation expressed as a percentage

The pharmacokinetic data reveals that in vivo the G1 and G2 tablets have pharmaceutically useful absorption characteristics. Surprisingly, and consistent with the dissolution behavior, the G2 formulation of tablets exhibited an exposure equivalent to the capsules, which had previously demonstrated human clinical efficacy in treating SCD in the dose range of 300-900 mg. It is very useful that the G2 tablets (containing 1.5% SLS surfactant) are able to achieve comparable systemic exposure, despite having been subjected to high mechanical compression force. This enables Form II of Compound 1 to be provided in significantly higher doses per unit tablet (versus per capsule), and without any loss in extent of release or absorption. What is further surprising is that the SLS surfactant demonstrates a reduction in the variability of Cmax and AUC PK parameters. Reducing variability of Cmax is particularly useful for managing potential side effects, which are frequently found to be more extreme at the Cmax state where exposure concentration is at its peak. By reducing variability of Cmax, the risk of some patients experiencing Cmax related toxicities is reduced and thereby G2 is a more biopharmaceutically robust product. Variability in Cmax after capsule dosing in the same beagle dogs was observed at 31.5% and 50.1%. Despite the function of SLS being a surfactant to aid wetting of powder in aqueous media, SLS was observed here to be very useful in reducing variability of Cmax which has benefits for the overall safety and toxicity profile of Compound 1. Likewise, the AUC exposure was reduced to a very favorably low level of variability in the G2 tablet product, with CV %=21.8%. The capsule product in these beagle dogs showed variability on AUC of 30.4%, and 52.2%. Therefore both G1 and G2 tablets exhibited less variability in AUC exposure than capsules, and in fact the G2 tablet formulation showed the least variability across these products. A CV % of 21.8% is favorably low in a beagle dog study and further supports the pharmaceutical utility of both the G1 and G2 tablet formulations.

Example 6: Production of G2 Tablet Product at 5 kg Batch Scale

The G2 tablet formulation at 300 mg strength was scaled up to 5.720 kg batch size and run under GMP conditions to manufacture clinical trial tablets of Form II of Compound 1. Per the process described stepwise in example 3a, 3.3 kg of Form II of Compound 1 and the corresponding quantities of intragranular excipients excluding magnesium stearate were blended in a V-shell blender at a blend speed of 25 rpm, and blend time of 10 minutes. This pre-mix was passed through a co-mill at 655 rpm to ensure any agglomerates were broken to free flowing powder. The intragranular magnesium stearate was added, and the pre-blend was further blended in the V-shell blender at 25 rpm for 3 minutes. The pre-blend was processed in a roller compactor at a gap width target of 1.5 mm, 3.5 kN/cm force, and roll speed of 3 rpm. Ribbon compacts were milled to granules using a 1.00 mm sized screen and granulator rotor. Extragranular excipient were blended with the granules, excluding magnesium stearate, for 25 rpm, 7 minutes. Then further blended with the extragranular quantity of magnesium stearate for 3 minutes at 25 rpm.

Tablets were compressed from the final blend at a compression force of 18.6 kN, a pre-compression force of 1.6 kN, and a press speed of 20 rpm in a 9 station rotary tablet press. The tablets had an average hardness of 12.9 kp, exhibited very low or negligible friability (0.1% and 0.0% weight loss for 6.5 g of tablets tumbled in a USP friabilator for 4 minutes). The tablets had rapid disintegration in 37° C. water (1 min 4 seconds, and 1 minute 10 seconds) tested by the USP disintegration method.

The tablets were film coated with a cosmetic coating Opadry II coating system at a target rate of 15 g/min coating suspension until a target film coating weight gain of 4% was achieved. The tablets were tested by validated analytical methods meeting all product quality acceptance criteria, and released for human clinical use.

Example 7: Compound 1 Tablets with Glidant

Tablets of Compound 1 Form II and a glidant were prepared according to the Examples provided herein. These tablets are summarized in Table 9a and 9b.

TABLE 9a

Composition of Form II of Compound 1 High Strength Tablets with Glidant

| Component | Quantity (% w/w) | Unit Weight (mg/tablet) | Function |
|---|---|---|---|
| Intragranular | | | |
| Compound 1 Form II | 59.55 | 900.0 | Active |
| Microcrystalline Cellulose | 27.29 | 412.4 | Filler |
| Croscarmellose Sodium | 0.99 | 15.0 | Disintegrant |
| Magnesium Stearate[a] | 1.49 | 22.5 | Lubricant |
| Colloidal Silicon Dioxide[b] | 0.49 | 7.5 | Glidant |
| Extragranular | | | |
| Microcrystalline Cellulose | 7.44 | 112.4 | Filler |
| Croscarmellose Sodium | 0.25 | 3.8 | Disintegrant |
| Sodium Lauryl Sulfate | 1.49 | 22.5 | Surfactant |
| Colloidal Silicon Dioxide[b] | 0.75 | 11.3 | Glidant |
| Magnesium Stearate[a] | 0.74 | 11.2 | Lubricant |
| Core Total | 100.48 | 1518.6 | — |
| Film Coating (Color Coat) | | | |
| Opadry II Yellow System | 4.0[b] | 60 | Cosmetic (color) |
| Coated Total | 104.48 | 1578.6 | — |

[a]From a vegetable source
[b]The colloidal silicon dioxide component can be adjusted between intragranular and extragranular additions TABLE 9b Composition of Form II of Compound 1 High Strength Tablets with Glidant

| Component | Quantity (% w/w) | Unit Weight (mg/tablet) | Function |
|---|---|---|---|
| Intragranular | | | |
| Compound 1 Form II | 59.55 | 900 | Active |
| Microcrystalline Cellulose | 27.0 | 408 | Filler |
| Croscarmellose Sodium | 1.0 | 15 | Disintegrant |
| Magnesium Stearate[a] | 1.5 | 23 | Lubricant |
| Colloidal Silicon Dioxide[b] | 0.5 | 8 | Glidant |
| Extragranular | | | |
| Microcrystalline Cellulose | 7.2 | 109 | Filler |
| Croscarmellose Sodium | 0.25 | 4 | Disintegrant |
| Sodium Lauryl Sulfate | 1.5 | 23 | Surfactant |
| Colloidal Silicon Dioxide[b] | 0.75 | 11 | Glidant |
| Magnesium Stearate[a] | 0.75 | 11 | Lubricant |
| Core Total | 100.0 | 1512 | — |
| Film Coating (Color Coat) | | | |
| Opadry II Yellow System | 4.0 | 60 | Cosmetic (color) |
| Coated Total | 104.00 | 1571 | — |

[a]From a vegetable source
[b]The colloidal silicon dioxide component can be adjusted between intragranular and extragranular additions

Example 8: Dispersible Tablets

Dispersible tablets of Form II of Compound 1 were prepared according to the Examples provided herein without the addition of a film coating.

Dispersible tablets having 300 mg or 900 mg of Form II of Compound 1 are summarized in Table 10.

TABLE 10

Compositions of Dispersible Tablets of Form II
of Compound 1 at 300 mg and 900 mg Strengths

| Component | Quantity (% w/w) | Unit Weight (mg/tablet) | Unit Weight (mg/tablet) | Function | Reference to Standard or similar |
|---|---|---|---|---|---|
| Intragranular | | | | | |
| Compound 1 Form II | 58.45 | 300.0 | 900.0 | Active | |
| Microcrystalline Cellulose | 26.30 | 135.0 | 405.0 | Filler | USP/NF/Ph. Eur. |
| Croscarmellose Sodium | 0.97 | 5.0 | 14.9 | Disintegrant | USP/NF/Ph. Eur. |
| Magnesium Stearate$^a$ | 1.46 | 7.5 | 22.5 | Lubricant | USP/NF/Ph. Eur. |
| Colloidal Silicon Dioxide$^b$ | 0.49 | 2.5 | 7.5 | Glidant | USP/NF/Ph. Eur. |
| Extragranular | | | | | |
| Microcrystalline Cellulose | 7.80 | 40.0 | 120.1 | Filler | USP/NF/Ph. Eur. |
| Croscarmellose Sodium | 0.25 | 1.3 | 3.8 | Disintegrant | USP/NF/Ph. Eur. |
| Magnesium Stearate$^a$ | 0.73 | 3.7 | 11.2 | Lubricant | USP/NF/Ph. Eur. |
| Sucralose | 2.53 | 13.0 | 39.0 | Sweetener | USP/NF/Ph. Eur. |
| Artificial Grape Flavor | 0.54 | 2.8 | 8.3 | Flavor | FEMA GRAS CFR |
| Iron Oxide Pigment | 0.24 | 1.2 | 3.7 | Colorant | NF, JPE, E172 |
| Colloidal Silicon Dioxide$^b$ | 0.24 | 1.2 | 3.7 | Glidant | USP/NF/Ph. Eur. |
| Total | 100.00 | 513.3 | 1539.8 | — | — |

$^a$From a vegetable source
$^b$The colloidal silicon dioxide component can be adjusted between intragranular and extragranular additions Dispersible tablets having 50 mg or 100 mg of Form II of Compound 1 are summarized in Table 11.

TABLE 11

| | | mg/Tablets | |
|---|---|---|---|
| Ingredients | % w/w | 50 mg Strength | 100 mg Strength |
| Compound 1 Form II | 58.45 | 50.00 | 100.00 |
| Microcrystalline Cellulose | 34.10 | 29.17 | 58.34 |
| Croscarmellose Sodium | 1.22 | 1.04 | 2.09 |
| Magnesium Stearate | 2.19 | 1.87 | 3.75 |
| Sucralose | 2.53 | 2.16 | 4.33 |
| Artificial Grape Flavor | 0.54 | 0.46 | 0.92 |
| Iron Oxide Yellow Pigment | 0.24 | 0.21 | 0.41 |
| Colloidal Silicon Dioxide | 0.73 | 0.62 | 1.25 |
| Total | 100.00 | 85.54 | 171.09 |

Example 9: Evaluation of Impact of Disintegrant Levels in Dispersible Tablets One of the salient features of a dispersible tablet is to have a rapid dispersion time in a small volume of solution, in addition to having other standard tablet characteristics, such as tablet hardness and friability, within an acceptable range. Tablet hardness and friability are also important because high friability in tablets leads to breakage in tablets during processing, packaging and transportation. Typically, hardness is directly proportional to dispersion time, but indirectly proportional to friability within a certain range. In order to achieve rapid dispersion times with acceptable tablet hardness and friability, dispersible tablets typically include higher percentage of disintegrants (also called a superdisintegrant and generally in the range of 5 to 20% w/w) compared to standard, non-dispersible tablets. Surprisingly, as shown in Table 12, a dispersible tablet having only 1.25% w/w croscarmellose sodium displayed superior dispersion characteristics (i.e. rapid disintegration times) with dispersion times of less than 60 seconds, while maintaining acceptable tablet hardness and friability.

The impact of disintegrant levels in dispersible tablets of Compound 1 with increasing amounts of croscarmellose sodium was evaluated, and the results are summarized in Table 12. The dispersible tablets at 300 mg strength (and compressed at 2500 psi using a manual tablet press) used for these studies are also summarized in Table 12. These tablets were prepared as follows.

A dry granulation process using a roller compactor was used for preparation of the tablet blend and tablets were compressed using a manual tablet press.

Pre-Blending: All the intragranular excipients were weighed out and sieved to remove any agglomerates.

Roller Compaction (Dry Granulation) and Milling: The pre-blend (intragranular) was then passed through a small-scale bench top roller compactor and a mill to obtain the granulation (intragranular portion) blend.

Final Blend: The extragranular components were weighed and sieved to remove any agglomerates. The intragranular and the extragranular components were then mixed together using a small-scale bench top bottle blender to obtain the final blend (common blend) for compression into tablets.

Tablet Compression: 300 mg Dispersible Tablets were prepared with the final blend using a manual tablet press. Compressed tablets were evaluated for tablet hardness, thickness, friability and dispersion time.

Tablet characterization were performed as follows:

Tablet Hardness and Thickness: Tablet hardness or tablet breaking force as per United States Pharmacopoeia ("USP") is the measure of the mechanical integrity of tablets. Tablet hardness, along with the thickness, was measured using a standard hardness tester as described in the USP.

Tablet Friability: As per USP, tablet friability is a test of the ability of tablets to withstand mechanical stresses that determines their resistance to chipping and surface abrasion by tumbling them in a rotating cylinder. The percentage weight loss after tumbling is referred to as the friability of the tablets. Tablet friability for Compound 1 tablets were tested using a friability tester designed as per USP specifications.

Dispersion Time: This study simulates a possible administration method of dispersible tablets to a patient. The method involves adding a dispersible tablet in a pre-measured amount of water in a plastic dosing cup. Water is absorbed into the tablet and disintegrates rapidly to form a fine dispersion; the time taken for the tablet to completely disperse in the water (without any hard tablet aggregates or unmoistened tablet core) is the dispersion time.

TABLE 12

| Ingredients (% w/w in Tablet Formulation) | 0% Ac-Di-Sol® | 0.625% w/w Ac-Di-Sol® | 1.25% w/w Ac-Di-Sol® | 2.7% w/w Ac-Di-Sol® | 5.3% w/w Ac-Di-Sol® | 5% w/w Ac-Di-Sol® (4% IG, 1% EG) |
|---|---|---|---|---|---|---|
| Microcrystalline Cellulose | 34 | 34 | 35 | 34 | 33 | 31.0 |
| Croscarmellose Sodium (Ac-Di-Sol®) | 0 | 1 | 1 | 3 | 5 | 5.0 |
| Ratio | 0 | 54 | 28 | 13 | 6 | 6 |
| 300 mg Dispersible Tablets Compressed at 2500 psi Force using Manual Tablet Press | | | | | | |
| Dispersion Time (Sec) 5 mL Water | >300 | 57 | 35 | 28 | 35 | 37 |
| Tablet Hardness (kp) | 13 | 13 | 13 | 13 | 12 | 15 |
| Friability (%) | ND | ND | 0.22 | 0.23 | 0.19 | 0.24 |

IG: Intragranular Portion;
EG: Extragranular Portion;
ND: Not Determined

As shown in Table 12, at 0% croscarmellose sodium, the tablets took more than 5 minutes to disperse, and the quality of the dispersion (observed visually) was also poor. It is contemplated that the larger particles of these tablets can potentially impact the mouthfeel after administration, such as producing an unpleasant mouthfeel, which would then negatively impact a patient's compliance of a dosing regimen.

As the percentage of croscarmellose sodium was increased from 0% to 0.625% w/w of the tablet, the dispersion time showed significant improvement. A fine dispersion (as observed visually) was formed in less than 60 seconds. It is contemplated that these fine dispersed particles would produce less mouthfeel, which would thus enhance a patient's compliance of a dosing regimen.

This data demonstrates the uniqueness of the dispersible tablets described herein; specifically, even with a small amount of croscarmellose sodium (for example, 0.625% w/w of the tablet), a significant improvement in the dispersion time and quality of dispersion was observed.

As shown in Table 12, a dispersible tablet with 1.25% w/w croscarmellose sodium displayed superior dispersion characteristics (i.e. rapid disintegration times) with dispersion times of less than 60 seconds while having acceptable tablet hardness and friability.

It is interestingly noted that no further improvement in the dispersion time was observed as the percentage of croscarmellose sodium was increased from 1.25% to up to 5.3% w/w. This data demonstrates that, unlike typical dispersible tablets, the dispersible tablets described herein do not require a high quantity of crosscarmellose sodium. Consequently, a desirable quantity of the filler (such as microcrystalline cellulose) in the tablets can be maintained for tablet hardness and friability.

As shown in Table 12, there was no impact from the addition of the disintegrant either as an intragranular or extragranular component.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A tablet comprising:
   (i) about 50% to about 70% by weight of Compound 1 of formula:

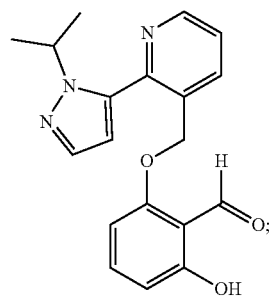 [SMILES: CC(C)n1nccc1-c1ncccc1COc1cccc(O)c1C=O]

(ii) about 30% to about 40% by weight of microcrystalline cellulose;
   (iii) about 0.25% to about 3% by weight of croscarmellose sodium;
   (iv) about 1% to about 5% by weight of magnesium stearate;
   (v) about 0.5% to about 2.5% of sodium lauryl sulfate; and (vi) about 0.25% to about 5% by weight of colloidal silicon dioxide;

wherein the percentage by weight is relative to the total weight of the tablet.

2. The tablet of claim 1, comprising:
(i) about 35% by weight of microcrystalline cellulose;
(ii) about 1.25% by weight of croscarmellose sodium;
(iii) about 2% by weight of magnesium stearate; and
(iv) about 1.5% by weight of sodium lauryl sulfate.

3. The tablet of claim 1, wherein the tablet comprises from about 300 to about 900 mg of Compound 1.

4. The tablet of claim 1, comprising about 60% by weight of Compound 1.

5. The tablet of claim 1, comprising about 35% by weight of microcrystalline cellulose.

6. The tablet of claim 1, comprising about 1.25% by weight of croscarmellose sodium.

7. The tablet of claim 1, comprising about 2% magnesium stearate.

8. The tablet of claim 1, comprising about 1.5% of sodium lauryl sulfate.

9. The tablet of claim 1, wherein the tablet comprises from about 100 to about 600 mg of Compound 1.

\* \* \* \* \*